United States Patent
Cullis et al.

(10) Patent No.: US 12,377,080 B2
(45) Date of Patent: Aug. 5, 2025

(54) ALLOSTERIC EGFR INHIBITORS AND METHODS OF USE THEREOF

(71) Applicant: Dana-Farber Cancer Institute, Inc., Boston, MA (US)

(72) Inventors: Courtney A. Cullis, Bedford, MA (US); Krista E. Gipson, Medford, MA (US); Yongbo Hu, Winchester, MA (US); Shih-Chung Huang, Lexington, MA (US); Nathanael S. Gray, Jamaica Plain, MA (US); David A. Scott, Newton, MA (US); Thomas Gero, Stow, MA (US); David Heppner, Brookline, MA (US); Tyler Beyett, Brookline, MA (US); Ciric To, Medford, MA (US); Michael Eck, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 897 days.

(21) Appl. No.: 17/596,720

(22) PCT Filed: Jun. 19, 2020

(86) PCT No.: PCT/US2020/038672
§ 371 (c)(1),
(2) Date: Mar. 31, 2022

(87) PCT Pub. No.: WO2020/257607
PCT Pub. Date: Dec. 24, 2020

(65) Prior Publication Data
US 2022/0378757 A1    Dec. 1, 2022

Related U.S. Application Data

(60) Provisional application No. 63/007,210, filed on Apr. 8, 2020, provisional application No. 62/864,899, filed on Jun. 21, 2019.

(51) Int. Cl.
| | | |
|---|---|---|
| *C07D 471/04* | (2006.01) | |
| *A61K 31/437* | (2006.01) | |
| *A61K 31/444* | (2006.01) | |
| *A61K 31/496* | (2006.01) | |
| *A61K 31/506* | (2006.01) | |
| *A61K 39/395* | (2006.01) | |

(52) U.S. Cl.
CPC .......... *A61K 31/437* (2013.01); *A61K 31/444* (2013.01); *A61K 31/496* (2013.01); *A61K 31/506* (2013.01); *A61K 39/3955* (2013.01); *C07D 471/04* (2013.01)

(58) Field of Classification Search
CPC .. A61K 31/437; A61K 31/444; A61K 31/496; A61K 31/506; A61K 39/3955; C07D 471/04
See application file for complete search history.

(56) References Cited

U.S. PATENT DOCUMENTS

| | | | |
|---|---|---|---|
| 2004/0053948 A1* | 3/2004 | McDonald | A61K 31/4709 514/309 |
| 2018/0193470 A1 | 7/2018 | Crew et al. | |
| 2018/0290975 A1 | 10/2018 | Gray et al. | |
| 2019/0106417 A1 | 4/2019 | Gray et al. | |

FOREIGN PATENT DOCUMENTS

| | | |
|---|---|---|
| CN | 115160311 A | 10/2022 |
| WO | 2018220149 A1 | 12/2018 |
| WO | 2019149922 A1 | 8/2019 |
| WO | 2019164945 A1 | 8/2019 |

OTHER PUBLICATIONS

Akritopoulou-Zanze et al., Synthesis of Substituted Fused Pyridines, Pyrazines and Pyrimidines by Sequential Ugi/Inverse Electron Demand Diels-Alder Transformations, Tetrahedron Letters, Jul. 10, 2009, vol. 50, pp. 5773-5776; p. 5774.
International Search Report of PCT Application No. PCT/US2020/038672, mailed Sep. 28, 2020 (3 pages).
Wang et al., "7-Oxopyrrolopyridine-derived DPP4 inhibitors-mitigation of CYP and hERG liabilities via introduction of polar functionalities in the active site", *Bioorganic & Medicinal Chemistry Letters* 21:6646-6651 (2011).

* cited by examiner

*Primary Examiner* — Adam C Milligan
*Assistant Examiner* — Elvie Grace Sellers
(74) *Attorney, Agent, or Firm* — Nielsen IP Law LLC

(57) ABSTRACT

The disclosure relates to a compound of Formula (I), which acts as an allosteric inhibitor of epidermal growth factor receptor (EGFR); pharmaceutical compositions comprising the compound; and methods of treating or preventing kinase-mediated disorders, including cancer and other proliferation diseases.

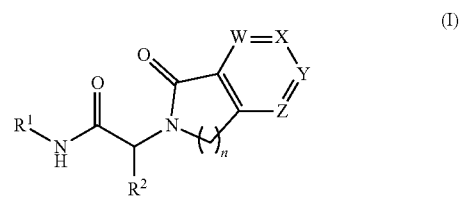

20 Claims, No Drawings

ALLOSTERIC EGFR INHIBITORS AND METHODS OF USE THEREOF

RELATED APPLICATIONS

This application claims the benefit of U.S, Provisional Application No. 62/864,899, filed on Jun. 21, 2019, and U.S. Provisional Application No. 63/007,210 filed on Apr. 8, 2020, the entire disclosures of each are hereby incorporated herein by reference.

GOVERNMENT LICENSE RIGHTS

This invention was made with government support under Grant No. R01CA201049 awarded by the National Institute of Health (NIH), The government has certain rights in the invention.

BACKGROUND

The epidermal growth factor receptor (EGFR, Erb-B1) belongs to a family of receptor tyrosine kinases that mediate the proliferation, differentiation, and survival of normal and malignant cells (Arteaga, C. L., *J. Clin. Oncol.* 19, 2001, 32-40). Deregulation of EGFR has been implicated in many types of human cancer, with overexpression of the receptor present in at least 70% of human cancers (Seymour, L. K., *Curr. Drug Targets* 2, 2001, 117-133), including non-small lung cell carcinomas, breast cancers, gliomas, squamous cell carcinomas of the head and neck, and prostate cancer (Raymond, E., et al., *Drugs* 60 (Suppl. 1), 2000, 15-23, discussion 41-2; Salomon, D. S., et al., *Crit. Rev. Oncol, Hematol.* 19, 1995, 183-232; Voldborg B. R., et al., *Ann. Oncol.* 8, 1997, 1197-1206). EGFR has, therefore, emerged as an attractive target for the design and development of diagnostic and therapeutic agents that can specifically bind and inhibit the receptor's tyrosine kinase activity and signal transduction pathway in cancer cells. For example, the EGFR tyrosine kinase (EGFR-TK) reversible inhibitor TARCEVA RTM is approved by the FDA for treatment of NSCLC and advanced pancreatic cancer, Other anti-EGFR targeted molecules have also been approved, including LAPATINIB RTM and IRESSA RTM.

Epidermal growth factor receptor (EGFR) tyrosine kinase inhibitors (TKIs) are effective clinical therapies for EGFR mutant advanced non-small cell lung cancer (NSCLC) patients (Mok, T. S., et al., *N. Engi. J. Med.* 361, 2009, 947-57; Paez, J. G., et al., *Science* 304, 2004, 1497-500; Lynch, T. J., et al., *N. Engl. J. Med.* 350, 2004, 2129-39; Rosell, R., et al., *Lancet Oncol.* 13, 2012, 239-46). Several randomized clinical trials have demonstrated that EGFR TKIs are more effective, as measured by response rate (RR) and progression free survival (PFS), than chemotherapy when used as initial systemic treatment for advanced EGFR mutant NSCLC (Mok, T. S., et al., *N. Engl. J. Med.* 361, 2009, 947-57; Rosell, R., et al., *Lancet Oncol.* 13, 2012, 239-46; Sequest, L. V. et al., *J, Clin. Oncol.* 31, 2013, 3327-34; Wu, Y. L., et al., *Lancet Oncol,* 15, 2014, 213-22; Maemondo, M., et al., *N. Engl. J. Med.* 362, 2010, 2380-8; Zhou, C., et al., *Lancet Oncol.* 12, 2011, 735-42; Mitsudomi, T., et al., *Lancet Oncol.* 11, 2010, 121-8). However, the vast majority of patients will develop disease progression following successful treatment with an EGFR TKI. The most common mechanism of acquired resistance, detected in 60%/h of patients, is a secondary mutation in EGFR at position T790 (T790M) (Yu, H. A., et al., *Clin, Cancer Res.* 19, 2013, 2240-7). This mutation leads to an increase in ATP affinity, thus making it more difficult for reversible EGFR TKIs gefitinib and erlotinib to bind the EGFR TKI domain (Yun C. H., et al., *Proc. Natl. Acad. Sci. USA* 105, 2008, 2070-5).

Covalent EGFR inhibitors have emerged for inhibiting EGFR T790M-containing cancers. However, in lung cancer patients, afatinib is only effective in EGFR TKI naïve EGFR mutant cancers and has a RR of less than 10% in patients with NSCLC that have developed resistance to gefitinib or erlotinib (Miller, V. A., et al., *Lancet Oncol.* 13, 2012, 528-38). Afatinib is a potent inhibitor of both mutant and wild type (WT) EGFR. Inhibition of WT EGFR leads to toxicities, including skin rash and diarrhea, which limits the ability to escalate afatinib doses in patients to those necessary to inhibit EGFR T790M. Irreversible pyrimidine EGFR inhibitors including the tool compound WZ4002 and clinical compounds C0-1686 and osimertinib, overcome many of the limitations of afatinib (Zhou, W., et al., *Nature* 462, 2009, 1070-4; Walter, A. 0., et al., *Cancer Discov.* 3, 2013, 1404-15; Cross, D. A. E., et al., *Cancer Discov.* 4, 2014, 1046-61). They are not only more potent on EGFR T790M, but also selectively inhibit mutant over WT EGFR and hence should lead to increased clinical efficacy and less toxicity compared with afatinib (Zhou, W., et al; Walter A. O., et al, Cross, D. A. E., et al,).

However, all current EGFR TKIs target the ATP site, and while third generation irreversible inhibitors can overcome T790M, they are all rendered impotent by the 0797S mutation, which is already arising in treated patients. Cetuximab, an anti-EGFR antibody that blocks receptor dimerization, is not effective in EGFR-mutant NSCLC because mutational activation of the kinase is effectively "downstream" of receptor dimerization. Hence, alternative strategies to inhibit EGFR are needed. At present, suitable compounds with alternative mechanisms of action targeting mutant EGFR are not available. Thus, there is a need for novel and potent small molecule EGFR inhibitors with alternative mechanisms of action targeting mutant EGFR.

SUMMARY

Provided herein are compounds of Formula (I):

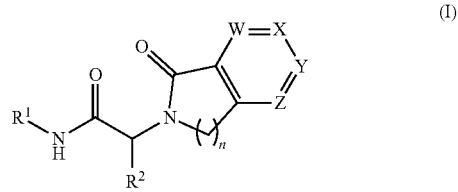

(I)

or a pharmaceutically acceptable salt or prodrug thereof, wherein:

$R^1$ is aryl or 5- to 6-membered heteroaryl;

$R^2$ is phenyl or pyridinyl, wherein the phenyl or pyridinyl is optionally substituted one or two times, independently, with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_p$OH, $S(O)_q$H, $S(O)_q$$NH_2$, or CN;

W and Z are each independently N, CH, CF, or C-($C_1$-$C_3$ alkyl);

X and Y are each independently N, CH, or $CR^3$;

provided that at least one of VV, X, Y, or Z is N, and provided that at least one of W, X, Y, or Z is CH or $CR^3$;

$R^3$, for each occurrence, is halogen, $OR^4$, $NR^4R^4$, $SO_2R^4$, $SO_2NHR^4$, $NHSO_2R^4$, $C(O)$ $OR^4$, $C(O)NHR^4$, $C(O)R^4$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkenyl, $C_6$-$C_{10}$ aryl, 5- to 6-membered heteroaryl, or 5- to 7-membered heterocyclyl, wherein the alkyl, alkenyl, or alkynyl are each optionally substituted one, two, or three times with $R^4$, and wherein the aryl, heteroaryl, or heterocyclyl are each optionally substituted one, two, or three times with $R^5$;

$R^4$, for each occurrence, is independently H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5- to 6-membered heteroaryl), or $(OH_2)_{0-3}$-(5- to 7-membered heterocyclyl), wherein the aryl, heteroaryl, or heterocyclyl are each optionally substituted one, two, or three times with $R^5$;

$R^5$, for each occurrence, is independently $C_1$-$C_5$ alkyl, $C_1$-$C_6$ haloalkyl, $C_1$-$C_6$ alkoxy, $C_1$-$C_6$ haloalkoxy, halogen, COOH, $C(O)O(C_1$-$C_6$ alkyl), $O(CH_2)_{1-3}$—OH, $NH_2$, OH, CN, $(CH_2)_{0-3}$—($C_6$-$C_{10}$ aryl), $(CH_2)_{0-3}$-(5- to 6-membered heteroaryl), or $(CH_2)_{0-3}$-(5- to 7-membered heterocyclyl), wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_6$ haloalkoxy, halogen, $NH_2$, $NH(C_1$-$C_6$ alkyl), $N(C_1$-$C_6$ alkyl)$_2$, $SO_2NH_2$, $(CH_2)_{1-2}$—OH, $C(O)$ $(CH_2)_{1-2}$—OH, and $O(O)O(C_1$-$C_6$ alkyl);

n is 1 or 2;
p is 1, 2, 3, or 4; and
q is 0, 1, or 2.

In one embodiment, $R^1$ is thiazolyl or pyridinyl. In another embodiment, $R^2$ is phenyl substituted with halogen. In another embodiment, $R^2$ is phenyl substituted one or two times, independently, with halogen or OH. In another embodiment, n is 1 and X is $CR^3$. In another embodiment, n is 2 and Y is $CR^3$. In another embodiment, n is 1 and Y is $CR^3$. In another embodiment, n is 2 and X is $CR^3$.

In yet another embodiment, $R^3$ is:

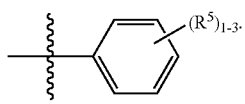

In a further embodiment, $R^5$, for each occurrence, is independently 5- to 7-membered heterocyclyl, wherein the heterocyclyl is optionally substituted with one or more substituents independently selected from $C_1$-$C_6$ alkyl, $C_1$-$C_6$ haloalkyl, $C_1$-$C_6$ alkoxy, and $C_1$-$C_6$ haloalkoxy.

In yet another embodiment, $R^3$ is selected from:

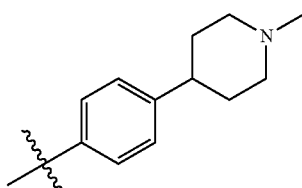

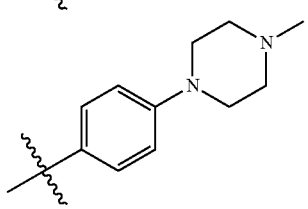

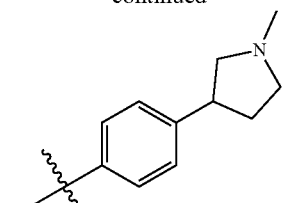

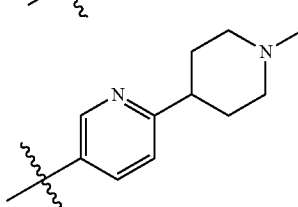

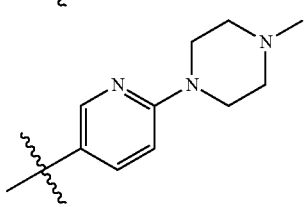

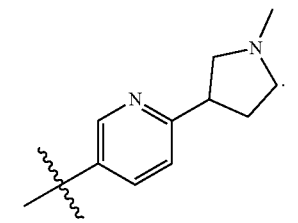

In a further embodiment, $R^5$, for each occurrence, is independently halogen or 5- to 7-membered heterocyclyl, wherein the heterocyclyl is optionally substituted with one or more substituents independently selected from $C_1$-$C_6$ alkyl, $C_1$-$C_6$ haloalkyl, $C_1$-$C_6$ alkoxy, and $C_1$-$C_6$ haloalkoxy.

In yet another embodiment, $R^3$ is selected from:

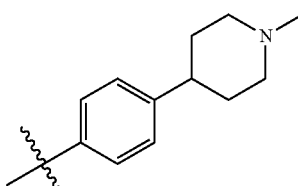

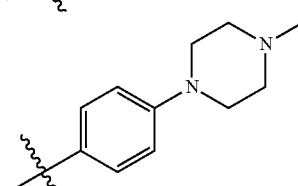

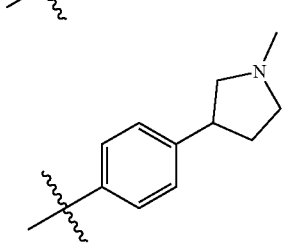

-continued

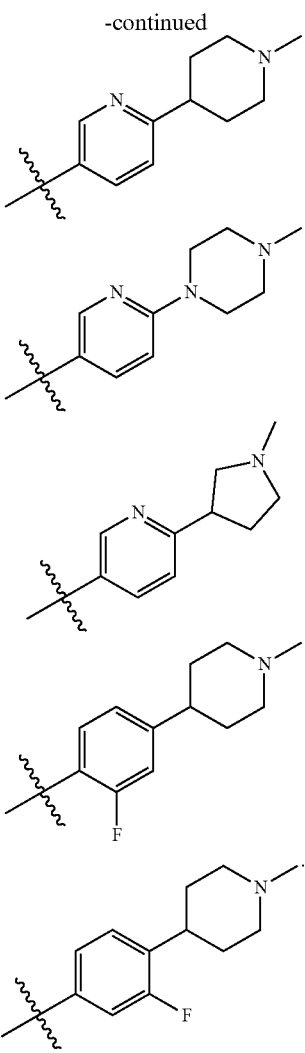

In a further embodiment, the disclosure provides a compound as exemplified in Table 2.

The disclosure also provides a pharmaceutical composition comprising a compound of Formula (I), and a pharmaceutically acceptable carrier. In one embodiment, the pharmaceutical composition further comprises a second agent, wherein said second agent prevents EGFR dimer formation in a subject. In further embodiments, the second agent is selected from the group consisting of cetuximab, trastuzumab, and panitumumab. In yet another embodiment, the pharmaceutical composition further comprises a second agent, wherein said second agent is an ATP-competitive EGFR inhibitor. In a further embodiment, the ATP-competitive EGFR inhibitor is osimertinib.

The disclosure also provides a method of inhibiting a kinase comprising administering to a subject in need thereof an effective amount of a compound of Formula (I) or a pharmaceutical composition comprising a compound of Formula (I) and a pharmaceutically acceptable carrier. In one embodiment, the kinase to be inhibited is epidermal growth factor receptor (EGFR). In a further embodiment, the EGFR to be inhibited contains one or more mutations. In yet a further embodiment, the EGFR to be inhibited contains one or more mutations selected from the group consisting of T790M, L718Q, L844V, V948R, L858R, I941R, C797S, and Del. In another embodiment, the compound of Formula (I) exhibits at least 5-fold greater inhibition of EGFR containing one or more mutations relative to wild-type EGFR. In another embodiment, the method further comprises administering to the subject a second agent, wherein said second agent prevents EGFR dimer formation in the subject. In another embodiment, the method further comprises administering to the subject a second agent, wherein said second agent is an ATP-competitive EGFR inhibitor. In a further embodiment, the ATP-competitive inhibitor is osimertinib. In another embodiment, the subject is a human.

The disclosure also provides a method of treating or preventing a kinase-mediated disorder, comprising administering to a subject in need thereof an effective amount of a compound of Formula (I) or a pharmaceutical composition comprising a compound of Formula (I) and a pharmaceutically acceptable carrier. In one embodiment, the kinase-mediated disorder is resistant to an EGFR-targeted therapy. In some embodiments, the EGFR-treated therapy is selected from the group consisting of gefitinib, erlotinib, osimertinib, CO-1686, and WZ4002, In one embodiment, the method further comprises administering to the subject a second agent, wherein said second agent prevents EGFR dimer formation in the subject. In other embodiments, the method further comprises administering to the subject a second agent, wherein said second agent is an ATP-competitive EGFR inhibitor. In a further embodiment, the ATP-competitive inhibitor is osimertinib. In another embodiment, the subject is a human.

The disclosure also provides a method of treating or preventing cancer or a proliferation disease, comprising administering to a subject in need thereof an effective amount of a compound of Formula (I) or a pharmaceutical composition comprising a compound of Formula (I) and a pharmaceutically acceptable carrier. In one embodiment, the cancer is lung cancer, breast cancer, glioma, squamous cell carcinoma, or prostate cancer. In another embodiment, the method further comprises administering to the subject a second agent, wherein said second agent prevents EGFR dimer formation in the subject. In another embodiment, the method further comprises administering to the subject a second agent, wherein said second agent is an ATP-competitive EGFR inhibitor. In a further embodiment, the ATP-competitive inhibitor is osimertinib. In another embodiment, the subject is a human.

The disclosure also provides a kit comprising a compound capable of inhibiting EGFR activity selected from a compound of Formula (I), or a pharmaceutically acceptable salt thereof, and instructions for use in treating cancer. In one embodiment, the kit further comprises components for performing a test to determine whether a subject has an activating mutation in EGFR or a resistance mutation in EGFR. In another embodiment, the kit further comprises a second agent, wherein said second agent prevents EGFR dimer formation in a subject. In another embodiment, the method further comprises administering to the subject a second agent, wherein said second agent is an ATP-competitive EGFR inhibitor. In a further embodiment, the ATP-competitive inhibitor is osimertinib.

The disclosure also relates to a prodrug of a compound of Formula (I),

DETAILED DESCRIPTION

Definitions

Listed below are definitions of various terms used to describe this invention. These definitions apply to the terms as they are used throughout this specification and claims, unless otherwise limited in specific instances, either individually or as part of a larger group. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting. As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the provision of a therapeutic agent to a subject. Multiple techniques of administering a therapeutic agent exist in the art including, but not limited to, intravenous, oral, aerosol, parenteral, ophthalmic, pulmonary, and topical administration.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "treat," "treated," "treating," or "treatment" includes the diminishment or alleviation of at least one symptom associated or caused by the state, disorder, or disease being treated. In certain embodiments, the treatment comprises bringing into contact with wild-type or mutant EGFR an effective amount of a compound of the invention for conditions related to cancer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "prodrug" refers to a precursor compound that will undergo metabolic activation in vivo to produce an active drug. Thus, for example, a prodrug of a compound of Formula (I) will, when administered to a subject, undergo metabolic activation to generate the compound of Formula (I).

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the disclosure and a co-agent, are both administered to a patient simultaneously in the form of a single entity or dosage. The term "non-fixed combination" means that the active ingredients, e.g., a compound of the disclosure and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example, in Remington's Pharmaceutical Sciences (Genaro, Ed., Mack Publishing Co., 1985, Easton, PA), which is incorporated herein by reference.

An "oral dosage form" includes a unit dosage form prescribed or intended for oral administration. In an embodiment of the pharmaceutical combinations provided herein, the HDAC6 inhibitor (e.g., Compounds A or B) is administered as an oral dosage form.

As used herein, the term "EGFR" refers to epidermal growth factor receptor (alternately referred to as ErbB-1 or HER1) and may refer to the wild-type receptor or to a receptor containing one or more mutations.

As used herein, the term "HER" or "Her" refers to members of the ErbB receptor tyrosine kinase family, including EGFR, ERBB2, HER3, and HER4.

As used herein, the term "allosteric site" refers to a site on EGFR other than the ATP binding site, such as that characterized in a crystal structure of EGFR, An "allosteric site" can be a site that is close to the ATP binding site, such as that characterized in a crystal structure of EGFR. For example, one allosteric site includes one or more of the following amino acid residues of epidermal growth factor receptor (EGFR): Lys745, Leu788, Ala743, Cys755, Leu777, Phe856, Asp855, Met766, Ile759, Glu762, and/or Ala763.

As used herein, the term "agent that prevents EGFR dimer formation," or iterations thereof, refers to an agent that prevents dimer formation in which the C-lobe of the "activator" subunit impinges on the N-lobe of the "receiver" subunit, Examples of agents that prevent EGFR dimer formation include, but are not limited to, cetuximab, cobimetinib, trastuzumab, panitumumab, and Mig6.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$alkyl include ethyl, methyl, isopropyl, isobutyl, n-pentyl, and n-hexyl.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "haloalkoxy" refers to the group —O-haloalkyl, wherein haloalkyl is as defined herein. Haloalkoxy includes, by way of example, chloromethoxy, trifluoromethoxy, bromoethoxy, chlorofluoroethoxy, and the like.

As used herein, the term "alkenyl" refers to a monovalent group derived from a hydrocarbon moiety containing, in certain embodiments, from two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term "alkynyl" refers to a monovalent group derived from a hydrocarbon moiety containing, in certain embodiments, from two to six, or two to eight carbon atoms having at least one carbon-carbon triple bond. The alkynyl group may or may not be the point of attachment to another group. The term "alkynyl" includes, but is not limited to, ethynyl, 1-propynyl, 1-butynyl, heptynyl, octynyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1] heptanyl, 2-azabicyclo[2.2.1]heptanyl, 3-azabicyclo[3.1.1]heptanyl, 2-azabicyclo[3.1.1]heptanyl, 3-azabicyclo[3,1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2,1]heptanyl, 6-oxa-3-azabicyclo[3,1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl.

As used herein, the term "aromatic" refers to a carbocycle or heterocycle with one or more polyunsaturated rings and having aromatic character, i.e., having (4n +2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. If the rings are fused, one of the rings must be fully unsaturated and the fused ring(s) may be fully saturated, partially unsaturated or fully unsaturated. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-41-1-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds of the Disclosure

Provided herein are compounds that are allosteric inhibitors of epidermal growth factor receptor (EGFR) useful in the treatment of kinase-mediated disorders, including cancer and other proliferation diseases.

A first aspect of the disclosure relates to compounds of Formula (I):

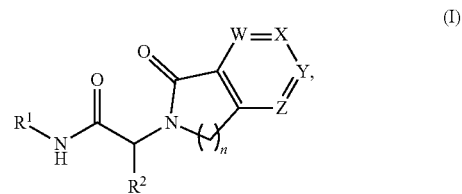

or a pharmaceutically acceptable salt or prodrug thereof, wherein:

$R^1$ is aryl or 5- to 6-membered heteroaryl;

$R^2$ is phenyl or pyridinyl, wherein the phenyl or pyridinyl is optionally substituted one or two times, independently, with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_pOH$, $S(O)_qH$, $S(O)_qNH_2$, or CN;

W and Z are each independently N, CH, CF, or C—($C_1$-$C_3$ alkyl);

X and Y are each independently N, CH, or $CR^3$;

provided that at least one of VV, X, Y, or Z is N, and provided that at least one of W, X, Y, or Z is CH or $CR^3$;

$R^3$, for each occurrence, is independently halogen, $OR^4$, $NR^4R^4$, $SO_2R^4$, $SO_2NHR^4$, $NHSO_2R^4$, C(O) $OR^4$, C(O) $NHR^4$, C(O)$R^4$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkenyl, $C_6$-$C_{10}$ aryl, 5- to 6-membered heteroaryl, or 5- to 7-membered heterocyclyl, wherein the alkyl, alkenyl, or alkynyl are each optionally substituted one, two, or three times with $R^4$, and wherein the aryl, heteroaryl, or heterocyclyl are each optionally substituted one, two, or three times with $R^5$;

$R^4$, for each occurrence, is independently H, $(CH_2)_{0-3}$—$(C_3$-$C_7$ cycloalkyl), $(C1^-17)_{0-3}$—$(C_4$-$C_7$ cycloalkenyl), $(CH_2)_{0-3}$—$(C_6$-$C_{10}$ aryl), $(CH_2)C_{0-3}$-(5- to 6-membered heteroaryl), or $(CH_2)C_{0-3}$-(5- to 7-membered heterocyclyl), wherein the aryl, heteroaryl, or heterocyclyl are each optionally substituted one, two, or three times with $R^5$;

$R^5$, for each occurrence, is independently $C_1$-$C_5$ alkyl, $C_1$-$C_6$ haloalkyl, $C_1$-$C_6$ alkoxy, $C_1$-$C_6$ haloalkoxy, halogen, COOH, O(O)O($C_1$-$C_6$ alkyl), O($CH_2)_{1-3}$—OH, $NH_2$, OH, CN, $(CH_2)_{0-3}$—$(C_6$-$C_{10}$ aryl), $(OH2)O$-3-(5- to 6-membered heteroaryl), or $(CH_2)C\_3$-(5- to 7-membered heterocyclyl), wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, $NH(C_1$-$C_6$ alkyl), $N(C_1$-$C_6$ alkyl)$_2$, $SO_2NH_2$, $(CH_2)_{1-2}$—OH, C(O) $(OH_2)_{1-2}$—OH, and O(O)O($C_1$-$C_6$ alkyl):

n is 1 or 2;
p is 1, 2, 3, or 4; and
q is 0, 1, or 2.

In some embodiments of Formula (I), $R^1$ is phenyl, (uranyl, thienyl, thiazolyl, pyridinyl, pyridazinyl, pyrimidinyl, or pyrazinyl.

In some embodiments of Formula (I), $R^1$ is thiazolyl or pyridinyl.

In some embodiments of Formula (I), $R^1$ is thiazolyl.

In some embodiments of Formula (I), $R^1$ is pyridinyl.

In some embodiments of Formula (I), $R^2$ is phenyl optionally substituted one or two times, independently, with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_pOH$, $S(O)_qH$, $S(O)_1NH_2$, or CN.

In some embodiments of Formula (I), $R^2$ is halophenyl optionally substituted one time with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_pOH$, $S(O)_qH$, $S(O)_qNH_2$, or CN.

In some embodiments of Formula (I), $R^2$ is hydroxyphenyl optionally substituted one time with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_pOH$, $S(O)_qH$, $S(O)_qNH_2$, or CN.

In some embodiments of Formula (I), $R^2$ is fluorophenyl optionally substituted one time with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_pOH$, $S(O)_qH$, $S(O)_qNh_2$, or CN.

In some embodiments of Formula (I), $R^2$ is phenyl substituted one or two times, independently, with halogen or OH.

In some embodiments of Formula (I), $R^2$ is halophenyl.
In some embodiments of Formula (I), $R^2$ is fluorophenyl.
In some embodiments of Formula (I), $R^2$ is m-fluorophenyl.
In some embodiments of Formula (I), $R^2$ is halohydroxyphenyl.
In some embodiments of Formula (I), $R^2$ is fluorohydroxyphenyl.
In some embodiments of Formula (I), $R^2$ is:

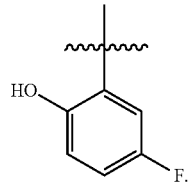

In some embodiments of Formula (I), W is N.
In some embodiments of Formula (I), W is CH.
In some embodiments of Formula (I), W is CF,
In some embodiments of Formula (I), W is $CCH_3$.
In some embodiments of Formula (I), X is N.
In some embodiments of Formula (I), X is CH.
In some embodiments of Formula (I), X is $CR^3$.
In some embodiments of Formula (I), Y is N.
In some embodiments of Formula (I), Y is CH.
In some embodiments of Formula (I), Y is $CR^3$.
In some embodiments of Formula (I), Z is N.
In some embodiments of Formula (I), Z is CH.
In some embodiments of Formula (I), Z is CF.
In some embodiments of Formula (I), Z is $CCH_3$.
In some embodiments of Formula (I), W is N, X is $CR^3$, Y is CH, and Z is CH.

In some embodiments of Formula (I), W is CH, X is $CR^3$, Y is N, and Z is CH.
In some embodiments of Formula (I), W is CH, X is $CR^3$, Y is CH, and Z is N.
In some embodiments of Formula (I), W is N, X is CH, Y is $CR^3$, and Z is CH.
In some embodiments of Formula (I), W is CH, X is N, Y is $CR^3$, and Z is CH.
In some embodiments of Formula (I), 1t1(is CH, X is CH, Y is $CR^3$, and Z is N.
In some embodiments of Formula (I), W is CH, X is N, Y is $CR^3$, and Z is N.
In some embodiments of Formula (I), W is N, X is $CR^3$, Y is N, and Z is CH.
In some embodiments of Formula (I), if X is $CR^3$, then Y is CH.
In some embodiments of Formula (I), if Y is $CR^3$, then X is CH.
In some embodiments of Formula (I), if X is $CR^3$, then Y is N.
In some embodiments of Formula (I), if Y is $CR^3$, then X is N.

In some embodiments of Formula (I), $R^3$, for each occurrence, is independently $C_6$-$C_{10}$ aryl, 5- to 6-membered heteroaryl, or 5- to 7-membered heterocyclyl, wherein the aryl, heteroaryl, or heterocyclyl are each optionally substituted one, two, or three times with $R^5$.

In some embodiments of Formula (I), $R^3$, for each occurrence, is independently phenyl or pyridinyl, wherein the phenyl or pyridinyl are each optionally substituted one, two or three times with $R^5$.

In some embodiments of Formula (I), $R^3$, for each occurrence, is independently phenyl optionally substituted one, two or three times with $R^5$.

In some embodiments of Formula (I), $R^3$, for each occurrence, is independently pyridinyl optionally substituted one, two or three times with $R^5$.

In some embodiments of Formula (I), $R^3$, for each occurrence, is independently selected from:

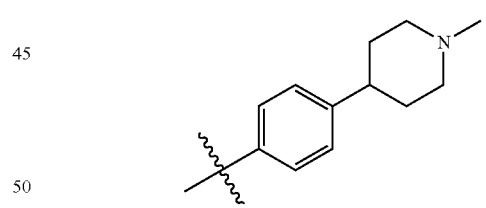

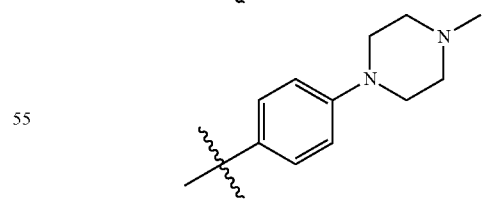

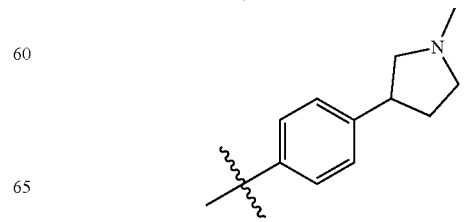

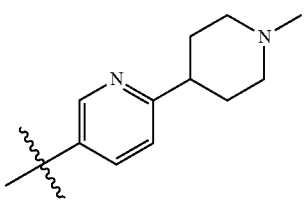

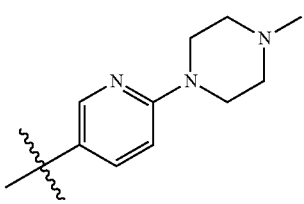

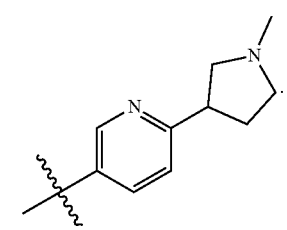

In some embodiments of Formula (I), R³, for each occurrence, is independently selected from:

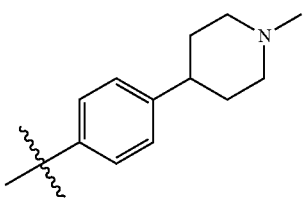

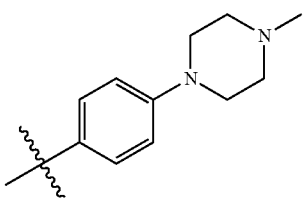

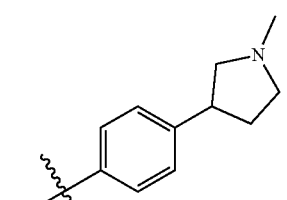

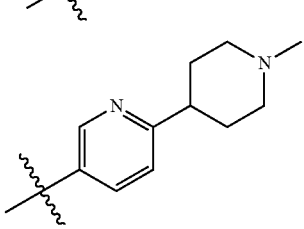

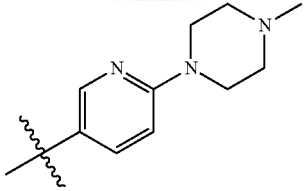

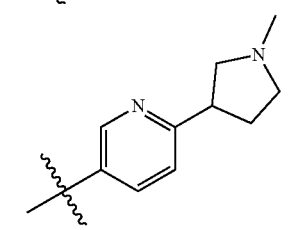

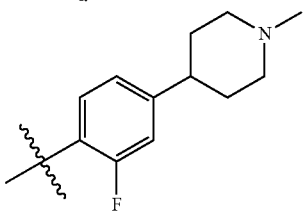

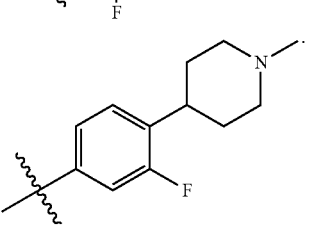

In some embodiments of Formula (I), R³, for each occurrence, is independently OR⁴, NR⁴R⁴, SO₂R⁴, SO₂NHR⁴, NHSO₂R⁴, C(O) OR⁴, C(O)NHR⁴, C(O) R⁴, C₁-C₆ alkyl, C₂-C₆ alkenyl, or C₂-C₆ alkynyl, wherein the alkyl, alkenyl, or alkynyl are each optionally substituted one, two, or three times with R⁴.

In some embodiments of Formula (I), R³, for each occurrence, is independently OR⁴, NR⁴R⁴, SO₂NHR⁴, NHSO₂R⁴, C(O)NHR⁴, or C₂-C₆ alkynyl, wherein the alkynyl is optionally substituted one time with R⁴.

In some embodiments of Formula (I), R⁴, for each occurrence, is independently H, C₃-cycloalkyl, C₄-C₇ cycloalkenyl, C₆-C₁₀ aryl, 5- to 6-membered heteroaryl, or 5- to 7-membered heterocyclyl, wherein the aryl, heteroaryl, or heterocyclyl are each optionally substituted one, two, or three times with R⁵.

In some embodiments of Formula (I), R⁴, for each occurrence, is independently H, C6-C10 aryl, 5- to 6-membered heteroaryl, or 5- to 7-membered heterocyclyl, wherein the aryl, heteroaryl, or heterocyclyl are each optionally substituted one, two, or three times with R⁵.

In some embodiments of Formula (I), R⁴, for each occurrence, is independently H, phenyl, or pyridinyl, wherein the phenyl or pyridinyl are each optionally substituted one, two, or three times with R⁵.

In some embodiments of Formula (I), R⁴ is H.

In some embodiments of Formula (I), R⁴ is phenyl optionally substituted one, two or three times with R⁵.

In some embodiments of Formula (I), R⁴ is pyridinyl optionally substituted one, two or three times with R⁵.

In some embodiments of Formula (I), R⁵, for each occurrence, is independently C₁-C₆ alkyl, halogen, (CH₂)₀₋₃— (C₆-C₁₀ aryl), (CH₂)₀₋₃-(5- to 6-membered heteroaryl), or (CH$_2$)$_{0-3}$-(5- to 7-membered heterocyclyl), wherein the aryl, heteroaryl, or heterocyclyl is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, halogen, NH$_2$, NH(C$_1$-C$_6$ alkyl), N(C$_1$-C$_6$ alkyl)$_2$, SO$_2$NH$_2$, (CH$_2$)$_{1-2}$—OH, C(O)(CH$_2$)$_{1-2}$—OH, and C(O)O(C$_1$-C$_6$ alkyl).

In some embodiments of Formula (I), R$^5$, for each occurrence, is independently C$_1$-C$_6$ alkyl, C$_6$-C$_{10}$ aryl, 5- to 6-membered heteroaryl, or 5- to 7-membered heterocyclyl, wherein the aryl, heteroaryl, or heterocyclyl is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, halogen, NH$_2$, NH(C$_1$-C$_6$ alkyl), N(C$_1$-C$_6$ alkyl)$_2$, SO$_2$NH$_2$, (CH$_2$)$_{1-2}$—OH, C(O) (CH$_2$)$_{1-2}$—OH, and C(O)O(C$_1$-C$_6$ alkyl).

In some embodiments of Formula (I), R$^5$, for each occurrence, is independently 5- to 7-membered heterocyclyl optionally substituted with one or more substituents independently selected from C$_1$-C$_6$ alkyl, C$_1$-C$_6$haloalkyl, C$_1$-C$_6$alkoxy, C$_1$-C$_6$ haloalkoxy.

In some embodiments of Formula (I), R$^5$, for each occurrence, is independently halogen or 5- to 7-membered heterocyclyl, wherein the heterocycle is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy.

In some embodiments of Formula (I), R$^5$, for each occurrence, is independently 5- to 7-membered heterocyclyl optionally substituted with one or more C$_1$-C$_6$ alkyl.

In some embodiments of Formula (I), R$^5$, for each occurrence, is independently halogen or 5- to 7-membered heterocyclyl, wherein the heterocycle is optionally substituted with one or more C$_1$-C$_6$ alkyl.

In some embodiments of Formula (I), R$^5$, for each occurrence, is independently 5- to 7-membered heterocyclyl optionally substituted with one or more methyl.

In some embodiments of Formula (I), R$^5$, for each occurrence, is independently fluoro or 5- to 7-membered heterocyclyl, wherein the heterocycle is optionally substituted with one or more methyl.

In some embodiments of Formula (I), n is 1.

In some embodiments of Formula (I), n is 2.

In some embodiments of Formula (I), R$^1$ is thiazolyl and R$^2$ is fluorophenyl.

In some embodiments of Formula (I), R$^1$ is pyridinyl and R$^2$ is fluorophenyl.

In some embodiments of Formula (I), n is 1 and X is CR$^3$.

In some embodiments of Formula (I), n is 1, X is CR$^3$, and R$^3$ is phenyl or pyridinyl, wherein the phenyl or pyridinyl are each optionally substituted one, two or three times with R$^5$.

In some embodiments of Formula (I), n is 1 and Y is CR$^3$.

In some embodiments of Formula (I), n is 1, Y is CR$^3$, and R$^3$ is phenyl or pyridinyl, wherein the phenyl or pyridinyl are each optionally substituted one, two or three times with R$^5$.

In some embodiments of Formula (I), n is 1, Y is CR$^3$, and R$^3$ is OR$^4$, NR$^4$R$^4$, SO$_2$NHR$^4$, NHSO$_2$R$^4$, C(O)NHR$^4$, or C$_2$-C$_6$alkynyl, wherein the alkynyl is optionally substituted one time with R$^4$.

In some embodiments of Formula (I), n is 1; Y is CR$^3$; R$^3$ is NR$^4$R$^4$; and R$^4$, for each occurrence, is independently H, phenyl, or pyridinyl, wherein the phenyl or pyridinyl are each optionally substituted one, two or three times with R$^5$.

In some embodiments of Formula (I), n is 2 and X is CR$^3$.

In some embodiments of Formula (I), n is 2, X is CR$^3$, and R$^3$ is phenyl or pyridinyl, wherein the phenyl or pyridinyl are each optionally substituted one, two or three times with R$^5$.

In some embodiments of Formula (I), n is 2 and Y is CR$^3$.

In some embodiments of Formula (I), n is 2, Y is CR$^3$, and R$^3$ is phenyl or pyridinyl, wherein the phenyl or pyridinyl are each optionally substituted one, two or three times with R$^5$.

In some embodiments, the disclosure relates to compounds of Formula (II):

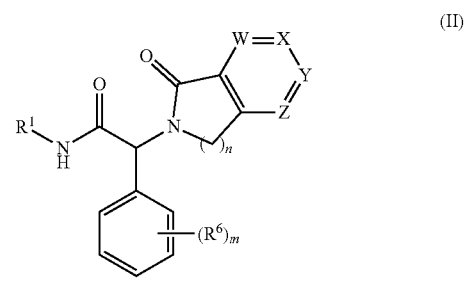

(II)

or a pharmaceutically acceptable salt or prodrug thereof, wherein:

R$^1$ is aryl or 5- to 6-membered heteroaryl;

W and Z are each independently N, CH, CF, or C-(C$_1$-C$_3$ alkyl);

X and Y are each independently N. CH, or CR$^3$;

provided that at least one of W, X, Y, or Z is N, and provided that at least one of W, X, Y, or Z is CH or CR$^3$;

R$^3$, for each occurrence, is halogen, OR$^4$, NR$^4$R$^4$, SO$_2$R$^4$, SO$_2$NHR$^4$, NHSO$_2$R$^4$, C(O)OR$^4$, C(O)NHR$^4$, C(O)R$^4$, C$_1$-C$_6$alkyl, C$_2$-C$_6$ alkenyl, C$_2$-C$_6$alkynyl, C$_3$-C$_7$ cycloalkyl, C$_4$-C$_7$ cycloalkenyl, C$_6$-C$_{10}$ aryl, 5- to 6-membered heteroaryl, or 5- to 7-membered heterocyclyl, wherein the alkyl, alkenyl, or alkynyl are each optionally substituted one time with R$^4$; and wherein the aryl, heteroaryl, or heterocyclyl are each optionally substituted one, two, or three times with R$^5$;

R$^4$, for each occurrence, is independently H, C$_3$-C$_7$ cycloalkyl, C$_4$-C$_7$ cycloalkenyl, C$_6$-C$_{10}$ aryl, 5- to 6-membered heteroaryl, or 5- to 7-membered heterocyclyl wherein the aryl, heteroaryl, or heterocyclyl are each optionally substituted one, two, or three times with R$^5$;

R$^5$, for each occurrence, is independently C$_1$-C$_6$ alkyl, C$_1$-C$_6$ haloalkyl, C$_1$-C$_6$ alkoxy, C$_1$-C$_6$ haloalkoxy, halogen. COOH, C(O)O(C$_1$-C$_6$ alkyl), NH$_2$, OH, CN, (CH$_2$)$_{0-3}$-(C$_6$-C$_{10}$ aryl), (CH$_2$)$_{0-3}$-(5- to 6-membered heteroaryl), or (CH$_2$)$_{0-3}$-(5- to 7-membered heterocyclyl), wherein the aryl, heteroaryl, or heterocyclyl is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, halogen, NH$_2$, NH(C$_1$-C$_6$ alkyl), N(C$_1$-C$_6$ alkyl)$_2$, SO$_2$NH$_2$, (CH$_2$)$_{1-2}$—OH, C(O)(CH$_2$)$_{1-2}$—OH, and C(O)O(C$_1$-C$_6$ alkyl);

R$^6$ for each occurrence, is independently C$_1$-C$_3$ alkyl, C$_1$-C$_3$ haloalkyl, C$_1$-C$_3$ alkoxy, C$_1$-C$_3$ haloalkoxy, halogen, OH, NO$_2$, NH$_2$, (CH$_2$)$_p$OH, S(O)$_q$H, S(O)$_p$NH$_2$, or CN;

n is 1 or 2;

m is 1 or 2;

p is 1, 2, 3, or 4; and q is 0, 1, or 2.

In some embodiments of Formula (II), R¹ is thiazolyl or pyridinyl.
In some embodiments of Formula (II), R¹ is thiazolyl.
In some embodiments of Formula (II), R¹ is pyridinyl.
In some embodiments of Formula (II), W is N.
In some embodiments of Formula (II), W is CH.
In some embodiments of Formula (II), W is CF.
In some embodiments of Formula (II), W is CCH₃.
In some embodiments of Formula (II), X is N.
In some embodiments of Formula (II), X is CH.
In some embodiments of Formula (II), X is CR³.
In some embodiments of Formula (II), Y is N.
In some embodiments of Formula (II), Y is CH.
In some embodiments of Formula (II), Y is CR³.
In some embodiments of Formula (II), Z is N.
In some embodiments of Formula (II), Z is CH.
In some embodiments of Formula (II), Z is CF.
In some embodiments of Formula (II), Z is CCH₃.
In some embodiments of Formula (II), W is N, X is CR³, Y is CH, and Z is CH.
In some embodiments of Formula (II), W is CH, X is CR³, Y is N, and Z is CH.
In some embodiments of Formula (II), W is CH, X is CR³, Y is CH, and Z is N.
In some embodiments of Formula (II), W is N, X is CH, Y is CR³, and Z is CH.
In some embodiments of Formula (II), W is CH, X is N, Y is CR³, and Z is CH.
In some embodiments of Formula (II), W is CH, X is CH, Y is CR³, and Z is N.
In some embodiments of Formula (II), W is CH, X is N, Y is CR³, and Z is N.
In some embodiments of Formula (II), W is N, X is CR³, Y is N, and Z is CH.
In some embodiments of Formula (II), if X is CR³, then Y is CH.
In some embodiments of Formula (II), if Y is CR³, then X is CH.
In some embodiments of Formula (II), if X is CR³, then Y is N.
In some embodiments of Formula (II), if Y is CR³, then X is N.

In some embodiments of Formula (II), R³, for each occurrence, is independently $C_6$-$C_{10}$ aryl, 5- to 6-membered heteroaryl, or 5- to 7-membered heterocyclyl, wherein the aryl, heteroaryl, or heterocyclyl are each optionally substituted one, two, or three times with R⁵.

In some embodiments of Formula (II), R³, for each occurrence, is independently phenyl or pyridinyl, wherein the phenyl or pyridinyl are each optionally substituted one, two or three times with R⁵.

In some embodiments of Formula (II), R³, for each occurrence, is independently phenyl optionally substituted one, two or three times with R⁵.

In some embodiments of Formula (II), R³, for each occurrence, is independently pyridinyl optionally substituted one, two or three times with R⁵.

In some embodiments of Formula (II), R³, for each occurrence, is independently selected from:

In some embodiments of Formula (II), R³, for each occurrence, is independently selected from:

-continued

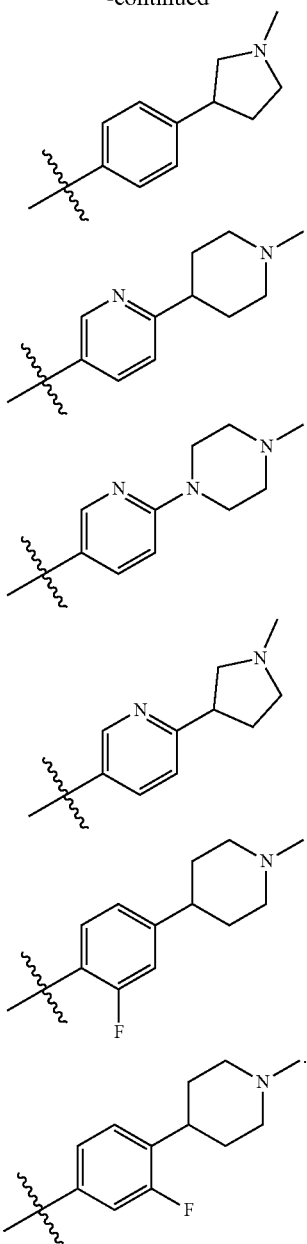

In some embodiments of Formula (II), $R^3$, for each occurrence, is independently $OR^4$, $NR^4R^4$, $SO_2NHR^4$, $NHSO_2R^4$, $C(O)NHR^4$, $C_1$-$C_6$ alkyl, $C_2$-$C_6$ alkenyl, or $O2$-$Cs$ alkynyl, wherein the alkyl, alkenyl, or alkynyl are each optionally substituted one time with $R^4$.

In some embodiments of Formula (I), $R^4$, for each occurrence, is independently H, $C_6$-$C_{10}$ aryl, 5- to 6-membered heteroaryl, or 5- to 7-membered heterocyclyl, wherein the aryl, heteroaryl, or heterocyclyl are each optionally substituted one, two, or three times with $R^5$.

In some embodiments of Formula (II), $R^4$, for each occurrence, is independently H, phenyl, or pyridinyl, wherein the phenyl or pyridinyl are each optionally substituted one, two, or three times with $R^5$.

In some embodiments of Formula (II), $R^4$ is H.

In some embodiments of Formula (II), $R^4$ is phenyl optionally substituted one, two or three times with $R^5$.

In some embodiments of Formula (II), $R^4$ is pyridinyl optionally substituted one, two or three times with $R^5$.

In some embodiments of Formula (II), $R^5$, for each occurrence, is independently $C_1$-$C_6$ alkyl, halogen, $(CH_2)_{0-3}$-$(C_6$-$C_{10}$ aryl), $(CH_2)_{0-3}$-(5- to 6-membered heteroaryl), or $(CH_2)_{0-3}$-(5- to 7-membered heterocyclyl), wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, $NH(C_1$-$C_6$ alkyl), $N(C_1$-$C_6$ alky)$_2$, $SO_2NH_2$, $(CH_2)_{1-2}$—OH, $C(O)(CH_2)_{1-2}$—OH, and $C(O)O(C_1$-$C_6$ alkyl).

In some embodiments of Formula (II), $R^5$, for each occurrence, is independently $C_1$-$C_6$ alkyl, $C_6$-$C_{10}$ aryl, 5- to 6-membered heteroaryl, or 5- to 7-membered heterocyclyl, wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, $NH(C_1$-$C_6$ alkyl), $N(C_1$-$C_6$ alkyl)$_2$, $SO_2NH_2$, $(CH_2)_{1-2}$—OH, $C(O)$ $(CH_2)_{1-2}$—OH, and $C(O)O(C_1$-$C_6$ alkyl).

In some embodiments of Formula (II), $R^5$, for each occurrence, is independently 5- to 7-membered heterocyclyl optionally substituted with one or more substituents independently selected from $C_1$-$C_6$ alkyl, $C$,-$C_6$ haloalkyl, $C$,-$C_6$ alkoxy, $C_f$-$C_B$ haloalkoxy. In some embodiments of Formula (II), $R^5$, for each occurrence, is independently halogen or 5- to 7-membered heterocyclyl, wherein the heterocycle is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, In some embodiments of Formula (II), $R^5$, for each occurrence, is independently 5- to 7-membered heterocyclyl optionally substituted with one or more $C_1$-$C_6$ alkyl.

In some embodiments of Formula (II), $R^5$, for each occurrence, is independently halogen or 5- to 7-membered heterocyclyl, wherein the heterocycle is optionally substituted with one or more $C_1$-$C_6$ alkyl.

In some embodiments of Formula (II), $R^5$, for each occurrence, is independently 5- to 7-membered heterocyclyl optionally substituted with one or more methyl.

In some embodiments of Formula (II), $R^5$, for each occurrence, is independently fluoro or 5- to 7-membered heterocyclyl, wherein the heterocycle is optionally substituted with one or more methyl.

In some embodiments of Formula (II), $R^6$, for each occurrence, is independently halogen or OH.

In some embodiments of Formula (II), $R^6$, for each occurrence, is independently halogen.

In some embodiments of Formula (II), $R^6$, for each occurrence, is independently fluoro.

In some embodiments of Formula (II), $R^6$, for each occurrence, is independently OH.

In some embodiments of Formula (II), n is 1.
In some embodiments of Formula (II), n is 2.
In some embodiments of Formula (II), m is 1.
In some embodiments of Formula (II), m is 2.
In some embodiments of Formula (II), $R^1$ is thiazolyl and $R^6$ is fluoro,
In some embodiments of Formula (II), $R^1$ is pyridinyl and $R^6$ is fluoro.
In some embodiments of Formula (II), n is 1 and X is $CR^3$.
In some embodiments of Formula (II), n is 1, Xis $CR^3$, and $R^3$ is phenyl or pyridinyl, wherein the phenyl or pyridinyl are each optionally substituted one, two or three times with $R^5$.

In some embodiments of Formula (II), n is 1 and Y is $CR^3$.

In some embodiments of Formula (II), n is 1, Y is $CR^3$, and $R^3$ is phenyl or pyridinyl, wherein the phenyl or pyridinyl are each optionally substituted one, two or three times with $R^5$.

In some embodiments of Formula (II), n is 1, Y is $CR^3$, and $R^3$ is $OR^4$, $NR^4R^4$, $SO_2NHR^4$, $NHSO_2R^4$, $C(O)NHR^4$, or $C_2$-$C_6$alkynyl, wherein the alkynyl is optionally substituted one time with $R^4$.

In some embodiments of Formula (II), n is 1; Y is $CR^3$; $R^3$ is $NR^4R^4$; and $R^4$, for each occurrence, is independently H, phenyl, or pyridinyl, wherein the phenyl or pyridinyl are each optionally substituted one, two, or three times with $R^5$.

In some embodiments of Formula (II), n is 2 and X is $CR^3$.

In some embodiments of Formula (II), n is 2, X is $CR^3$, and $R^3$ is phenyl or pyridinyl, wherein the phenyl or pyridinyl are each optionally substituted one, two or three times with $R^5$.

In some embodiments of Formula (II), n is 2 and Y is $CR^3$.

In some embodiments of Formula (II), n is 2, Y is $CR^3$, and $R^3$ is phenyl or pyridinyl, wherein the phenyl or pyridinyl are each optionally substituted one, two or three times with $R^5$.

In some embodiments of Formula (II), disclosed representative compounds can have structures satisfying any one or more of the following formulas.

TABLE 1

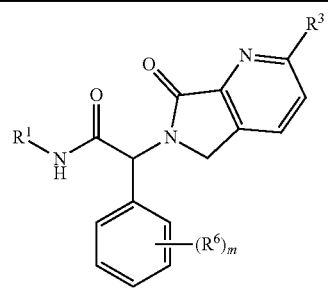

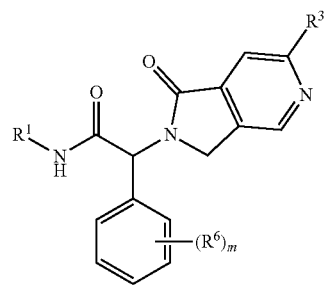

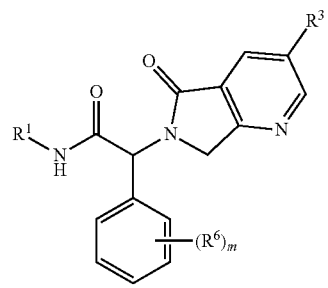

TABLE 1-continued

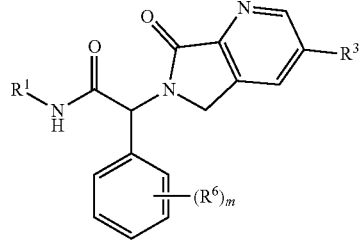

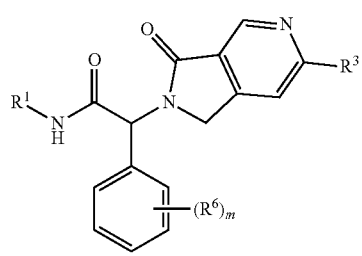

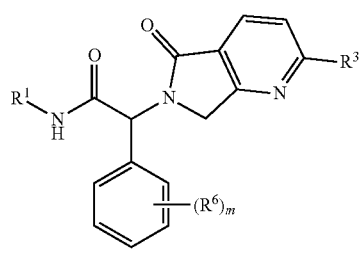

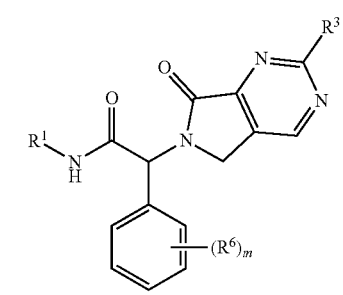

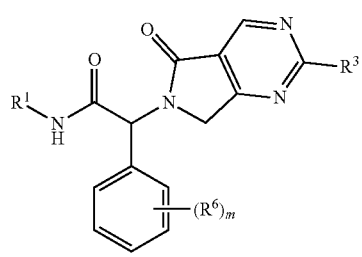

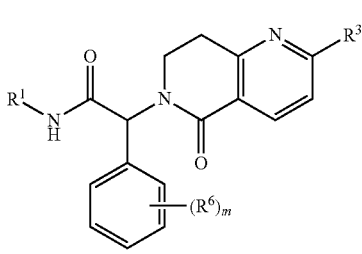

TABLE 1-continued

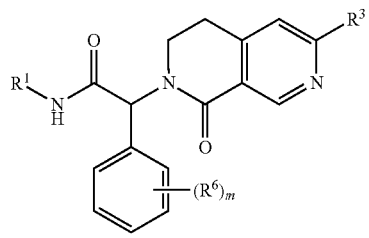

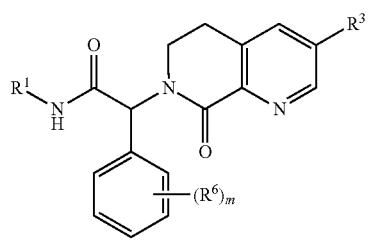

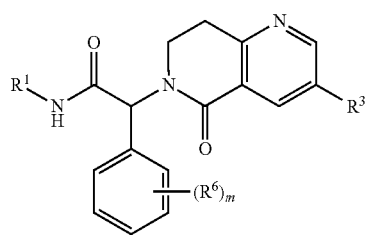

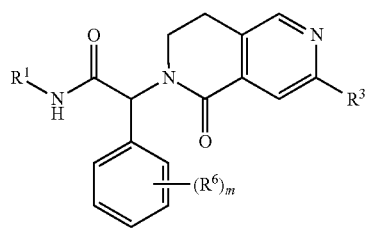

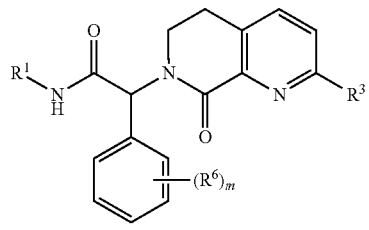

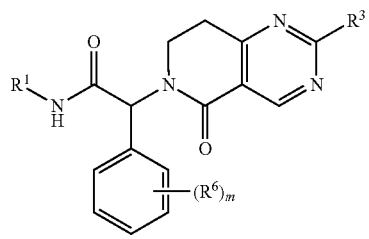

TABLE 1-continued

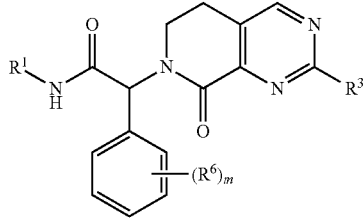

With respect to the above formulas, each of $R^1$, $R^3$, $R^6$, and m independently can be selected from groups recited above for Formula (II).

In some embodiments, the disclosure relates to compounds of Formula (IIIa) or Formula (IIIb):

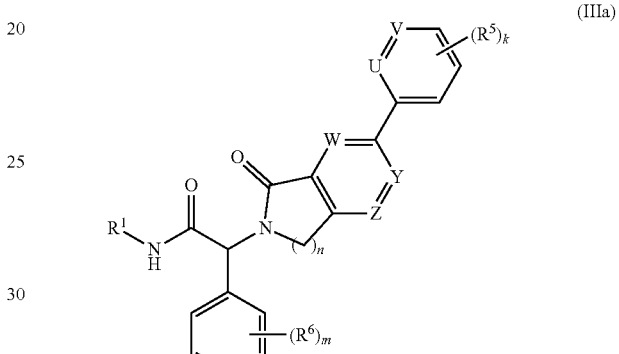

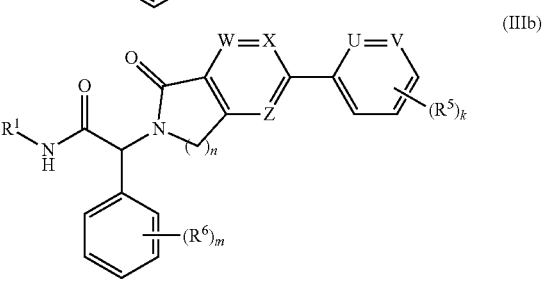

or a pharmaceutically acceptable salt or prodrug thereof, wherein:

$R^1$ is aryl or 5- to 6-membered heteroaryl;

W, X, Y, and Z are each independently N, CH, CF, or C-($C_1$-$C_3$ alkyl);

provided that at least one of W, X, Y, or Z is N;

U and V are each independently N or CH;

$R^5$, for each occurrence, is independently $C_1$-$C_6$ alkyl, $C_1$-$C_6$ haloalkyl, $C_1$-$C_6$ alkoxy, $C_1$-$C_6$ haloalkoxy, halogen, COOH, C(O)O($C_1$-$C_6$ alkyl), $NH_2$, OH, CN, $(CH_2)_{0-3}$—($C_6$-$C_{10}$ aryl), $(CH_2)_{0-3}$-(5- to 6-membered heteroaryl), or $(CH_2)_{0-3}$-(5- to 7-membered heterocyclyl), wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, NH($C_1$-$C_6$ alkyl), N($C_1$-$C_6$ alkyl)$_2$, $SO_2NH_2$, $(CH_2)_{1-2}$—OH, C(O)$(CH_2)_{1-2}$—OH, and C(O)O($C_1$-$C_6$ alkyl);

$R^6$ for each occurrence, is independently $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_p$OH, $S(O)_qH$, $S(O)_qNH_2$, or CN;

n is 1 or 2;

m is 1 or 2;

k is 1, 2, or 3;
p is 1, 2, 3, or 4; and
q is 0, 1, or 2.

In some embodiments of Formula (IIIa) and Formula (1Ib), $R^1$ is thiazolyl or pyridinyl.

In some embodiments of Formula (IIIa) and Formula (IIIb), $R^1$ is thiazolyl.

In some embodiments of Formula (IIIa) and Formula (IIIb), $R^1$ is pyridinyl.

In some embodiments of Formula (IIIa) and Formula (IIIb), W is N.

In some embodiments of Formula (IIIa) and Formula (IIIb), W is CH.

In some embodiments of Formula (IIIa) and Formula (IIIb), W is CF.

In some embodiments of Formula (IIIa) and Formula (IIIb), W is $CCH_3$.

In some embodiments of Formula (IIIb), X is N.
In some embodiments of Formula (IIIb), X is CH.
In some embodiments of Formula (IIIa), Y is N.
In some embodiments of Formula (IIIa), Y is CH.

In some embodiments of Formula (IIIa) and Formula (IIIb), Z is N.

In some embodiments of Formula (IIIa) and Formula (IIIb), Z is CH.

In some embodiments of Formula (IIIa) and Formula (IIIb), Z is CF.

In some embodiments of Formula (IIIa) and Formula (IIIb), Z is $CCH_3$.

In some embodiments of Formula (IIIa), W is N, Y is CH, and Z is CH.

In some embodiments of Formula (IIIa), W is CH, Y is N, and Z is CH.

In some embodiments of Formula (IIIa), W is CH, Y is CH, and Z is N.

In some embodiments of Formula (IIIa), W is N, Y is N, and Z is CH.

In some embodiments of Formula (IIIb), W is N, X is CH, and Z is CH.

In some embodiments of Formula (IIIb), W is CH, X is N, and Z is CH.

In some embodiments of Formula (IIIb), W is CH, X is CH, and Z is N.

In some embodiments of Formula (IIIb), W is CH, X is N, and Z is N.

In some embodiments of Formula (IIIa) and Formula (IIIb), U is CH.

In some embodiments of Formula (IIIa) and Formula (IIIb), U is N.

In some embodiments of Formula (IIIa) and Formula (IIIb), V is CH.

In some embodiments of Formula (IIIa) and Formula (IIIb), V is N.

In some embodiments of Formula (IIIa) and Formula (IIIb), U is CH and V is CH.

In some embodiments of Formula (IIIa) and Formula (IIIb), U is CH and V is N.

In some embodiments of Formula (IIIa) and Formula (IIIb), $R^5$, for each occurrence, is independently $C_1$-$C_6$ alkyl, halogen, $(CH_2)_{0-3}$—$(C_6$-$C_{10}$ aryl), $(CH_2)_{0-3}$-(5- to 6-membered heteroaryl), or $(CH_2)_{0-3}$-(5- to 7-membered heterocyclyl), wherein the aryl, heteroaryl, or heterocyclyl is optionally substituted with one or more substituents independently selected from $C_1$-$C_6$ alkyl, $C_1$-$C_6$ haloalkyl, $C_1$-$C_6$alkoxy, $C_1$-$C_6$ haloalkoxy, halogen, $NH_2$, $NH(C_1$-$C_6$ alkyl), $N(C_1$-$C_6$ alkyl)$_2$, $SO_2NH_2$, $(CH_2)_{1-2}$—OH, $C(O)(CH_2)_{1-2}$—OH, and $C(O)O(C_1$-$C_6$ alkyl).

In some embodiments of Formula (IIIa) and Formula (IIIb), $R^5$, for each occurrence, is independently $C_1$-$C_6$ alkyl, $C_6$-$C_{10}$ aryl, 5- to 6-membered heteroaryl, or 5- to 7-membered heterocyclyl, wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, $NH(C_1$-$C_6$ alkyl), $N(C_1$-$C_6$ alkyl)$_2$, $SO_2NH_2$, $(CH_2)_{1-2}$—OH, $C(O)(CH_2)_{1-2}$—OH, and $C(O)O(C_1$-$C_5$ alkyl).

In some embodiments of Formula (IIIa) and Formula (IIIb), $R^5$, for each occurrence, is independently 5- to 7-membered heterocyclyl optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy.

In some embodiments of Formula (IIIa) and Formula (IIIb), $R^5$, for each occurrence, is independently halogen or 5- to 7-membered heterocyclyl, wherein the heterocycle is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy.

In some embodiments of Formula (IIIa) and Formula (IIIb) $R^5$, for each occurrence, is independently 5- to 7-membered heterocyclyl optionally substituted with one or more $C_1$-$C_6$ alkyl.

In some embodiments of Formula (IIIa) and Formula (IIIb), $R^5$, for each occurrence, is independently halogen or 5- to 7-membered heterocyclyl, wherein the heterocycle is optionally substituted with one or more $C_1$-$C_6$ alkyl.

In some embodiments of Formula (IIIa) and Formula (IIIb), $R^5$, for each occurrence, is independently 5- to 7-membered heterocyclyl optionally substituted with one or more methyl.

In some embodiments of Formula (IIIa) and Formula (IIIb), $R^5$, for each occurrence, is independently fluoro or 5- to 7-membered heterocyclyl, wherein the heterocycle is optionally substituted with one or more methyl.

In some embodiments of Formula (IIIa) and Formula (IIIb), $R^5$, for each occurrence, is independently selected from:

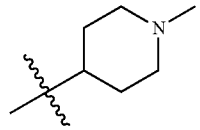

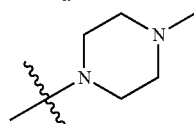

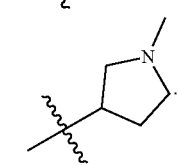

In some embodiments of Formula (IIIa) and Formula (IIIb), $R^5$, for each occurrence, is independently selected from fluoro or

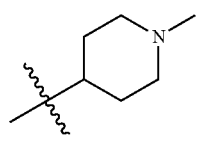

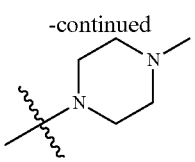

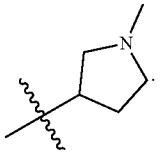

In some embodiments of Formula (IIIa) and Formula (IIIb), R⁶, for each occurrence, is independently halogen or OH.

In some embodiments of Formula (IIIa) and Formula (IIIb), R⁶, for each occurrence, is independently halogen.

In some embodiments of Formula (IIIa) and Formula (IIIb) R⁶, for each occurrence, is independently fluoro.

In some embodiments of Formula (IIIa) and Formula (IIIb), R⁶, for each occurrence, is independently OH.

In some embodiments of Formula (IIIa) and Formula (IIIb), n is 1.

In some embodiments of Formula (IIIa) and Formula (IIIb), n is 2.

In some embodiments of Formula (IIIa) and Formula (IIIb), m is 1.

In some embodiments of Formula (IIIa) and Formula (IIIb), m is 2.

In some embodiments of Formula (IIIa) and Formula (IIIb), k is 1.

In some embodiments of Formula (IIIa) and Formula (IIIb), k is 2.

In some embodiments of Formula (IIIa) and Formula (IIIb), R¹ is thiazolyl and R⁶ is fluoro.

In some embodiments of Formula (IIIa) and Formula (IIIb) R¹ is pyridinyl and R⁶ is fluoro.

In some embodiments of Formula (IIIa) and Formula (IIIb), n is 1, k is 1, W is N, U is CH, and R⁶ is fluoro or OH.

In some embodiments of Formula (IIIa), n is 1, k is 1, Y is N, U is CH, and R⁶ is fluoro or OH.

In some embodiments of Formula (IIIb), n is 1, k is 1, X is N, U is CH, and R⁶ is fluoro or OH.

In some embodiments of Formula (IIIa) and Formula (IIIb), n is 1, k is 1, Z is N, U is CH, and R⁶ is fluoro or OH.

In some embodiments of Formula (IIIa) and Formula (IIIb), k is 1, U is CH, and V is CH.

In some embodiments of Formula (IIIa) and Formula (11b), k is 1, U is CH, and V is N.

In some embodiments of Formula (IIIa) and Formula (IIIb), k is 1, U is CH, V is CH, and R⁵ is selected from:

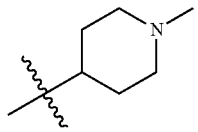

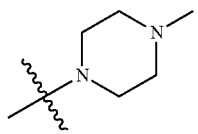

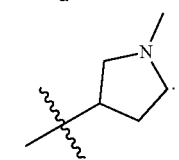

In some embodiments of Formula (IIIa) and Formula (IIIb), k is 1, U is CH, V is N, and R⁵ is selected from:

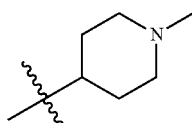

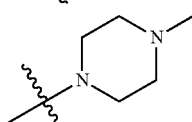

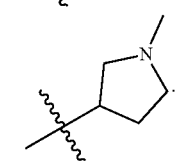

Non-limiting illustrative compounds of Formula (I), or pharmaceutically acceptable salts thereof, are exemplified in Table 2.

TABLE 2

| Compound Number | Structure | Compound Name |
|---|---|---|
| 1 | 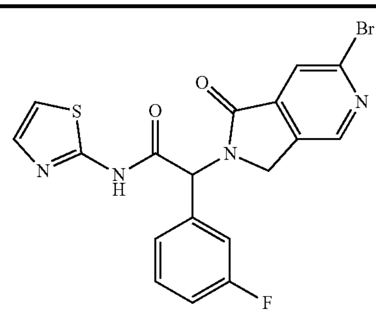 | 2-(6-bromo-1-oxo-1,3-dihydro-2H-pyrrolo[3,4-c]pyridin-2-yl)-2-(3-fluorophenyl)-N-(thiazol-2-yl)acetamide |

TABLE 2-continued

| Compound Number | Structure | Compound Name |
|---|---|---|
| 2 | 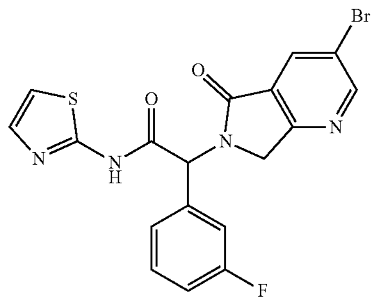 [SMILES: O=C(Nc1nccs1)C(c1cccc(F)c1)N1Cc2ncc(Br)cc2C1=O] | 2-(3-bromo-5-oxo-5,7-dihydro-6H-pyrrolo[3,4-b]pyridin-6-yl)-2-(3-fluorophenyl)-N-(thiazol-2-yl)acetamide |
| 3 | 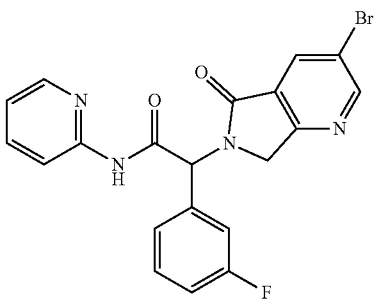 [SMILES: O=C(Nc1ccccn1)C(c1cccc(F)c1)N1Cc2ncc(Br)cc2C1=O] | 2-(3-bromo-5-oxo-5,7-dihydro-6H-pyrrolo[3,4-b]pyridin-6-yl)-2-(3-fluorophenyl)-N-(pyridin-2-yl)acetamide |
| 4 | 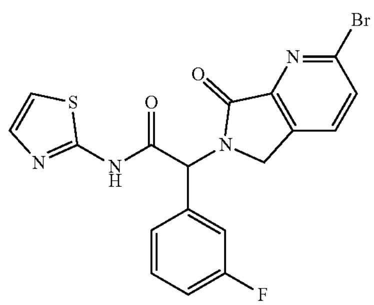 [SMILES: O=C(Nc1nccs1)C(c1cccc(F)c1)N1Cc2ccc(Br)nc2C1=O] | 2-(2-bromo-7-oxo-5,7-dihydro-6H-pyrrolo[3,4-b]pyridin-6-yl)-2-(3-fluorophenyl)-N-(thiazol-2-yl)acetamide |
| 5 | 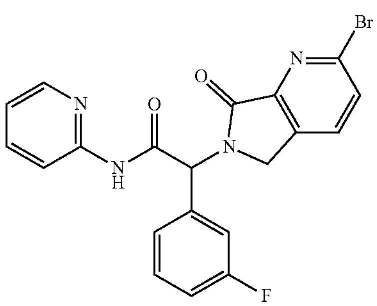 [SMILES: O=C(Nc1ccccn1)C(c1cccc(F)c1)N1Cc2ccc(Br)nc2C1=O] | 2-(2-bromo-7-oxo-5,7-dihydro-6H-pyrrolo[3,4-b]pyridin-6-yl)-2-(3-fluorophenyl)-N-(pyridin-2-yl)acetamide |
| 6 | 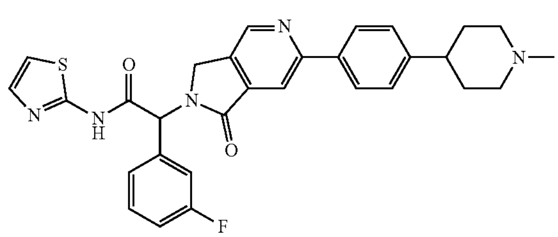 [SMILES: CN1CCC(c2ccc(-c3cc4c(cn3)CN(C(C(=O)Nc3nccs3)c3cccc(F)c3)C4=O)cc2)CC1] | 2-(3-fluorophenyl)-2-(6-(4-(1-methylpiperidin-4-yl)phenyl)-1-oxo-1,3-dihydro-2H-pyrrolo[3,4-c]pyridin-2-yl)-N-(thiazol-2-yl)acetamide |

TABLE 2-continued

| Compound Number | Structure | Compound Name |
|---|---|---|
| 7 | 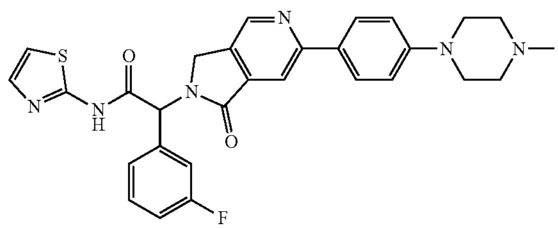 [SMILES: CN1CCN(c2ccc(-c3cc4c(cn3)CN(C(C(=O)Nc3nccs3)c3cccc(F)c3)C4=O)cc2)CC1] | 2-(3-fluorophenyl)-2-(6-(4-(4-methylpiperazin-1-yl)phenyl)-1-oxo-1,3-dihydro-2H-pyrrolo-[3,4-c]pyridin-2-yl)-N-(thiazol-2-yl)acetamide |
| 8 | 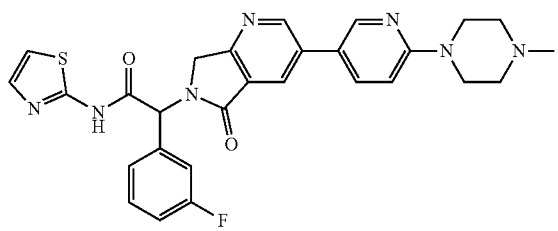 [SMILES: CN1CCN(c2ccc(-c3cnc4c(c3)C(=O)N(C(C(=O)Nc3nccs3)c3cccc(F)c3)C4)cn2)CC1] | 2-(3-fluorophenyl)-2-(3-(6-(4-methylpiperazin-1-yl)pyridin-3-yl)-5-oxo-5,7-dihydro-6H-pyrrolo[3,4-b]pyridin-6-yl)-N-(thiazol-2-yl)acetamide |
| 9 | 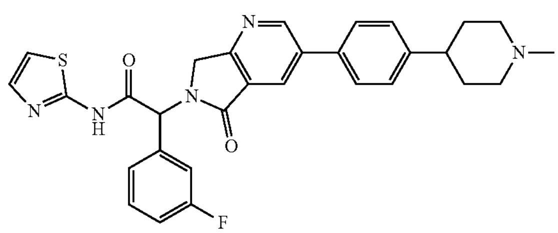 [SMILES: CN1CCC(c2ccc(-c3cnc4c(c3)C(=O)N(C(C(=O)Nc3nccs3)c3cccc(F)c3)C4)cc2)CC1] | 2-(3-fluorophenyl)-2-(3-(4-(1-methylpiperidin-4-yl)phenyl)-5-oxo-5,7-dihydro-6H-pyrrolo-[3,4-b]pyridin-6-yl)-N-(thiazol-2-yl)acetamide |
| 10 | 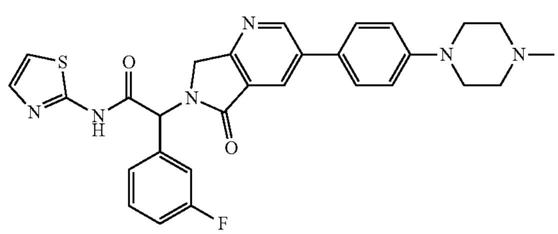 [SMILES: CN1CCN(c2ccc(-c3cnc4c(c3)C(=O)N(C(C(=O)Nc3nccs3)c3cccc(F)c3)C4)cc2)CC1] | 2-(3-fluorophenyl)-2-(3-(4-(4-methylpiperazin-1-yl)phenyl)-5-oxo-5,7-dihydro-6H-pyrrolo-[3,4-b]pyridin-6-yl)-N-(thiazol-2-yl)acetamide |
| 11 | 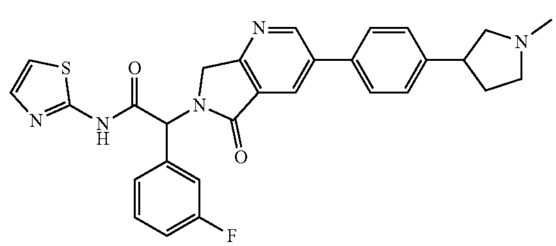 [SMILES: CN1CCC(c2ccc(-c3cnc4c(c3)C(=O)N(C(C(=O)Nc3nccs3)c3cccc(F)c3)C4)cc2)C1] | 2-(3-fluorophenyl)-2-(3-(4-(1-methylpyrrolidin-3-yl)phenyl)-5-oxo-5,7-dihydro-6H-pyrrolo-[3,4-b]pyridin-6-yl)-N-(thiazol-2-yl)acetamide |
| 12 | 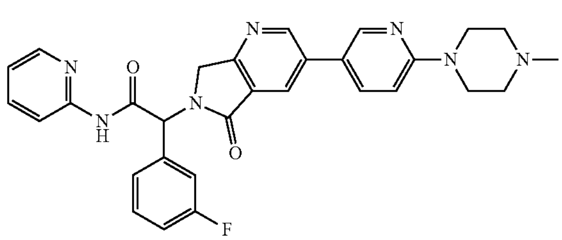 [SMILES: CN1CCN(c2ccc(-c3cnc4c(c3)C(=O)N(C(C(=O)Nc3ccccn3)c3cccc(F)c3)C4)cn2)CC1] | 2-(3-fluorophenyl)-2-(3-(6-(4-methylpiperazin-1-yl)pyridin-3-yl)-5-oxo-5,7-dihydro-6H-pyrrolo[3,4-b]pyridin-6-yl)-N-(pyridin-2-yl)acetamide |

TABLE 2-continued

| Compound Number | Structure | Compound Name |
|---|---|---|
| 13 | 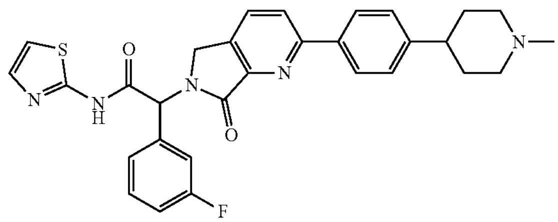 [SMILES: CN1CCC(c2ccc(-c3ccc4c(n3)C(=O)N(C(C(=O)Nc3nccs3)c3cccc(F)c3)C4)cc2)CC1] | 2-(3-fluorophenyl)-2-(2-(4-(1-methylpiperidin-4-yl)phenyl)-7-oxo-5,7-dihydro-6H-pyrrolo-[3,4-b]pyridin-6-yl)-N-(thiazol-2-yl)acetamide |
| 14 | 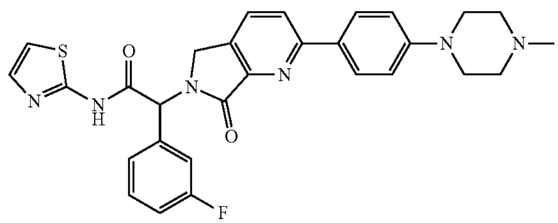 [SMILES: CN1CCN(c2ccc(-c3ccc4c(n3)C(=O)N(C(C(=O)Nc3nccs3)c3cccc(F)c3)C4)cc2)CC1] | 2-(3-fluorophenyl)-2-(2-(4-(4-methylpiperazin-1-yl)phenyl)-7-oxo-5,7-dihydro-6H-pyrrolo-[3,4-b]pyridin-6-yl)-N-(thiazol-2-yl)acetamide |
| 15 | 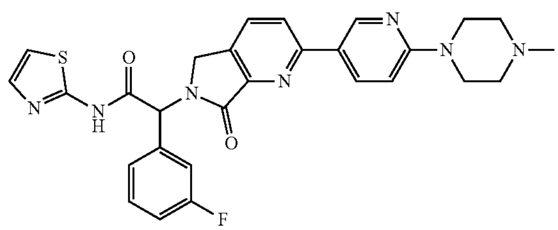 [SMILES: CN1CCN(c2ccc(-c3ccc4c(n3)C(=O)N(C(C(=O)Nc3nccs3)c3cccc(F)c3)C4)cn2)CC1] | 2-(3-fluorophenyl)-2-(2-(6-(4-methylpiperazin-1-yl)pyridin-3-yl)-7-oxo-5,7-dihydro-6H-pyrrolo[3,4-b]pyridin-6-yl)-N-(thiazol-2-yl)acetamide |
| 16 | 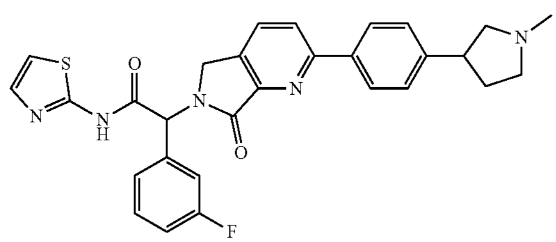 [SMILES: CN1CCC(c2ccc(-c3ccc4c(n3)C(=O)N(C(C(=O)Nc3nccs3)c3cccc(F)c3)C4)cc2)C1] | 2-(3-fluorophenyl)-2-(2-(4-(1-methylpyrrolidin-3-yl)phenyl)-7-oxo-5,7-dihydro-6H-pyrrolo-[3,4-b]pyridin-6-yl)-N-(thiazol-2-yl)acetamide |
| 17 | 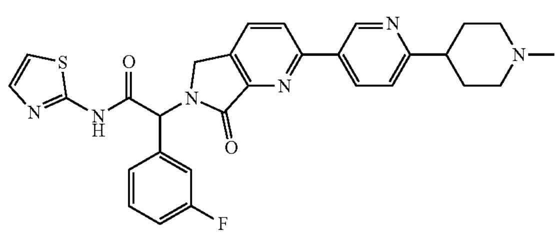 [SMILES: CN1CCC(c2ccc(-c3ccc4c(n3)C(=O)N(C(C(=O)Nc3nccs3)c3cccc(F)c3)C4)cn2)CC1] | 2-(3-fluorophenyl)-2-(2-(6-(1-methylpiperidin-4-yl)pyridin-3-yl)-7-oxo-5,7-dihydro-6H-pyrrolo[3,4-b]pyridin-6-yl)-N-(thiazol-2-yl)acetamide |
| 18 | 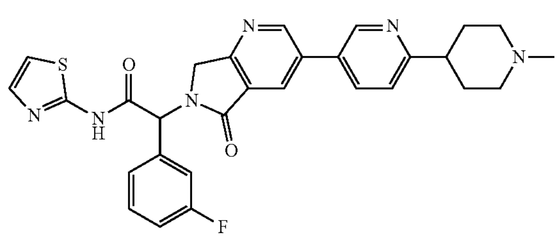 [SMILES: CN1CCC(c2ccc(-c3cnc4c(c3)C(=O)N(C(C(=O)Nc3nccs3)c3cccc(F)c3)C4)cn2)CC1] | 2-(3-fluorophenyl)-2-(3-(6-(1-methylpiperidin-4-yl)pyridin-3-yl)-5-oxo-5,7-dihydro-6H-pyrrolo[3,4-b]pyridin-6-yl)-N-(thiazol-2-yl)acetamide |

TABLE 2-continued

| Compound Number | Structure | Compound Name |
|---|---|---|
| 19 | 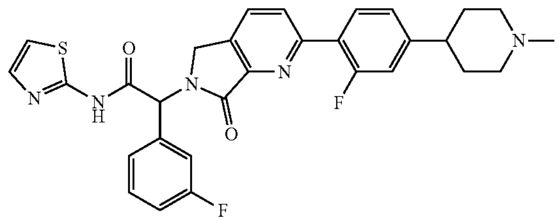 [SMILES: CN1CCC(c2ccc(-c3ccc4c(n3)C(=O)N(C(C(=O)Nc3nccs3)c3cccc(F)c3)C4)c(F)c2)CC1] | 2-(2-(2-fluoro-4-(1-methyl-piperidin-4-yl)phenyl)-7-oxo-5,7-dihydro-6H-pyrrolo[3,4-b]pyridin-6-yl)-2-(3-fluoro-phenyl)-N-(thiazol-2-yl)-acetamide |
| 20 | 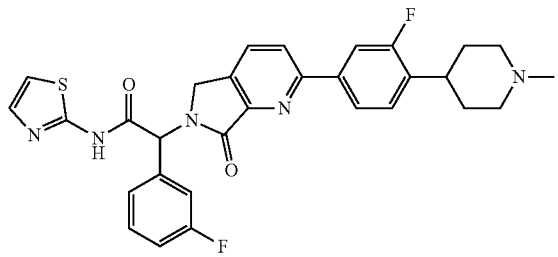 [SMILES: CN1CCC(c2ccc(-c3ccc4c(n3)C(=O)N(C(C(=O)Nc3nccs3)c3cccc(F)c3)C4)cc2F)CC1] | 2-(2-(3-fluoro-4-(1-methyl-piperidin-4-yl)phenyl)-7-oxo-5,7-dihydro-6H-pyrrolo[3,4-b]pyridin-6-yl)-2-(3-fluoro-phenyl)-N-(thiazol-2-yl)-acetamide |
| 21 | 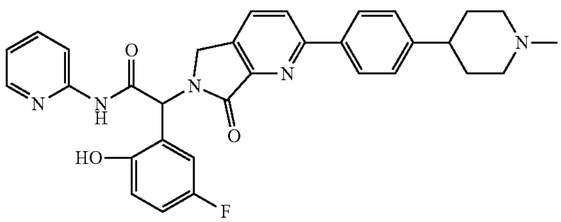 [SMILES: CN1CCC(c2ccc(-c3ccc4c(n3)C(=O)N(C(C(=O)Nc3ccccn3)c3cc(F)ccc3O)C4)cc2)CC1] | 2-(5-fluoro-2-hydroxyphenyl)-2-(2-(4-(1-methylpiperidin-4-yl)phenyl)-7-oxo-5,7-dihydro-6H-pyrrolo[3,4-b]pyridin-6-yl)-N-(pyridin-2-yl)acetamide |
| 22 | 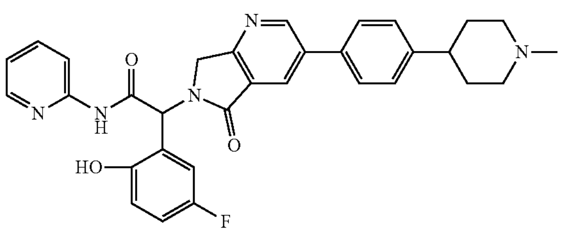 [SMILES: CN1CCC(c2ccc(-c3cnc4c(c3)C(=O)N(C(C(=O)Nc3ccccn3)c3cc(F)ccc3O)C4)cc2)CC1] | 2-(5-fluoro-2-hydroxyphenyl)-2-(3-(4-(1-methylpiperidin-4-yl)phenyl)-5-oxo-5,7-dihydro-6H-pyrrolo[3,4-b]pyridin-6-yl)-N-(pyridin-2-yl)acetamide |

The compounds of Table 2, as well as compounds of Formulae (I), (II), (IIIa), and (IIIb), are also refered to herein as "compounds of the present disclosure."

The disclosure includes all tautomers and optical isomers (e.g., enantiomers, diastereomers, diastereomeric mixtures, racemic mixtures, and the like) of the compounds of Formulae (I), (II), (IIIa), and (IIIb).

It is generally well known in the art that any compound that will be converted in vivo to provide a compound of Formulae (I), (II), (IIIa), or (IIIb) is a prodrug within the scope and spirit of the invention.

The present disclosure provides compounds and compositions with improved pharmacokinetic profiles relative to known EGFR inhibitors, specifically with respect to lipophilicity.

In another aspect, the present disclosure relates to pharmaceutical compositions comprising a compound of the present disclosure, or a pharmaceutically acceptable salt thereof, and a pharmaceutically acceptable carrier. In one embodiment, the pharmaceutical composition further comprises a second agent, wherein said second agent is a MEK inhibitor, a PI3K inhibitor, or an mTor inhibitor. In another embodiment, the pharmaceutical composition further comprises a second agent, wherein said second agent prevents EGFR dimer formation in a subject. In some embodiments, the second agent that prevents EGFR dialer formation is an antibody, In further embodiments, the second agent that prevents EGFR dimer formation is cetuximab, trastuzumab, or panitumumab. In further embodiments, the second agent that prevents EGFR dimer formation is cetuximab. In another embodiment, the pharmaceutical composition further comprises a second agent, wherein said second agent is an ATP-competitive inhibitor. In further embodiments, the ATP-competitive inhibitor is osimertinib.

A compound that binds to an allosteric site in EGFR, such as the compounds of the present disclosure (e.g., the compounds of the formulae disclosed herein), optionally in combination with a second agent are capable of modulating EGFR activity. In some embodiments, the compounds of the present disclosure are capable of inhibiting or decreasing EGFR activity without a second agent (e.g., an antibody such as cetuximab, trastuzumab, or panitumumab). In other embodiments, the compounds of the present disclosure in combination with a second agent, wherein said second agent prevents EGFR dimer formation, are capable of inhibiting or decreasing EGFR activity. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the compounds of the present disclosure in combination with an ATP-competitive EGFR inhibitor are capable of inhibiting or decreasing EGFR activity. In further embodiments, the ATP-competitive inhibitor is osimertinib.

In some embodiments, the compounds of the present disclosure are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M.

In some embodiments, the compounds of the present disclosure in combination with a second agent are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In some embodiments, the compounds of the present disclosure are capable of modulating (e.g., inhibiting or decreasing) the activity of EGFR containing one or more mutations, but do not affect the activity of a wild-type EGFR.

In other embodiments, the compounds of the present disclosure in combination with a second agent, wherein said second agent prevents EGFR dimer formation, are capable of modulating (e.g., inhibiting or decreasing) the activity of EGFR containing one or more mutations, but do not affect the activity of a wild-type EGFR. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In other embodiments, the compounds of the present disclosure in combination with a second agent, wherein said second agent is an ATP-competitive inhibitor, are capable of modulating (e.g., inhibiting or decreasing) the activity of EGFR containing one or more mutations, but do not affect the activity of a wild-type EGFR. In some embodiments, the ATP-competitive inhibitor is osimertinib.

Modulation of EGFR containing one or more mutations, such as those described herein, but not a wild-type EGFR, provides a novel approach to the treatment, prevention, or amelioration of diseases including, but not limited to, cancer and metastasis, inflammation, arthritis, systemic lupus erythematosus, skin-related disorders, pulmonary disorders, cardiovascular disease, ischemic, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit greater inhibition of EGFR containing one or more mutations as described herein relative to a wild-type EGFR. In certain embodiments, the compounds of the disclosure exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure exhibit up to 1000-fold greater inhibition of EGFR containing one or more mutations as described herein relative to a wild-type EGFR. In various embodiments, the compounds of the disclosure exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR.

In other embodiments, the compounds of the disclosure in combination with a second agent exhibit greater inhibition of EGFR containing one or more mutations as described herein relative to a wild-type EGFR. In certain embodiments, the compounds of the disclosure in combination with a second agent exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure in combination with a second agent exhibit up to 1000-fold greater inhibition of EGFR containing one or more mutations as described herein relative to a wild-type EGFR. In various embodiments, the compounds of the disclosure in combination with a second agent exhibit up to 10000-fold greater inhibition of EGFR having a combination of mutations described herein (e.g., L858R/1790M, L858R/T790M/1941R, L858RlT790M/C797S, Del/T790M, Del/T790M/C797S, and L858R/T790M) relative to a wild-type EGFR. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab, In some embodiments, the second agent is an ATP-competitive EGFR inhibitor. In further embodiments, the ATP-competitive EGFR inhibitor is osimertinib.

In some embodiments, the compounds of the disclosure exhibit from about 2-fold to about 10-fold greater inhibition of EGFR containing one or more mutations as described herein relative to a wild-type EGFR. In various embodiments, the compounds of the disclosure exhibit from about 10-fold to about 100-fold greater inhibition of EGFR containing one or more mutations as described herein relative to a wild-type EGFR, In various embodiments, the compounds of the disclosure exhibit from about 100-fold to about 1000-fold greater inhibition of EGFR containing one or more mutations as described herein relative to a wild-type EGFR. In various embodiments, the compounds of the disclosure exhibit from about 1000-fold to about 10000-fold greater inhibition of EGFR containing one or more mutations as described herein relative to a wild-type EGFR.

In other embodiments, the compounds of the disclosure in combination with a second agent exhibit from about 2-fold to about 10-fold greater inhibition of EGFR containing one or more mutations as described herein relative to a wild-type EGFR. In other embodiments, the compounds of the disclosure in combination with a second agent exhibit from about 10-fold to about 100-fold greater inhibition of EGFR containing one or more mutations as described herein relative to a wild-type EGFR. In other embodiments, the compounds of the disclosure in combination with a second agent exhibit from about 100-fold to about 1000-fold greater inhibition of EGFR containing one or more mutations as described herein relative to a wild-type EGFR. In other embodiments, the compounds of the disclosure in combination with a second agent exhibit from about 1000-fold to about 10000-fold greater inhibition of EGFR containing one or more mutations as described herein relative to a wild-type EGFR. In some embodiments, the second agent prevents EGFR dimer formation in a subject. In other embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive inhibitor is osirnertinib.

In certain embodiments, the compounds of the disclosure exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 3-fold greater inhibition of EGFR having a combination of mutations selected from L858R/T790M, L858R/T790M/I941R, L858R/T790M/C797S, Del/T790M, De1/1790M/C797S, and L858R/T790M relative to a wild-type EGFR. In certain embodiments, the compounds of the disclosure exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR, In certain embodiments, the compounds of the disclosure exhibit at least 25-fold greater inhibition of EGFR having a combination of mutations selected from L858R/T790M, L858R/T790M/I941R, L858R/T790MIC797S, Del/T790M, Del/T790M/C797S, and L858R/T790M relative to a wild-type EGFR. In certain embodiments, the compounds of the disclosure exhibit at least 50-fold greater inhibition of EGFR having a combination of mutations selected from L L858R/T790M, L858RIT790M/I941R, L858R/T790M/C797S, Del/T790M, Del/T790M/C797S, and L858R/T790M relative to a wild-type EGFR. In certain embodiments, the compounds of the disclosure exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR.

In certain embodiments, the compounds of the disclosure in combination with a second agent exhibit at least 2-fold greater inhibition of EGFR having a combination of mutations selected from L858R/T790M, L858R/T790M/I941R, L858R/T790M/C797S, Del/T790M, DeliT790M/C797S, and L858R/T790M relative to a wild-type EGFR. In certain embodiments, the compounds of the disclosure in combination with a second agent exhibit at least 3-fold greater inhibition of EGFR having a combination of mutations selected from L858R1T790M, L858R/T790M/I941R, L858R/T790M/C7973, Del/T790M, Del/T790W/C797S, and L.858R/T7901V1 relative to a wild-type EGFR. In certain embodiments, the compounds of the disclosure in combination with a second agent exhibit at least 5-fold greater inhibition of EGFR having a combination of mutations selected from L858R/T790M, L858RIT790M/I941R, L858R/T790M/C797S, Del/T790M, Del/T790M/C797S, and L858R/T790M relative to a wild-type EGFR. In certain embodiments, the compounds of the disclosure in combination with a second agent exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second agent exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive inhibitor, In further embodiments, the ATP-competitive inhibitor is osimertinib.

In some embodiments, the inhibition of EGFR activity is measured by $IC_{50}$.

In some embodiments, the inhibition of EGFR activity is measured by $EC_{50}$.

In some embodiments, the inhibition of EGFR by a compound of the disclosure can be measured via a biochemical assay. By illustrative and non-limiting example, a homogenous time-resolved fluorescence (HTRF) assay may be used to determine inhibition of EGFR activity using conditions and experimental parameters disclosed herein. The HTRF assay may, for example, employ concentrations of substrate (e.g., biotin-Lck-peptide substrate) of about 1 μM; concentrations of EGFR (mutant or WT) from about 0.2 nM to about 40 nM; and concentrations of inhibitor from about 0.000282 μM to about 50 μM. A compound of the disclosure screened under these conditions may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM. In certain embodiments, a compound of the disclosure screened under the above conditions for inhibition of EGFR having a mutation or combination of mutations selected from L858R/T790M, L858R, and T790M may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM.

In some embodiments, the compounds of the disclosure bind to an allosteric site in EGFR. In some embodiments, the compounds of the disclosure interact with at least one amino acid residue of epidermal growth factor receptor (EGFR) selected from Lys745, Leu788, and Ala 743. In other embodiments, the compounds of the disclosure interact with at least one amino acid residue of epidermal growth factor receptor (EGFR) selected from Cys755, Leu777, Phe856, and Asp855. In other embodiments, the compounds of the disclosure interact with at least one amino acid residue of epidermal growth factor receptor (EGFR) selected from Met766, lle759, Glu762, and Ala763. In other embodiments, the compounds of the disclosure interact with at least one amino acid residue of epidermal growth factor receptor (EGFR) selected from Lys745, Leu788, and Ala 743; at least one amino acid residue of epidermal growth factor receptor (EGFR) selected from Cys755, Leu777, Phe856, and Asp855; and at least one amino acid residue of epidermal growth factor receptor (EGFR) selected from Met766, 11e759, Glu762, and Ala763. In other embodiments, the compounds of the disclosure do not interact with any of the amino acid residues of epidermal growth factor receptor (EGFR) selected from Met793, Gly796, and Cys797.

In some embodiments, the disclosure provides a compound comprising an allosteric kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002:

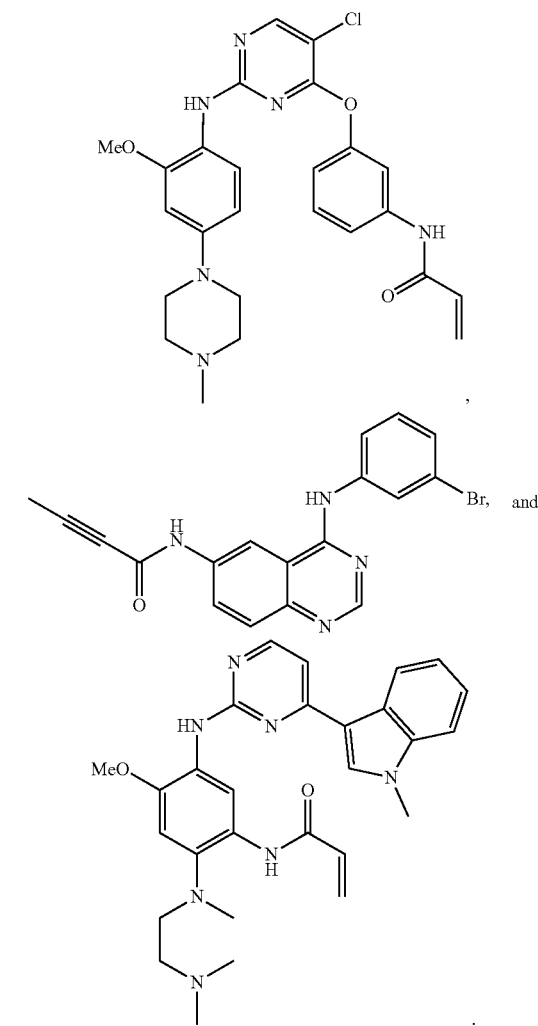

In some embodiments, the drug-resistant EGFR mutant comprises a sensitizing mutation, such as Del and L858R.

In some embodiments, the disclosure provides a compound comprising an allosteric kinase inhibitor in combination with a second agent wherein the compound is a more potent inhibitor of a drug-resistant EGFR mutant relative to a wild type EGFR. For example, the compound in combination with a second agent can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and osimertinib. In some embodiments, the drug-resistant EGFR mutant comprises a sensitizing mutation, such as Del and L858R. In some embodiments, the second agent prevents EGFR dimer formation in a subject In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In some embodiments, the disclosure provides a compound comprising an allosteric kinase inhibitor, wherein the compound inhibits kinase activity of a drug-resistant EGFR mutant harboring a sensitizing mutation (e.g., Del and L858R) and a drug-resistance mutation (e.g., T790M, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In other embodiments, the disclosure provides a compound comprising an allosteric kinase inhibitor in combination with a second agent wherein the compound in combination with the second agent inhibits kinase activity of a drug-resistant EGFR mutant harboring a sensitizing mutation (e.g., Del and L858R) and a drug-resistance mutation (e.g., T790M, L718Q, 0797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold, In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab, In further embodiments, the second agent that prevents EGFR dimer formation is cetuximab, In some embodiments, the second agent is an ATP-competitive EGFR inhibitor. In further embodiments, the ATP-competitive EGFR inhibitor is osirnertinib.

In some embodiments, the disclosure provides a compound comprising an allosteric kinase inhibitor, wherein the compound is more potent than one or more known EGFR inhibitors, including but not limited to gefitinib, erlotinib, lapatinib, V124002, HKI-272, CL-387785, and osimertinib, at inhibiting the activity of EGFR containing one or more mutations as described herein, such as T790M, L7180, L844V, L858R, C797S, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, L-387785, and osimertinib at inhibiting the activity of the EGFR containing one or more mutations as described herein.

In other embodiments, the disclosure provides a compound comprising an allosteric kinase inhibitor in combination with a second agent wherein the compound in combination with the second agent is more potent than one or more known EGFR inhibitors, including but not limited to gefitinib, erlotinib, lapatinib, WZ4002, HKI-272, CL-387785, and osirnertinib, at inhibiting the activity of EGFR containing one or more mutations as described herein, such as T790M, L718Q, L844V, L858R, C797S, and Del. For example, the compound in combination with a second agent can be at least about 2-fold, 3-fold, 5-fold, 10-fold, 25-fold, 50-fold or about 100-fold more potent (e.g., as measured by IC50) than gefitinib, erlotinib, lapatinib, WZ4002, HKI-272, CL-387785, and osimertinib at inhibiting the activity of the EGFR containing one or more mutations as described herein. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In some embodiments, the disclosure provides a compound comprising an allosteric kinase inhibitor, wherein the compound is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, W.74002, HKI-272, CL-387785, and osimertinib, at inhibiting the activity of a wild-type EGFR.

In other embodiments, the disclosure provides a compound comprising an allosteric kinase inhibitor in combination with a second agent wherein the compound in combination with the second agent is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound in combination with a second agent can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR. In some embodiments, the second agent prevents EGFR dimer formation in a subject. In some embodiments, the second agent that prevents EGFR dialer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

Potency of the inhibitor can be determined by E050 value. A compound with a lower $EC_{50}$ value, as determined under substantially similar conditions, is a more potent inhibitor relative to a compound with a higher $EC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

An EGFR sensitizing mutation comprises without limitation L858R, G719S, G719C, G719A, L8610, a deletion in exon 19 and/or an insertion in exon 20. A drug-resistant EGFR mutant can have without limitation a drug resistance mutation comprising T790M, T854A, L718Q, C797S, or D761Y.

The selectivity between wild-type EGFR and EGFR containing one or more mutations as described herein can also be measured using cellular proliferation assays where cell proliferation is dependent on kinase activity. For example, murine Ba/F3 cells transfected with a suitable version of wild-type EGFR (such as VIII; containing a WT EGFR kinase domain), or Ba/F3 cells transfected with L858R/T790M, DeitT790M/L718Q, L858R/T790MIL718Q, L858RfT790M/C797S, Del/T790M/C797S, L858R/T790M/I941R, or Exon 19 deletion/T790M can be used. Proliferation assays are performed at a range of inhibitor concentrations (10 μM, 3 μM, 1.1 μM, 330 nM, 110 nM, 33 nM, 11 nM, 3 nM, I nM) and an $EC_{50}$ is calculated.

An alternative method to measure effects on EGFR activity is to assay EGFR phosphorylation. Wld type or mutant (L858R1T790M, Del/T790M, Del/T790M/L718Q, L858R/T790M/C797S, Del/T790M/C797S, L858R/T790M/I941R, or L858R/T790M/L718Q) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes, The effects on EGFR phosphorylation are assayed by Western Blotting using phospho-specific (Y1068) EGFR antibodies.

In another aspect, the present disclosure relates to a compound that binds to an allosteric site in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790N/l/L718Q, L858R/T790M/C797S, Del/T790M/C797S, L858R/T790M/I1941R, or L858R/T790M/L7180) relative to a wild-type EGFR.

In other embodiments, the disclosure provides a compound that binds to an allosteric site in EGFR in combination with a second agent wherein the compound in combination with the second agent exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L7180, Del/T790M/C797S, L858R/T790M/C797S, L858RIT790M/I941R, or L858RIT790M/L718Q) relative to a wild-type EGFR. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

Methods of Treatment

In another aspect, the disclosure provides a method of inhibiting a kinase, comprising contacting the kinase with a compound disclosed herein, or a pharmaceutically acceptable salt thereof. In some embodiments, the kinase is epidermal growth factor receptor (EGFR). In some embodiments, the kinase comprises a mutated cysteine residue. In further embodiments, the mutated cysteine residue is located in or near the position equivalent to Cys 797 in EGFR, including such position in Jak3, Blk, Bmx, Btk, HER2 (ErbB2), HER4 (ErbB4), Itk, Tec, and Txk. In other embodiments, the method further comprises a second agent. In some embodiments, the second agent prevents kinase dimer formation. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In another aspect, the disclosure provides a method of inhibiting a kinase, comprising contacting the kinase with a compound of disclosed herein, or a pharmaceutically acceptable salt thereof, and a second agent. In some embodiments, the kinase is epidermal growth factor receptor (EGFR). In some embodiments, the kinase comprises a mutated cysteine residue. In further embodiments, the mutated cysteine residue is located in or near the position equivalent to Cys 797 in EGFR, including such position in Jak3, Blk, Bmx, Btk, HER2 (ErbB2), HER4 (ErbB4), Itk, Tec, and Txk. In some embodiments, the second agent prevents dimer formation of the kinase. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In another aspect, the disclosure provides a method of inhibiting a kinase, the method comprising administering to a subject in need thereof an effective amount of a compound disclosed herein, or a pharmaceutically acceptable salt thereof. In some embodiments, the kinase is a Her-kinase. In further embodiments, the kinase is epidermal growth factor receptor (EGFR). In other embodiments, the method further comprises administering a second agent. In some embodiments, the second agent prevents dimer formation of the kinase in the subject, In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In another aspect, the disclosure provides a method of inhibiting a kinase, the method comprising administering to a subject in need thereof an effective amount of a compound disclosed herein, or a pharmaceutically acceptable salt thereof, and a second agent. In some embodiments, the kinase is a Her-kinase. In further embodiments, the kinase is epidermal growth factor receptor (EGFR). In some embodiments, the second agent prevents dimer formation of the kinase. In some embodiments, the second agent that prevents kinase dimer formation is an antibody, In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In still another aspect, the disclosure provides a method of inhibiting epidermal growth factor receptor (EGFR), the method comprising administering to a subject in need thereof an effective amount of a compound of disclosed herein, or a pharmaceutically acceptable salt thereof. In some embodiments, the method further comprises administering a second agent. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab, In some embodiments, the second agent is an ATP-competitive EGFR inhibitor. In further embodiments, the ATP-competitive EGFR inhibitor is osimertinib.

In another aspect, the disclosure provides a method of inhibiting epidermal growth factor receptor (EGFR), the method comprising administering to a subject in need thereof an effective amount of a compound of disclosed herein, or a pharmaceutically acceptable salt thereof, and a second agent. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

Another aspect of the disclosure provides a method of treating or preventing a disease, the method comprising administering to a subject in need thereof an effective amount of a compound disclosed herein, or a pharmaceutically acceptable salt thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), ltk, Tec, and Txk. In some embodiments, the method further comprises administering a second agent. In some embodiments, the second agent is a MEK inhibitor, a PI3K inhibitor, or an mTor inhibitor. In some embodiments, the second agent prevents EGFR dimer formation in the subject. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In some embodiments, the disease is mediated by EGFR (e.g., EGFR plays a role in the initiation or development of the disease). In some embodiments, the disease is mediated by a Her-kinase. In further embodiments, the Her-kinase is HER1, HER2, or HER4.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L7180, 0797S, or D761Y. The diagnostic test can comprise sequencing, pyrosequencing, POR, RT-PCR, or similar analysis techniques known to those of skill in the art that can detect nucleotide sequences.

In another aspect, the disclosure provides a method of treating or preventing a disease, the method comprising administering to a subject in need thereof an effective amount of a compound of disclosed herein, or a pharmaceutically acceptable salt thereof, and a second agent. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk.

In other embodiments, the disease is mediated by EGFR (e.g., EGFR plays a role in the initiation or development of the disease). In some embodiments, the disease is mediated by a Her-kinase. In further embodiments, the Her-kinase is HER1, HER2, or HER4. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab, In some embodiments, the second agent is an ATP-competitive EGFR inhibitor. In further embodiments, the ATP-competitive EGFR inhibitor is osimertinib.

In certain embodiments, the disease is cancer or a proliferation disease.

In certain embodiments, the disease is cancer.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, POR, RT-PCR, or similar analysis techniques known to those of skill in the art that can detect nucleotide sequences.

Another aspect of the disclosure provides a method of treating a kinase mediated disorder, the method comprising administering to a subject in need thereof an effective amount of a compound disclosed herein, or a pharmaceutically acceptable salt thereof. In some embodiments, the compound is an inhibitor of HER1, HER2, or HER4. In other embodiments, the subject is administered an additional therapeutic agent. In other embodiments, the compound and the additional therapeutic agent are administered simultaneously or sequentially.

In another aspect, the disclosure provides a method of treating a kinase mediated disorder, the method comprising administering to a subject in need thereof an effective amount of a compound of disclosed herein, or a pharmaceutically acceptable salt thereof, and a second agent. In some embodiments, the compound is an inhibitor of HER1, HER2, or HER4. In other embodiments, the subject is administered an additional therapeutic agent. In other embodiments, the compound, the second agent, and the additional therapeutic agent are administered simultaneously or sequentially. In some embodiments, the second agent is a MEK inhibitor, a PI3K inhibitor, or an mTor inhibitor. In some embodiments, the second agent prevents EGFR dimer formation in the subject, In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In certain embodiments, the kinase mediated disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors, In further embodiments, the disease is lung cancer, breast cancer, glioma, squamous cell carcinoma, or prostate cancer, In still further embodiments, the disease is non-small cell lung cancer.

In another aspect, the disclosure provides a method of treating or preventing cancer, wherein the cancer cell comprises activated EGFR, comprising administering to a subject in need thereof an effective amount of a compound of disclosed herein, or a pharmaceutically acceptable salt thereof.

In another aspect, the disclosure provides a method of treating or preventing cancer, wherein the cancer cell comprises activated EGFR, comprising administering to a subject in need thereof an effective amount of a compound of disclosed herein, or a pharmaceutically acceptable salt thereof, and a second agent. In some embodiments, the second agent is a MEK inhibitor, a PI3K inhibitor, or an mTor inhibitor. In some embodiments, the second agent prevents EGFR dimer formation in the subject, In some embodiments, the second agent that prevents EGFR dimer formation is an antibody, In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor, In further embodiments, the ATP-competitive EGFR inhibitor is osimertinib.

In certain embodiments, the EGFR activation is selected from mutation of EGFR, amplification of EGFR, expression of EGFR, and ligand mediated activation of EGFR.

In further embodiments, the mutation of EGFR is selected from G719S, G719C, G719A, L858R, L861Q, an exon 19 deletion mutation, and an exon 20 insertion mutation.

Another aspect of the disclosure provides a method of treating or preventing cancer in a subject, wherein the subject is identified as being in need of EGFR inhibition for the treatment of cancer, comprising administering to the subject an effective amount of a compound of disclosed herein, or a pharmaceutically acceptable salt thereof.

In another aspect, the disclosure provides a method of treating or preventing cancer in a subject, wherein the subject is identified as being in need of EGFR inhibition for the treatment of cancer, comprising administering to the subject an effective amount of a compound disclosed herein, or a pharmaceutically acceptable salt thereof, and optionally a second agent. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In certain embodiments, the subject identified as being in need of EGFR inhibition is resistant to a known EGFR inhibitor, including but not limited to, gefitinib, erlotinib, osimertinib, CO-1686, or WZ4002. In certain embodiments, a diagnostic test is performed to determine if the subject has an activating mutation in EGFR, In certain embodiments, a diagnostic test is performed to determine if the subject has an EGFR harboring an activating mutation and/or a drug resistance mutation. Activating mutations comprise without limitation L858R, G719S, G719O, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

Another aspect of the disclosure provides a method of preventing resistance to a known EGFR inhibitor (including but not limited to gefitinib, erlotinib, osimertinib, CO-1686, or WZ4002) in a disease, comprising administering to a subject in need thereof an effective amount of a compound disclosed herein, or a pharmaceutically acceptable salt thereof.

Another aspect of the disclosure provides a method of preventing resistance to a known EGFR inhibitor (including but not limited to gefitinib, erlotinib, osimertinib, CO-1686, or WZ4002) in a disease, comprising administering to a subject in need thereof an effective amount of a compound disclosed herein, or a pharmaceutically acceptable salt thereof, and a second agent,. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

In certain embodiments, the disclosure provides a method of treating any of the disorders described herein, wherein the subject is a human. In certain embodiments, the disclosure provides a method of preventing any of the disorders described herein, wherein the subject is a human.

In another aspect, the disclosure provides a compound disclosed herein, or a pharmaceutically acceptable salt thereof, for use in the manufacture of a medicament for treating or preventing a disease in which EGFR plays a role.

In another aspect, the disclosure provides a compound disclosed herein, or a pharmaceutically acceptable salt thereof, and a second agent, for use in the manufacture of a medicament for treating or preventing a disease in which EGFR plays a role. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor, In further embodiments, the ATP-competitive EGFR inhibitor is osimertinib.

In still another aspect, the disclosure provides the use of a compound disclosed herein, or a pharmaceutically acceptable salt thereof, in the treatment or prevention of a disease in which EGFR plays a role.

In another aspect, the disclosure provides the use of a compound disclosed herein, or a pharmaceutically acceptable salt thereof, and a second agent, in the treatment or prevention of a disease in which EGFR plays a role. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

As inhibitors of Her kinases, the compounds and compositions of this disclosure are particularly useful for treating or lessening the severity of a disease, condition, or disorder where a protein kinase is implicated in the disease, condition, or disorder. In one aspect, the present disclosure provides a method for treating or lessening the severity of a disease, condition, or disorder where a protein kinase is implicated in the disease state. In another aspect, the present disclosure provides a method for treating or lessening the severity of a kinase disease, condition, or disorder where inhibition of enzymatic activity is implicated in the treatment of the disease. In another aspect, this disclosure provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colonrectum, large intestine, rectum, brain and central nervous system, chronic myeloid leukemia (CML), and leukemia. The term "cancer" includes, but is not limited to, the following cancers: myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

the term "cancerous cell" as provided herein, includes a cell afflicted by any one of the above-identified conditions.

The disclosure further provides a method for the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias, or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, adrenoleukodystrophy (ALD), Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilders disease, subacute combined degeneration of spinal cord secondary to pernicious anaemia, Spielmeyer-Vogt-Sjogren-Batten disease (also known as Batten disease), spinocerebellar ataxia (multiple types with varying characteristics), spinal muscular atrophy, Steele-Richardson-Olszewski disease, tabes dorsalis, and toxic encephalopathy.

Another aspect of this disclosure provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof. In other embodiments, the method further comprises administering a second agent. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

As inhibitors of Her kinases, the compounds and compositions of this disclosure are also useful in biological samples. One aspect of the disclosure relates to inhibiting protein kinase activity in a biological sample, which method comprises contacting said biological sample with a compound of the disclosure or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this disclosure relates to the study of Her kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds and compositions of the present disclosure as Her kinase inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitorikinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt thereof, and optionally a second agent. For any of the above uses, the required dosage will vary depending on the mode of administration, the particular condition to be treated and the effect desired.

In some embodiments, the compound and the second agent are administered simultaneously or sequentially.

Pharmaceutical Compositions and Combination Therapies

In another aspect, the disclosure provides a pharmaceutical composition comprising a compound disclosed herein, or a pharmaceutically acceptable salt thereof, together with a pharmaceutically acceptable carrier.

In another aspect, the disclosure provides a pharmaceutical composition comprising a compound disclosed herein, or a pharmaceutically acceptable salt thereof, and a second agent, together with a pharmaceutically acceptable carrier. In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib.

Compounds of the disclosure can be administered as pharmaceutical compositions by any conventional route, in particular enterally, e.g., orally, e.g., in the form of tablets or capsules; or parenterally, e.g., in the form of injectable solutions or suspensions; topically, e.g., in the form of lotions, gels, ointments or creams; or in a nasal or suppository form. Pharmaceutical compositions comprising a compound of the present disclosure or a pharmaceutically acceptable salt thereof and, optionally, a second agent, together with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid or its magnesium or calcium salt, and/or polyethylene glycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers, In addition, they may also contain other therapeutically valuable substances. Suitable formulations for transdermal applications include an effective amount of a compound of the present disclosure with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds and compositions of the disclosure can be administered in therapeutically effective amounts in a combinational therapy with one or more therapeutic agents (pharmaceutical combinations) or modalities, e.g., a second agent that prevents EGFR dimer formation, ATP-competitive EGFR inhibitors, non-drug therapies, etc. For example, synergistic effects can occur with agents that prevents EGFR dimer formation, or with other anti-proliferative, anti-cancer, immunomodulatory, or anti-inflammatory substances. Where the compounds of the disclosure are administered in conjunction with other therapies, dosages of the co-administered compounds will of course vary depending on the type of co-drug employed, on the specific drug employed, on the condition being treated, and so forth.

Combination therapy includes the administration of the disclosed compounds in further combination with one or more other biologically active ingredients (such as, but not limited to: a MEK inhibitor; a PI3K inhibitor; an mTor inhibitor; a second agent that prevents EGFR dimer formation; an ATP-competitive EGFR inhibitor; a second and different antineoplastic agent) and non-drug therapies (such as, but not limited to surgery or radiation treatment). For instance, the compounds of the disclosure can be used in combination with other pharmaceutically active compounds, preferably compounds that are able to enhance the effect of the compounds of the disclosure. The compounds of the disclosure can be administered simultaneously (as a single preparation or separate preparation) or sequentially to the other drug therapy or treatment modality. In general, a combination therapy envisions administration of two or more drugs during a single cycle or course of therapy.

In one aspect of the disclosure, the compounds may be administered in combination with one or more additional agents (e.g., a chemotherapeutic agent, an immunotherapeutic agent, or an adjunctive therapeutic agent). In some embodiments, the additional agent is a MEK inhibitor, a PI3K inhibitor, or an mTor inhibitor. In some embodiments, the additional agent prevents EGFR dimer formation in the subject. In some embodiments, the additional agent that prevents EGFR dimer formation is an antibody. In further embodiments, the additional agent that prevents EGFR dimer formation is cetuximab, trastuzumab, or panitumumab. In further embodiments, the additional agent that prevents EGFR dimer formation is cetuximab. In some embodiments, the additional agent is an ATP-competitive EGFR inhibitor. In further embodiments, the ATP-competitive inhibitor is gefitinib, erlotinib, osimertinib, CO-1686 or WZ4002. In still further embodiments, the ATP-competitive EGFR inhibitor is osimertinib.

The pharmaceutical compositions of the present disclosure comprise a therapeutically effective amount of a compound of the present disclosure formulated together with one or more pharmaceutically acceptable carriers. As used herein, the term "pharmaceutically acceptable carrier" means a non-toxic, inert solid, semi-solid, or liquid filler, diluent, encapsulating material, or formulation auxiliary of any type. The pharmaceutical compositions of this disclosure can be administered to humans and other animals orally, rectally, parenterally, intracisternally, intravaginally, intraperitoneally, topically (as by powders, ointments, or drops), buccally, or as an oral or nasal spray. In other embodiments, the composition further comprises administering a second agent, In some embodiments, the second agent is a MEK inhibitor, a PI3K inhibitor, or an mTor inhibitor. In some embodiments, the second agent prevents EGFR dimer formation in the subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor. In further embodiments, the ATP-competitive EGFR inhibitor is osimertinib, Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof, Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents, The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U,S,P., and isotonic sodium chloride solution. In addition, sterile, fixed oils are conventionally employed as a solvent or suspending medium, For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like, The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose, In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body, Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment. In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

In certain embodiments, these compositions optionally further comprise one or more additional therapeutic agents. For example, an agent that prevents EGFR dimer formation, an ATP-competitive EGFR inhibitor, chemotherapeutic agents, or other antiproliferative agents may be combined with the compounds of this disclosure to treat proliferative diseases and cancer.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

In another aspect, the disclosure provides a kit comprising a compound capable of inhibiting kinase activity selected from one or more compounds of disclosed herein, or pharmaceutically acceptable salts thereof, and instructions for use in treating cancer. In certain embodiments, the kit further comprises components for performing a test to determine whether a subject has activating and/or drug resistance mutations in EGFR.

In another aspect, the disclosure provides a kit comprising a compound capable of inhibiting EGFR activity selected from a compound disclosed herein, or a pharmaceutically acceptable salt thereof.

In another aspect, the disclosure provides a kit comprising a compound capable of inhibiting kinase activity selected from one or more compounds of disclosed herein, or pharmaceutically acceptable salts thereof; a second agent; and instructions for use in treating cancer. In certain embodiments, the kit further comprises components for performing a test to determine whether a subject has activating and/or drug resistance mutations in EGFR. In some embodiments, the second agent is a MEIN inhibitor, a PI3K inhibitor, or an mTor inhibitor. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor, In further embodiments, the ATP-competitive EGFR inhibitor is osimertinib.

In another aspect, the disclosure provides a kit comprising a compound capable of inhibiting EGFR activity selected from a compound of disclosed herein, or a pharmaceutically acceptable salt thereof and a second agent. In some embodiments, the second agent is a MEK inhibitor, a PI3K inhibitor, or an mTor inhibitor. In some embodiments, the second agent prevents EGFR dimer formation in a subject. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In some embodiments, the second agent is an ATP-competitive EGFR inhibitor In further embodiments, the ATP-competitive EGFR inhibitor is osimertinib.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Example 1: Synthesis of Compounds

Scheme 1 - synthesis of Compounds 1 and 6

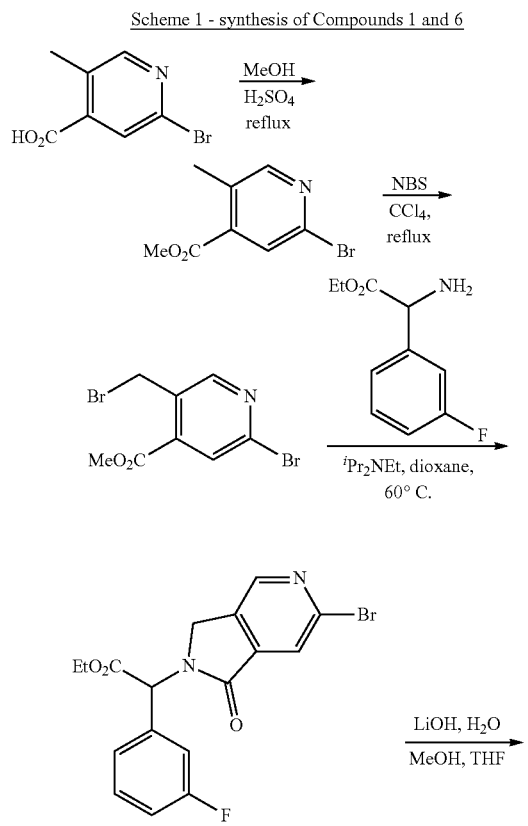

Scheme 2 - synthesis of Compounds 2 and 8

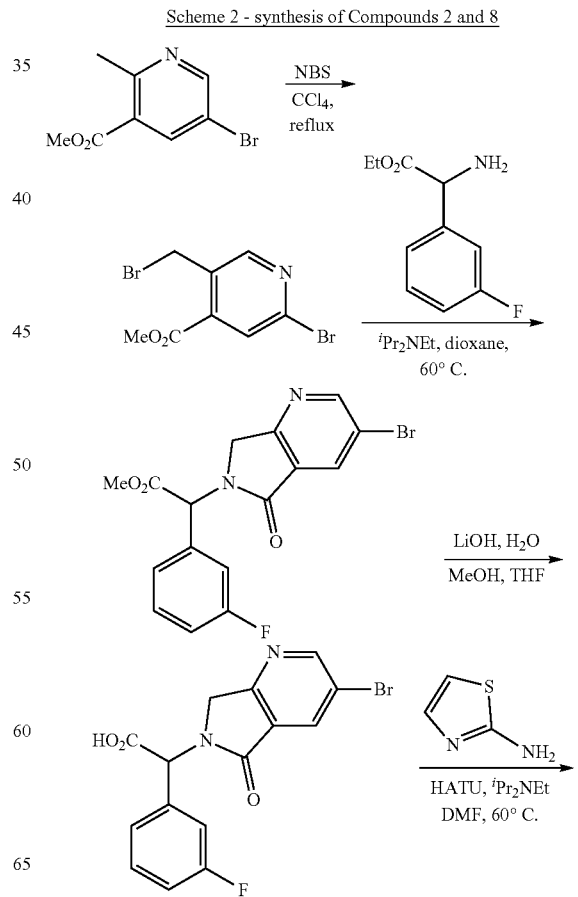

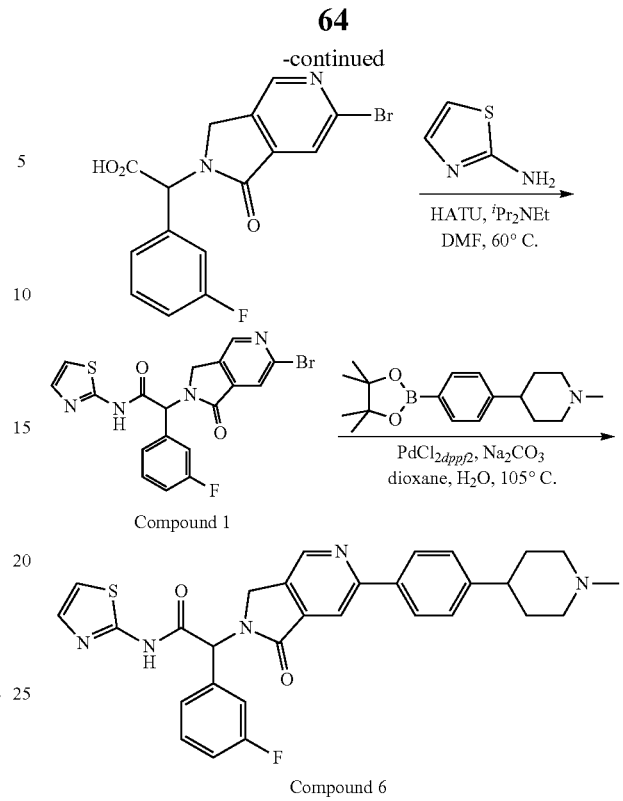

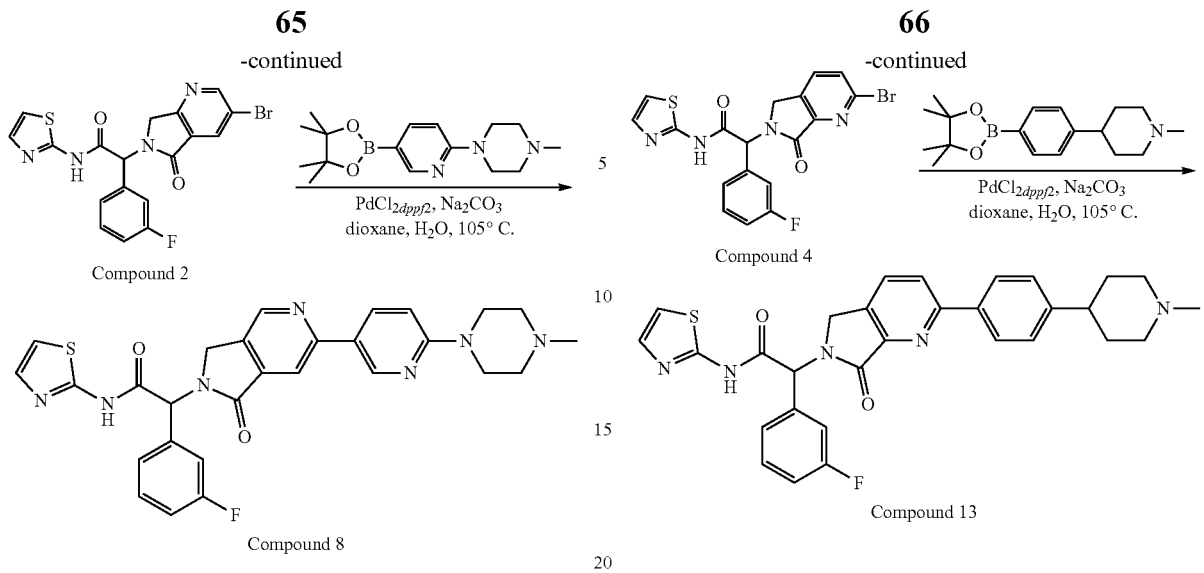

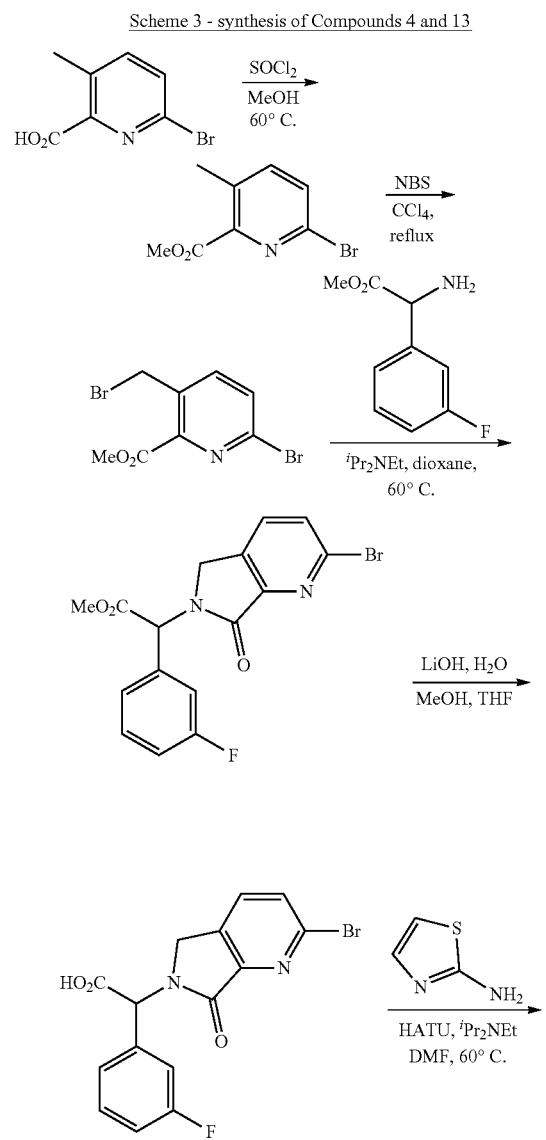

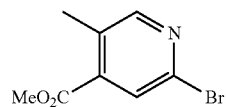

Intermediate 1: Methyl 2-bromo-5-methylisonicotinate

A solution of 2-bromo-5-methylisonicotinic acid (1.0 g, 4.6 mmol), methanol (40 mL), and sulfuric acid (0.5 mL) was heated to reflux for 2 days. After cooling to room temperature, the reaction mixture was treated carefully with solid sodium bicarbonate. The solvent was removed under reduced pressure and the residue partitioned between ethyl acetate (30 mL) and water (30 mL). The aqueous layer was washed with ethyl acetate (2 x 30 mL). The organic extracts were combined, washed with saturated brine (30 mL), dried over sodium sulfate, filtered, and concentrated under reduced pressure to give the title compound (0.9 g, 84%). $^1$H NMR (500 MHz, CDCl$_3$-d) δ 8.34 (s, 1 H) 7.91 (s, 1 H) 3.96 (s, 3 H) 2.53 (s, 3 H); MS (m/z): 231.9 [M+1]$^{+\cdot}$

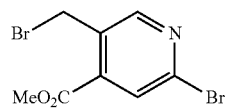

Intermediate 2: Methyl 2-bromo-5-(bromomethyl)isonicotinate

A mixture of methyl 2-bromo-5-methylisonicotinate (0.9 g, 3.9 mmol), benzoyl peroxide (94 mg, 0.39 mmol), and N-bromosuccinimide (694 mg, 3.9 mmol) in carbon tetrachloride (35 mL) was heated to reflux under nitrogen for 2 hours. After cooling to room temperature, the mixture was filtered. The filtrate was concentrated and purified by silica chromatography, eluting with 0-10% ethyl acetate/hexane to give the title compound (650 mg, 54%). $^1$H NMR (500

MHz, CDCl₃-d) δ 8.51 (s, 1 H) 7.97 (s, 1 H) 4.85 (s, 2 H) 4.01 (s, 3 H); MS (m/z): 309.8 [M+1]⁺.

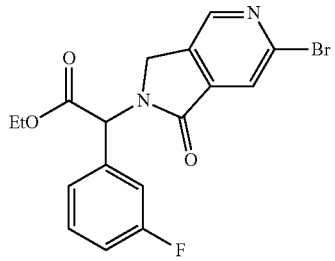 [SMILES: O=C(O)C(c1cccc(F)c1)N1Cc2cnc(Br)cc2C1=O]

Intermediate 3: Ethyl 2-(6-bromo-1-oxo-1,3-di-hydro-2H-pyrrolo[3,4-c]pyridin-2-yl)-2-(3-fluorophenyl)acetate A solution of methyl 2-bromo-5-(bromomethyl)isonicotinate (600 mg, 1.94 mmol), ethyl 2-amino-2-(3-fluorophenyl)acetate (384 mg, 1.94 mmol) and diisopropylethylamine (1 mL, 5.82 mmol) in dioxane (12 mL) was heated at 60° C. for 2 days. After cooling, the reaction mixture was adsorbed onto silica gel and purified by silica chromatography eluting with 0-50% ethyl acetate/hexane to give the title compound (500 mg, 65%). ¹H NMR (500 MHz, CDCl₃-d) δ 8.54 (d, 1 H) 7.97 (s, 1 H) 7.44 (m, 1 H) 7.12 (m, 3 H) 6.30 (s, 1 H) 4.90 (d, 1 H) 4.32 (q, 2 H) 4.04 (d, 1 H) 1.31 (t, 3 H); MS (m/z): 393.0 [M+1]⁺.

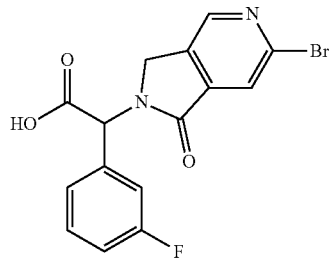

Intermediate 4: 2-(6-Bromo-1-oxo-1,3-dihydro-2H-pyrrolo[3,4-c]pyridin-2-yl)-2-(3-fluorophenyl) acetic acid A mixture of ethyl 2-(6-bromo-1-oxo-1,3-dihydro-2H-pyrrolo[3,4-c]pyridin-2-yl)-2-(3-fluorophenyl) acetate (500 mg, 1.27 mmol) and lithium hydroxide monohydrate (533 mg, 12.7 mmol) in 6 mL of MeOH:H₂O:THF (1:1:1) was stirred for 1 hour, then concentrated under reduced pressure. The residue was suspended in water (10 mL) and filtered. The filtrate was treated with 6N HCl to pH 2, and the precipitate was filtered, washed with water (2×10 mL) and dried to give the title compound (384 mg, 83%). ¹H NMR (500 MHz, d₆-DMSO) δ 8.67 (s, 1 H) 7.96 (s, 1 H) 7.50 (m, 1 H) 7.28 (m, 3 H) 5,99 (s, 1 H) 4.72 (d, 1 H) 4.12 (d, 1 H); MS (m/z): 366.9 [M+1]⁺.

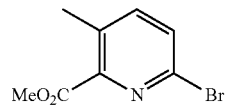

Intermediate 5: Methyl 6-bromo-3-methylpicolinate

Thionyl chloride (3.3 g, 2.02mL, 27.8 mmol) was added dropwise to a solution of 6-bromo-3-methyl picolinic acid (2.0 g, 9.26 mmol) in methanol (40 mL) at 0° C., and the reaction mixture was stirred at 60° C. for 2 hours. The solvent was removed under reduced pressure and the residue partitioned between ethyl acetate (100 mL) and brine (100 mL). The organic layer was washed with brine, dried (Na₂SO₄), filtered and concentrated to give 2.02 g (95%) of the title compound. ¹H NMR (500 MHz, CDCl₃-d) δ 6 7.55 (m, 1H) 7.49 (m, 1H) 4.00 (s, 3H) 2.55 (s, 3H); MS (m/z): 230.10 [M+1]⁺·

Intermediates 6 and 7 were prepared by a similar method to intermediate 2, from the corresponding methyl pyridines.

| Intermediate | Structure/Name | m/z [M + 1]⁺ | NMR ¹H NMR (500 MHz, CDCl₃-d) δ |
|---|---|---|---|
| 6 | Methyl 6-bromo-3-(bromomethyl)picolinate | 309.8 | 7.67 (d, 1H) 7.56 (d, 1H) 4.79 (s, 2H) 3.95 (s, 3H) |
| 7 | Methyl 5-bromo-2-(bromomethyl)nicotinate | — | 8.78 (s, 1H) 8.44 (s, 1H) 5.01 (s, 2H) 4.01 (s, 3H) |

Intermediates 8 and 9 were prepared by a similar method to intermediate 3 from the corresponding pyridine esters 6 and 7 and methyl 2-amino-2-(3-fluorophenyl)acetate.

| Intermediate | Structure/Name | m/z [M + 1]+ | NMR ¹H NMR (500 MHz, d₆-DMSO) δ |
|---|---|---|---|
| 8 | 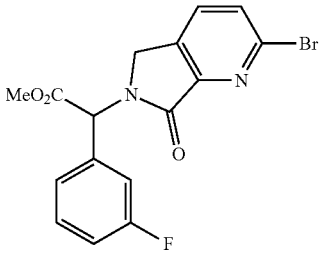<br>Methyl 2-(2-bromo-7-oxo-5,7-dihydro-6H-pyrrolo[3,4-b]pyridin-6-yl)-2-(3-fluorophenyl)acetate | 381.0 | 7.99 (m, 1H) 7.85 (m, 1H) 7.50 (m, 1H) 7.29 (m, 3H) 6.14 (s, 1H) 4.59 (d, 1H) 4.08 (d, 1H) 3.75 (s, 3H) |
| 9 | 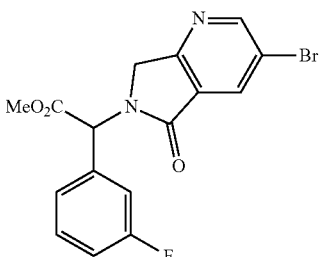<br>Methyl 2-(3-bromo-5-oxo-5,7-dihydro-6H-pyrrolo[3,4-b]pyridin-6-yl)-2-(3-fluorophenyl)acetate | 379.3 | 8.95 (d, 1H) 8.43 (d, 1H) 7.49 (m, 1H) 7.35 (m, 1H) 7.27 (m, 2H) 6.17 (s, 1H) 4.67 (d, 1H) 4.13 (d, 1H) 3.75 (s, 3H) |

Intermediates 10 and 11 were prepared by a similar method to intermediate 4 from the corresponding esters 8 and 9.

| Intermediate | Structure/Name | m/z [M + 1]+ |
|---|---|---|
| 10 | 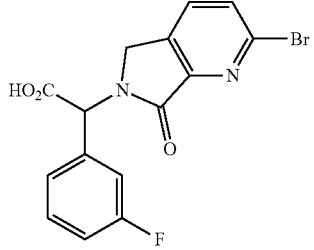 [SMILES: O=C(O)C(c1cccc(F)c1)N1Cc2ccc(Br)nc2C1=O]<br>2-(2-Bromo-7-oxo-5,7-dihydro-6H-pyrrolo[3,4-b]pyridin-6-yl)-2-(3-fluorophenyl)acetic acid | 366.9 |

| Intermediate | Structure/Name | m/z [M + 1]+ |
| --- | --- | --- |
| 11 | 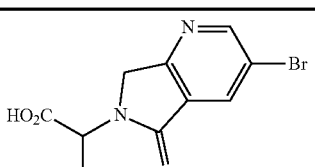<br>2-(3-Bromo-5-oxo-5,7-dihydro-6H-pyrrolo[3,4-b]pyridin-6-yl)-2-(3-fluorophenyl)acetic acid | 367.3 |

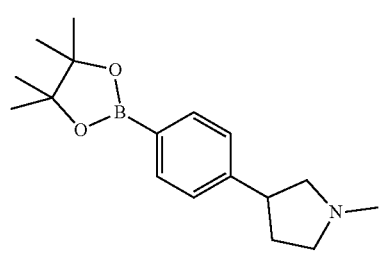

Intermediate 12: 1-Methyl-3-(4-(4,4,5.5-tetramethyl-1,3.2-dioxaborolan-2-yl)phenyl)pyrrolidine A mixture of 3-(4-bromophenyl)-1-methylpyrrolidine (600 mg, 0.25 mmol), bis(pinacolato) diboron (95 mg, 0.375 mmol), potassium acetate (73 mg, 0.75 mmol), and Pd(dppf)Cl$_2$.DCM (0.020 g, 0.025 mmol) in dioxane (1 mL) was heated at 1000 C under nitrogen for 12 hours. The reaction mixture containing the title compound was used directly in the next step.

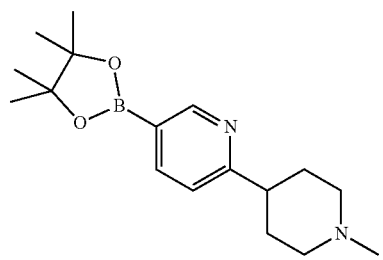

Intermediate 13: 2-(1-Methylpiperidin-4-yl)-5-(4,4.5,5-tetramethyl-1,3,2-dioxaborolan-2-yl)pyridine Intermediate 13 was prepared by a similar method to intermediate 12 from 5-bromo-2-(1-methylpiperidin-4-yl)pyridine.

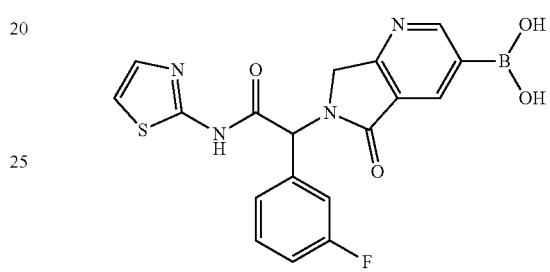

Intermediate 14: (6-(1-(3-Fluorophenyl)-2-oxo-2-(thiazol-2-ylamino)ethyl)-5-oxo-6,7-dihydro-5H-pyrrolo[3,4-b]pyridin-3-yl)boronic acid A mixture of 2-(3-bromo-5-oxo-5,7-dihydro-6H-pyrrolo[3,4-b]pyridin-6-yl)-2-(3-fluorophenyl)-N-(thiazol-2-yl)acetamide (330 mg, 0.738 mmol), bis(pinacolato)diboron (187 mg, 1.11 mmol), potassium acetate (217 mg, 2.21 mmol) and Pd(dppf)Cl$_2$.DCM (60.2 mg, 0.738 mmol) in dioxane (3 mL) was stirred at 100° C. for 12 hours under nitrogen. After cooling, the reaction was diluted with EtOAc (100 mL) and washed with brine. The organic layer was dried over sodium sulfate, filtered, and concentrated under reduced pressure. The residue was purified by silica chromatography (DCM/MeOH) to give the title compound (157 mg, 52%). $^1$H NMR (500 MHz, d$_6$-DMSO) δ 9.06 (s, 1H) 8,58 (s, 2H) 8.50 (s, 1H) 7,51 (m, 2H) 7.28 (m, 4H) 6.31 (s, 1H) 4.76 (d, 1H) 4,16 (d, 1H); MS (m/z): 413.10 [M+1]$^+$.

Scheme 4 - synthesis of Intermediate 17

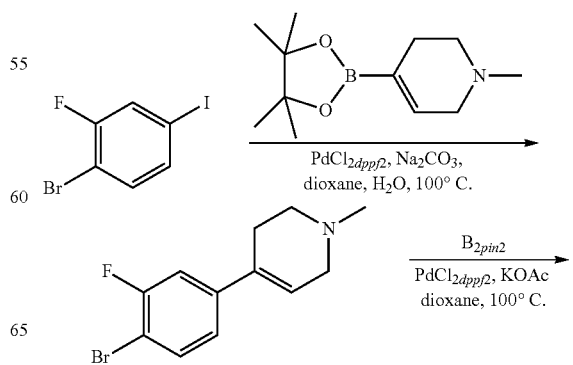

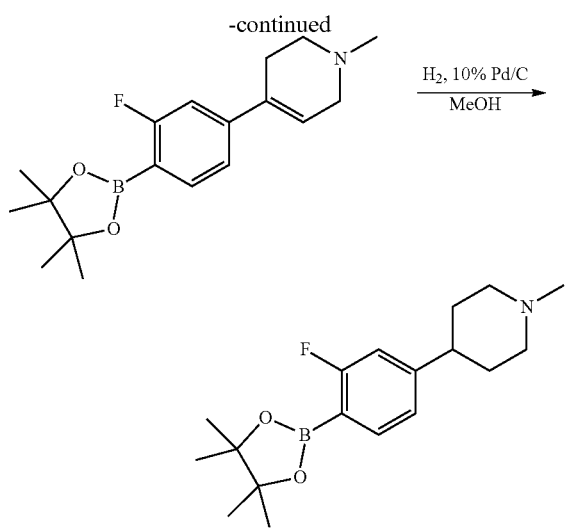

Intermediate 15: 4-(4-Bromo-3-fluorophenyl)-1-methyl-1,2,3,6-tetrahydropyridine A mixture of 1-bromo-2-fluoro-4-iodobenzene (10.0 g, 33.2 mmol), 1-methyl-4-(4,4,5,5-tetramethyl-1,3,2-dioxaborolan-2-yl)-1,2,3,6-tetrahydropyridine (7.40 g, 33,2 mmol), [1,1'-bis(diphenylphosphino)ferrocene]dichloropalladium(II) (2.42 g, 3.32 mmol), sodium carbonate (10.9 g, 99.6 mmol) and dioxane/water (100 mL, 4/1) was degassed under nitrogen twice. The reaction mixture was heated at 100 ° C. for 2 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 50-67% ethyl acetate in petroleum ether to give the title compound (7.0 g, 78%). $^1$H NMR (400 MHz, methanol-$d_4$) δ: 7,51-7.59 (m, 1H), 7.25-7.31 (m, 1H), 7.13-7.23 (m, 1H) 6.23 (dt, 1H), 3.18-3.28 (m, 2H), 2.67-2.75 (m, 2H), 2.54-2.65 Om 2H), 2.39 (s, 3H). MS m/z: 270.1 [M+1]$^+$.

Intermediate 16: 4-(3-Fluoro-4-(4,4,5,5-tetramethyl-,2-dioxaborolan-2-yl)phenyl)-1-methyl-1,2,3,6-tetrahydrobyridine A mixture of 4-(4-bromo-3-fluorophenyl)-1-methyl-1,2,3,6-tetrahydropyridine (1,00 g, 3,70 mmol), 4,4,5,5-tetramethyl-2-(4,4,5,5-tetramethyl-1,3,2-dioxaborolan-2-yl)-1,3,2-dioxaborolane (1.40 g, 5.55 mmol), [1,1'-bis(diphenylphosphino)ferrocene]dichloropalladium(II) (0.541 g, 0,740 mmol), potassium acetate (1,08 g, 11.1 mmol) and dioxane (20 mL) was degassed under nitrogen twice. The reaction mixture was heated at 100 ° C. for 3 h. After cooling to room temperature, the solvent was removed under reduced pressure. The crude product was purified by silica gel column chromatography eluting with 50-100% ethyl acetate in petroleum ether to give the title compound (0.5 g, 37%). $^1$H NMR (400 MHz, methanol-$d_4$) δ: 7.65 (dd, 1H), 7.25 (dd, 1H), 7,11 (dd, 1H), 6,26 (dt, 1H) 3.16-3.23 (m, 2H) 2.74-2.81 (m, 2H), 2.57-2,64 (m, 2H), 2,44 (s, 3H), 1.34 (s, 12H). MS m/z: 318.1 [M+1]$^+$.

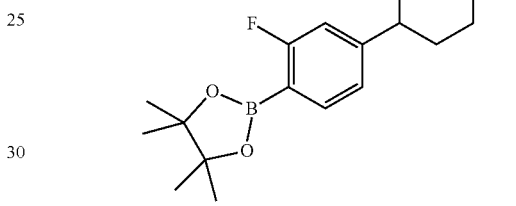

Intermediate 17: 4-(3-Fluoro-4-(4,4,5.5-tetramethyl-2-dioxaborolan-2-Ophenv1)-1-methvlbiberidine To a solution of palladium (10% on carbon, 0.900 g, 0,851 mmol) in methanol (54 mL) was added 4-(3-fluoro-4-(4,4,5,5-tetramethyl-1,3,2-dioxaborolan-2-yl)phenyl)-1-methyl-1,2,3,6-tetrahydropyridine (2.70 g, 8.51 mmol). The flask was evacuated and backfilled with hydrogen and the reaction mixture was allowed to stir at 30°C. under an atmosphere of hydrogen (50 psi) for 48 h. The reaction mixture was filtered through a pad of Celite which was washed several times with methanol. The filtrate was concentrated under reduced pressure to give the title compound (1.89 g, 69%). $^1$H NMR (400 MHz, methanol-$d_4$) δ: 7.58-7.68 (m, 1H), 7.07 (d, 1H), 6.89-7.00 (m, 1H), 3.04 (d, 2H), 2.53-2.69 (m, 1H), 2.37 (s, 3H), 2.23 (t, 2H), 1.72-1.93 (m, 4H) 1.35 (s, 12H).

Scheme 5 - synthesis of Intermediate 21

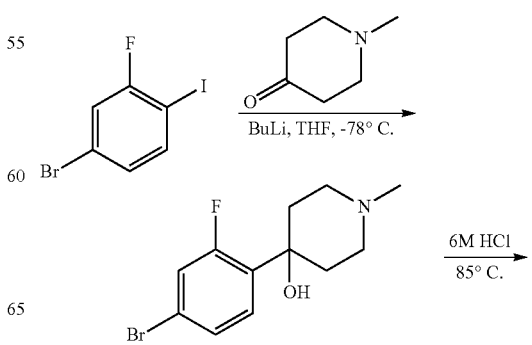

-continued

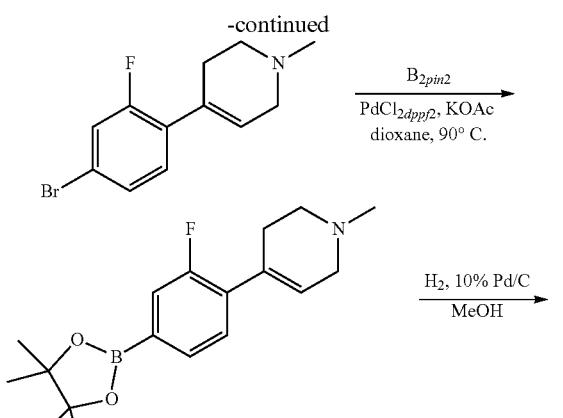

Intermediate 19: 4-(4-Bromo-2-fluoro-phenyl)-1-methyl-3,6-dihydro-2H-pyridine A mixture of 4-(4-bromo-2-fluoro-phenyl)-1-methyl-piperidin-4-ol (13.0 g, 45.1 mmol) and 6 M HCl (70 mL) was heated at 85 ° C. overnight. After cooling to room temperature, the reaction mixture was poured into water, adjusted to pH 8 by sat. sodium bicarbonate and extracted with ethyl acetate three times. The combined organic extracts were washed with brine, dried over sodium sulfate, filtered and concentrated under reduced pressure. The crude product was purified by silica gel column chromatography eluting with 5-66% ethyl acetate in petroleum ether to give the title compound (4.0 g, 31%). MS m/z: 271.7 [M+1]$^+$.

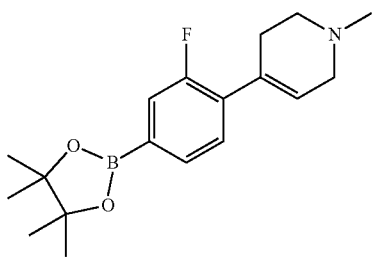

Intermediate 20: 4-[2-Fluoro-4-(4,4,5,5-tetramethyl-1,3,2-dioxaborolan-2-yl)phenyl]-1-methyl-3,6-dihydro-2H-pyridine A mixture of 4-(4-bromo-2-fluoro-phenyl)-1-methyl-3,6-dihydro-2H-pyridine (3,00 g, 11.1 mmol), 4,4,5,5-tetramethyl-2-(4,4,5,5-tetramethyl-1,3,2-dioxaborolan-2-y0-1,3,2-dioxaborolane (2.81 g, 11.1 mmol), [1,1'-bis(diphenylphosphino)ferrocene]dichloropalladium(II) (0.812 g, 1.11 mmol), potassium acetate (3.26 g, 33.3 mmol) and dioxane (30 mL) was degassed under nitrogen twice. The reaction mixture was heated at 90°C. for 16 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 5-50% ethyl acetate in petroleum ether to give the title compound (3.0 g, 85%). $^1$H NMR (400 MHz, methanol-d$_4$) 6: 7.49 (dd, 1H), 7.27-7.40 (m, 2H), 6.01-6.03 (m, 1H), 3.18-3,21 (m, 2H), 2,72-2,80 (m, 2H) 2.57-2.65 (m, 2H), 2.43 (s, 3H) 1.30-1.39 (m, 12H).

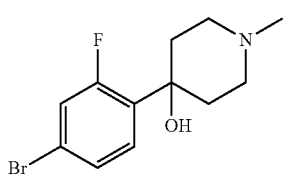

Intermediate 18: 4-(4-Bromo-2-fluoro-phenyl)-1-methyl-piperidin-4-ol

To a solution of 4-bromo-2-fluoro-1-iodo-benzene (24.0 g, 79.7 mmol) in THF (400 mL) at −70C. was added dropwise n-butyllithium (2.5 Min hexane, 31.9 mL, 79.7 mmol). After stirring at −70 ° C. for 30 min, a solution of 1-methylpiperidin-4-one (9.01 g, 79.7 mmol) in THF (20 mL) was added dropwise. After stirring at −70° C. for 1 h, the reaction mixture was poured into sat. ammonium chloride solution and extracted with ethyl acetate three times. The combined organic extracts were washed with brine, dried over sodium sulfate, filtered and concentrated under reduced pressure. The crude product was purified by silica gel column chromatography eluting with 5-66% ethyl acetate in petroleum ether to give the title compound (13.0 g, 57%). MS m/z: 289.8 [M+1]$^+$.

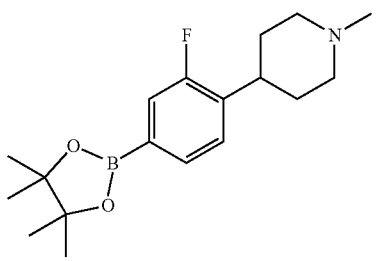

Intermediate 21: 4-12-Fluoro-4-(4,4,5,5-tetramethyl-1,3,2-dioxaborolan-2-yl)phenyl1-1-methyl-piperidine To a solution of palladium (10% on carbon, 1.10 g, 0,945 mmol) in methanol (200 mL) was added 4[2-fluoro-4-(4,4, 5,5-tetramethyl-1,3,2-dioxaborolan-2-yOphenyl]-1-methyl-3,6-dihydro-2H-pyridine (3,00 g, 9.45 mmol). The flask was evacuated and backfilled with hydrogen and the reaction mixture was allowed to stir at 30 ° C. under an atmosphere of hydrogen (30 psi) for 16 h. The reaction mixture was filtered through a pad of Celite which was washed several times with methanol. The filtrate was concentrated under reduced pressure to give the title compound (2.7 g, 85%). $^1$H NMR (400 MHz, methanol-d$_4$) δ: 7.49 (d, 1H), 7.26-7.36 (m, 2H), 3.00-3.10 (m, 2H), 2.83-2.98 (m, 1H), 2.37 (5, 3H), 2.18-2.31 (m, 2H), 1.79-1.89 (m, 4H), 1.27-1.39 (m, 12H).

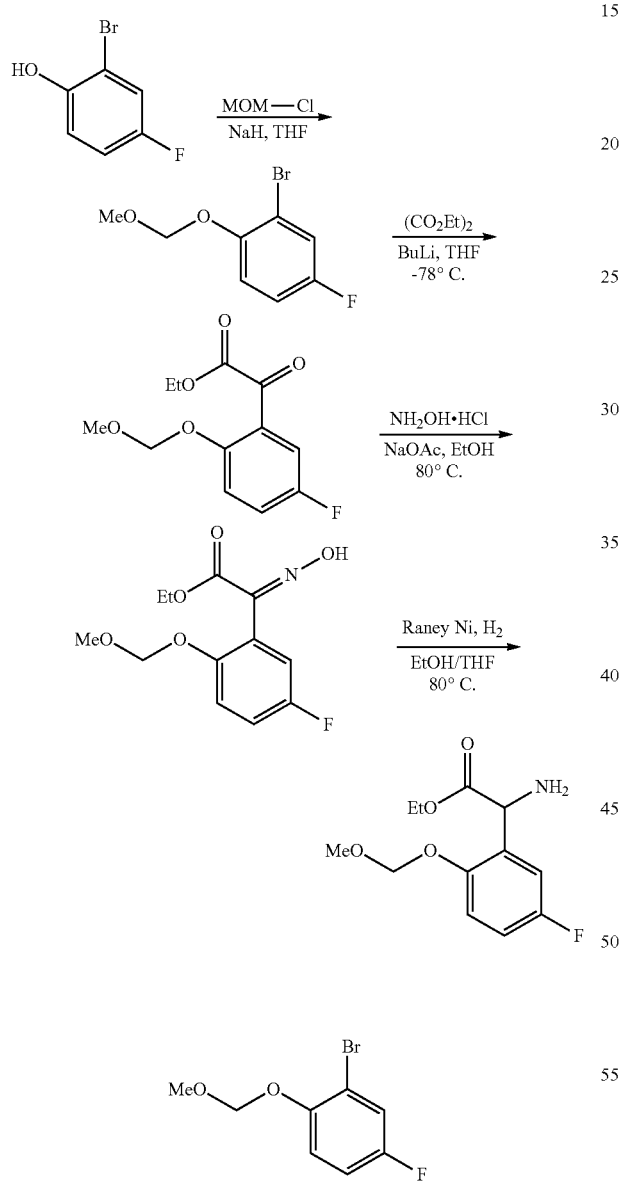

Intermediate 22: 2-Bromo-4-fluoro-1-(methoxymethoxy)benzene

To a solution of 2-bromo-4-fluoro-phenol (100 g, 523 mmol) in THF (1 L) was added sodium hydride (23.0 g, 575 mmol, 60°/h in mineral oil) at 0° C. for 4 h, followed by addition of methoxymethyl chloride (44.9 mL, 601 mmol). After stirring at room temperature for 10 h, the reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 1-10% ethyl acetate in petroleum ether to give the title compound (80 g, 65%). $^1$H NMR (400 MHz, CDCl$_3$) 6: 7.30 (dd, 1H), 7.12 (dd, 1H), 6,97 (m, 1H), 5,07-5.24 (m, 2H), 3.46-3.62 (m, 3H).

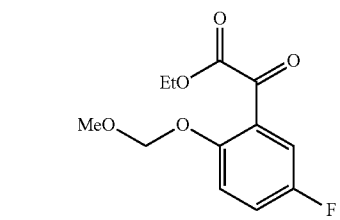 [SMILES: CCOC(=O)C(=O)c1cc(F)ccc1OCOC]

Intermediate 23: Ethyl 2-15-fluoro-2-(methoxymethoxy)phenyl1-2-oxo-acetate

To a solution of 2-bromo-4-fluoro-1-(methoxymethoxy)benzene (80.0 g, 340 mmol) in THF (1 L) at −78° C. was added dropwise n-butyllithium (2.5 M in hexane, 142 mL, 357 mmol). After stirring at −78° C. for 1 h, the reaction mixture was cannulated to a pre-cooled (−78°C.) solution of diethyl oxalate (74.4 g, 510 mmol) in THF (500 mL). Upon completion of addition, the reaction mixture was allowed to warm to room temperature. The reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 10% ethyl acetate in petroleum ether to give the title compound (70 g, 80%). $^1$H NMR (400 MHz, CDCl$_3$) δ: 7.57 (dd, 1H), 7.26-7.31 (m, 1H), 7.18-7.23 (m, 1H), 5.15 (s, 2H), 4.37-4.43 (m, 2H), 3.46-3.50 (m, 3H), 1.35-1.41 (m, 3H).

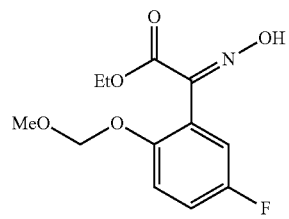 [SMILES: CCOC(=O)C(=NO)c1cc(F)ccc1OCOC]

Intermediate 24: Ethyl-2-[5-fluoro-2-(methoxymethoxy)phenyl]-2-hydroxyimino-acetate To a solution of hydroxylamine hydrochloride (37.9 g, 546 mmol) in ethanol (500 mL) was added ethyl 2-[5-fluoro-2-(methoxymethoxy)phenyl]-2-oxo-acetate (70.0 g, 273 mmol) and sodium acetate (44.7 g, 132 mmol). After stirring at 80 ° C. for 2.5 h, the solvent was removed under reduced pressure and the resulting residue was partitioned between water and dichloromethane. The aqueous phase was extracted with additional dichloromethane. The combined organic extracts were washed with brine, dried over sodium sulfate, filtered and concentrated under reduced pressure to give the title compound (68 g, 92%). $^1$H NMR (400 MHz, CDCl$_3$) δ: 9.76 (br 5, 1H), 7.17-7.23 (m, 1H), 7.07-7.14 (m, 2H), 5.10 (s, 2H), 4.31-4.39 (m, 2H), 3.44-3.48 (m, 3H), 1.35-1.40 (m, 3H).

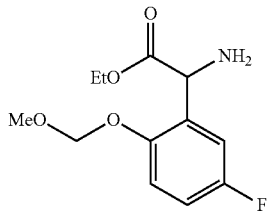 [SMILES: CCOC(=O)C(N)c1cc(F)ccc1OCOC]

Intermediate 25: Ethyl 2-amino-2-[5-fluoro-2-(methoxymethoxy)phenyl]acetate

To a solution of Raney Ni (1.46 g, 25.0 mmol) in EtC$_1$-11THF (650 mL, 4/1) was added ethyl-2-[5-fluoro-2-(methoxymethoxy)phenyl]-2-hydroxyimino-acetate (34.0 g, 125 mmol). The flask was evacuated and backfilled with hydrogen and the reaction mixture was allowed to stir at 70 °C. under an atmosphere of hydrogen (50 psi) for 24 h. The reaction mixture was filtered through a pad of Celite which was washed several times with ethanol. The filtrate was concentrated under reduced pressure and purified by silica gel chromatography eluting with 33% ethyl acetate in petroleum ether to give the title compound (30.6 g, 48%). $^1$H NMR (400 MHz, DMSO-d$_6$) δ: 7.23 (dd, 1H), 7.04-7.08 (m, 2H), 5.14-5.18 (m, 2H), 4.66 (s, 1H), 3.92-4.12 (m, 2H), 3.37 (s, 3H), 1.06-1.22 (m, 3H).

Intermediates 26 and 27 were prepared by a similar method to intermediate 3 from the corresponding intermediates 6 and 7 and ethyl 2-amino-2-[5-fluoro-2-(methoxymethoxy)phenyl]acetate (Intermediate 25).

| Intermediate | | m/z [M + 1]$^+$ | $^1$H NMR (400 MHz, DMSO-d$_6$) δ |
|---|---|---|---|
| 26 | Ethyl 2-(2-bromo-7-oxo-5H-pyrrolo[3,4-b]pyridin-6-yl)-2-[5-fluoro-2-(methoxymethoxy)phenyl]acetate | 454.2 | 8.03-7.98 (m, 1H), 7.83-7.87 (m, 1H), 7.18-7.32 (m, 3H), 6.23 (s, 1H), 5.13-5.25 (m, 2H), 4.64 (d, 1H), 4.15-4.28 (m, 2H), 4.08 (d, 1H), 3.33 (s, 3H), 1.17 (t, 3H) |
| 27 | Ethyl 2-(3-bromo-5-oxo-7H-pyrrolo[3,4-b]pyridin-6-yl)-2-[5-fluoro-2-(methoxymethoxy)phenyl]acetate | 454.0 | 8.93-8.88 (m, 1H), 8.44-8.39 (m, 1H), 7.29-7.17 (m, 3H), 6.25 (s, 1H), 5.26-5.18 (m, 2H), 4.74-4.61 (m, 1H), 4.29-4.14 (m, 2H), 4.11 (d, 1H), 3.35 (s, 3H), 1.12-1.22 (m, 3H) |

Intermediates 28 and 29 were prepared by a similar method to intermediate 4 from the corresponding esters, intermediates 26 and 27.

| Intermediate | | m/z [M + 1]$^+$ | $^1$H NMR (400 MHz, DMSO-d$_6$) δ |
|---|---|---|---|
| 28 | 2-(2-Bromo-7-oxo-5H-pyrrolo[3,4-b]pyridin-6-yl)-2-[5-fluoro-2-(methoxymethoxy)phenyl]acetic acid | 426.8 | 7.94-8.03 (m, 1H), 7.80-7.86 (m, 1H), 7.16-7.25 (m, 3H), 6.17 (s, 1H), 5.12-5.24 (m, 2H), 4.58-4.72 (m, 1H), 4.05 (d, 1H), 3.32 (s, 3H) |
| 29 | 2-(3-Bromo-5-oxo-7H-pyrrolo[3,4-b]pyridin-6-yl)-2-[5-fluoro-2-(methoxymethoxy)phenyl]acetic acid | 426.8 | 8.86-8.93 (m, 1H), 8.36-8.43 (m, 1H), 7.21-7.25 (m, 2H), 7.15-7.19 (m, 1H), 6.19 (s, 1H), 5.13-5.25 (m, 2H), 4.62-4.74 (m, 1H), 4.08 (d, 1H), 3.34 (s, 3H) |

Intermediates 30 and 31 were prepared by a similar method to Example 1 from the corresponding acids, intermediates 28 and 29.

| Intermediate | | m/z [M + 1]$^+$ | $^1$H NMR (400 MHz, DMSO-d$_6$) δ |
|---|---|---|---|
| 30 | 2-(2-Bromo-7-oxo-5H-pyrrolo[3,4-b]pyridin-6-yl)-2-[5-fluoro-2-(methoxymethoxy)phenyl]-N-(2-pyridyl)acetamide | 502.0 | 11.12 (s, 1H), 8.30-8.35 (m, 1H), 8.09 (d, 1H), 7.99 (d, 1H), 7.78-7.87 (m, 2H), 7.23-7.29 (m, 1H), 7.17-7.22 (m, 1H), 7.14 (dd, 1H), 7.04 (dd, 1H), 6.44 (s, 1H), 5.11-5.21 (m, 2H), 4.63 (d, 1H), 3.99 (d, 1H), 3.24 (s, 3H) |

| Intermediate | | m/z [M + 1]⁺ | ¹H NMR (400 MHz, DMSO-d₆) δ |
|---|---|---|---|
| 31 2-(3-Bromo-5-Oxo-7H-pyrrolo[3,4-b]pyridin-6-yl)-2-[5-fluoro-2-(methoxymethoxy)phenyl]-N-(2-pyridyl)acetamide | | 502.8 | 11.05 (s, 1H), 8.90 (d, 1H), 8.41 (d, 1H), 8.31 (d, 1H), 8.09 (d, 1H), 7.75-7.84 (m, 1H), 7.21-7.29 (m, 1H), 7.15-7.21 (m, 1H), 7.13 (dd, 1H), 7.07 (dd, 1H), 6.44 (s, 1H), 5.10-5.22 (m, 2H), 4.66 (d, 1H), 4.01 (d, 1H), 3.24 (s, 3H) |

Preparation of Compounds:

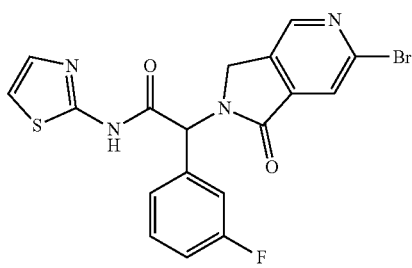 [SMILES: O=C(Nc1nccs1)C(c1cccc(F)c1)N1Cc2cnc(Br)cc2C1=O]

Compound 1: 2-(6-Bromo-1-oxo-1 3-dihydro-2H-pyrrolo[3,4-c]pyhridin-2-(3-fluorophenyl)-N-(thiazol-2-yl)acetamide A mixture of 2-(6-bromo-1-oxo-1,3-dihydro-2H-pyrrolo[3,4-c]pyridin-2-0-2-(3-fluorophenyl)acetic acid (384 mg, 1,06 mmol), HATU (806 mg, 2.12 mmol), and 2-aminothiazole (159 mg, 1.59 mmol) in DMF (3 mL) was treated with DEA (553 mL, 3.18 mmol) and the reaction mixture was heated to 60° C. for 1.5 hours. After cooling, the reaction mixture was poured into water (80 mL) and extracted with ethyl acetate (3×30 mL). The combined organic extracts were washed with saturated brine (30 mL), dried over sodium sulfate, filtered, and concentrated under reduced pressure. The residue was purified by silica chromatography eluting with 0-60% ethyl acetate in hexane to give the title compound (364 mg, 77%). ¹H NMR (500 MHz, CDCl₃-d) δ 8.58 (s, 1 H) 8.15 (s, 1 H) 7,61 (d, 1 H) 7.41 (m, 1 H) 7.24 (d, 1 H) 7.19 (m, 1 H) 7.13 (m, 1 H) 7.09 (d, 1 H) 6.65 (s, 1 H) 5.15 (d, 1 H) 4,24 (d, 1 H); MS (m/z): 449.0 [M+1]⁺.

Compounds 2-5 were prepared by a similar method to Compound 1 from the corresponding acid starting materials and 2-aminothiazole or 2-aminopyridine.

| Compound | Structure/Name | m/z [M + 1]⁺ | ¹H NMR (500 MHz, d₆-DMSO) δ | Starting material |
|---|---|---|---|---|
| 2 | 2-(3-Bromo-5-oxo-5,7-dihydro-6H-pyrrolo[3,4-b]pyridin-6-yl)-2-(3-fluorophenyl)-N-(thiazol-2-ylacetamide | 449.0 | 8.93 (d, 1H) 8.42 (d, 1H) 7.50 (m, 2H) 7.38 (m, 4H) 6.30 (s, 1H) 4.75 (d, 1H) 4.15 (d, 1H) | Intermediate 11 |

-continued

| Compound | Structure/Name | m/z [M + 1]+ | ¹H NMR (500 MHz, d₆-DMSO) δ | Starting material |
|---|---|---|---|---|
| 3 | 2-(3-Bromo-5-oxo-5,7-dihydro-6H-pyrrolo[3,4-b]pyridin-6-yl)-2-(3-fluorophenyl)-N-(pyridin-2-yl)acetamide | 441.0 | 11.06 (s, 1H) 8.91 (s, 1H) 8.41 (s, 1H) 8.32 (m, 1H) 8.08 (m, 1H) 7.81 (m, 1H) 7.50 (m, 1H) 7.28 (m, 3H) 7.15 (m, 1H) 6.38 (s, 1H) 4.80 (d, 1H) 4.09 (d, 1H) | Intermediate 11 |
| 4 | 2-(2-Bromo-7-oxo-5,7-dihydro-6H-pyrrolo[3,4-b]pyridin-6-yl)-2-(3-fluorophenyl)-N-(thiazol-2-yl)acetamide | 449.0 | 8.01 (d, 1H) 7.86 (d, 1H) 7.52 (m, 2H) 7.30 (m, 2H) 7.24 (m, 2H) 6.30 (s, 1H) 4.72 (d, 1H) 4.12 (d, 1H) | Intermediate 10 |
| 5 | 2-(2-Bromo-7-oxo-5,7-dihydro-6H-pyrrolo[3,4-b]pyridin-6-yl)-2-(3-fluorophenyl)-N-(pyridin-2-yl)acetamide | 441.0 | 11.12 (s, 1H) 8.33 (m, 1H) 8.10 (m, 1H) 8.00 (d, 1H) 7.85 (d, 1H) 7.82 (m, 1H) 7.51 (m, 1H) 7.27 (m, 3H) 7.14 (m, 1H) 6.38 (s, 1H) 4.77 (d, 1H), 4.06 (d, 1H) | Intermediate 10 |

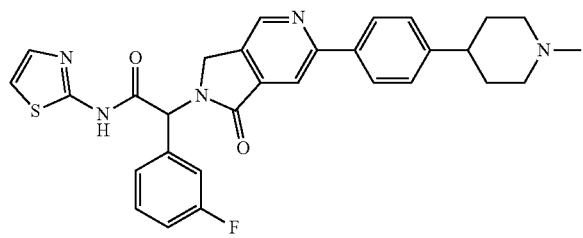 [SMILES: CN1CCC(c2ccc(-c3cc4c(cn3)CN(C(C(=O)Nc3nccs3)c3cccc(F)c3)C4=O)cc2)CC1]

Compound 6: 2-(3-Fluorophenyl)-2-(6-(4-(1-methylpiperidin-4-yl)phenyl)-1-oxo-1,3-dihydro-2H-pyrrolo[3,4-c]pyridin-2-yl)-N-(thiazol-2-yl)acetamide Pd(dppf)Cl$_2$.DCM (25 mg, 0.03 mmol) was added to a mixture of 2-(6-bromo-1-oxo-1,3-dihydro-2H-pyrrolo[3,4-c]pyridin-2-yl)-2-(3-fluorophenyl)-N-(thiazol-2-yl)acetamide (65 mg, 0.0.15 mmol), 1-methyl-4-(4-(4,4,5,5-tetramethyl-1,3,2-dioxaborolan-2-yl)phenyl)piperidine (67 mg, 0,23 mmol), sodium carbonate (48 mg, 0,45 mmol), and 2.5 mL of 4:1 dioxane/water in a sealed vial under nitrogen and the reaction mixture was heated at 105° C. for 1.5 hours. After cooling to room temperature, the reaction mixture was purified by reverse phase HPLC eluting with 0-80% ACN/water to give the title compound (35 mg, 43%). $^1$H NMR (500 MHz, d$_6$-DMSO) δ 9.45 (br s, 1 H) 8,94 (s, 1 H) 8,22 (s, 1 H) 8,17 (m, 2 H) 7,53 (m, 1 H) 7.51 (d, 1 H) 7.38 (d, 2 H) 7.28 (m, 4 H) 6.32 (s, 1 H) 4.87 (d, 1 H) 4.26 (d, 1 H) 3.55 (m, 2 H) 3.10 (m, 2 H) 2.87 (m, 4 H) 2.06 (m, 2 H) 1.87 (m, 2 H); MS (m/z): 542.2 [M+1]+.

Compounds 7-18 were prepared by a similar method to Compound 6 from the corresponding starting materials.

| Cpd | | m/z [M + 1]+ | $^1$H NMR (500 MHz, d$_6$-DMSO) δ | Starting material |
|---|---|---|---|---|
| 7 | 2-(3-Fluorophenyl)-2-(6-(4-(4-methylpiperazin-1-yl)phenyl)-1-oxo-1,3-dihydro-2H-pyrrolo[3,4-c]pyridin-2-yl)-N-(thiazol-2-yl)acetamide | 543.2 | 9.71 (br s, 1 H) 8.87 (s, 1 H) 8.12 (m, 3 H) 7.53 (m, 1 H) 7.51 (s, 1H) 7.31 (m, 2 H) 7.27 (d, 2H) 7.12 (d, 2 H) 6.31 (s, 1 H) 4.85 (d, 1 H) 4.23 (d, 1 H) 4.00 (m, 2 H) 3.54 (m, 2 H) 3.17 (m, 2 H) 3.04 (m, 2 H) 2.87 (s, 3 H) | Compound 1 and |
| 8 | 2-(3-Fluorophenyl)-2-(3-(6-(4-methylpiperazin-1-yl)pyridin-3-yl)-5-oxo-5,7-dihydro-6H-pyrrolo[3,4-b]pyridin-6-yl)-N-(thiazol-2-yl)acetamide | 544.1 | 9.83 (br s, 1H) 9.10 (s, 1H) 8.66 (s, 1H) 8.39 (s, 1H) 8.15 (m, 1H) 7.53 (m, 1H) 7.51 (d, 1H) 7.28 (m, 4H) 7.11 (d, 2H) 6.33 (s, 1H) 4.79 (d, 1H) 4.51 (m, 2H) 4.19 (d, 1H) 3.52 (m, 2H) 3.20 (m, 2H) 3.10 (m, 2H) 2.86 (s, 3H) | Compound 2 and |
| 9 | 2-(3-Fluorophenyl)-2-(3-(4-(1-methylpiperidin-4-yl)phenyl)-5-oxo-5,7-dihydro-6H-pyrrolo[3,4-b]pyridin-6-yl)-N-(thiazol-2-yl)acetamide | 542.2 | 9.51 (s, 1H) 9.10 (d, 1H) 8.38 (d, 1H) 7.82 (d, 2H) 7.54 (m, 1H) 7.51 (d, 1H) 7.40 (d, 2H) 7.29 (m, 4H) 6.34 (s, 1H) 4.81 (d, 1H) 4.22 (d, 1H) 3.53 (m, 2H) 3.09 (m, 2H) 2.88 (m, 1H) 2.84 (s, 3H) 2.06 (m, 2H) 1.88 (m, 2H) | Compound 2 and |

-continued

| Cpd | m/z [M + 1]⁺ | ¹H NMR (500 MHz, d₆-DMSO) δ | Starting material |
|---|---|---|---|
| 10 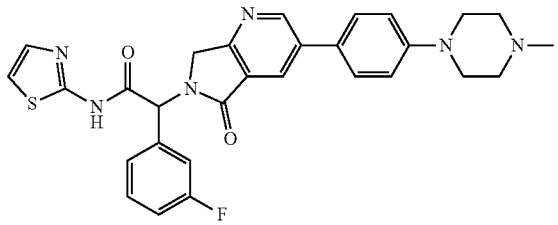 2-(3-Fluorophenyl)-2-(3-(4-(4-methylpiperazin-1-yl)phenyl)-5-oxo-5,7-dihydro-6H-pyrrolo[3,4-b]pyridin-6-yl)-N-(thiazol-2-yl)acetamide | 543.2 | 9.80 (br s, 1H) 9.08 (d, 1H) 8.33 (d, 1H) 7.77 (d, 2H) 7.54 (m, 1H) 7.51 (d, 1H) 7.30 (m, 4H) 7.15 (d, 2H) 6.34 (s, 1H) 4.79 (d, 1H) 4.19 (d, 1H) 3.98 (m, 2H) 3.54 (m, 2H) 3.18 (m, 2H) 3.04 (m, 2H) 2.88 (s, 3H) | Compound 2 and 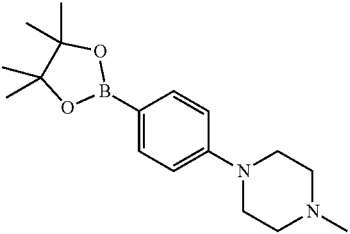 |
| 11 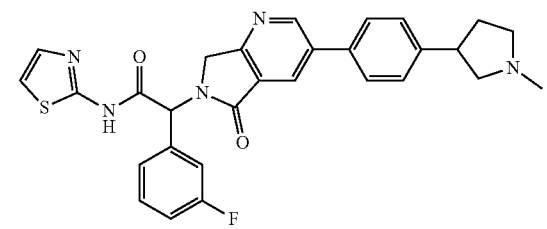 2-(3-Fluorophenyl)-2-(3-(4-(1-methylpyrrolidin-3-yl)phenyl)-5-oxo-5,7-dihydro-6H-pyrrolo[3,4-b]pyridin-6-yl)-N-(thiazol-2-yl)acetamide | 528.2 | 10.13 (br s, 1H) 9.12 (d, 1H) 8.40 (s, 1H) 7.85 (d, 2H) 7.52 (m, 4H) 7.30 (m, 4H) 6.34 (s, 1H) 4.81 (d, 1H) 4.22 (d, 1H) 3.75 (m, 1H) 3.33 (m, 1H) 3.18 (m, 1H) 2.94 (m, 3H) 2.44 (m, 1H) 2.15 (m, 1H) two protons masked by water peak | Compound 2 and Intermediate 12 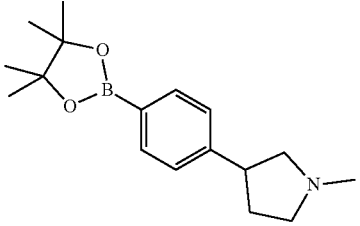 |
| 12 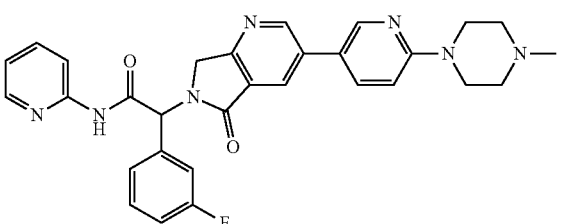 2-(3-Fluorophenyl)-2-(3-(6-(4-methylpiperazin-1-yl)pyridin-3-yl)-5-oxo-5,7-dihydro-6H-pyrrolo[3,4-b]pyridin-6-yl)-N-(pyridin-2-yl)acetamide | 538.2 | 11.08 (s, 1H) 9.90 (brs, 1H) 9.10 (d, 1H) 8.66 (d, 1H) 8.40 (d, 1H) 8.33 (m, 1H) 8.15 (m, 1H) 8.10 (m, 1H) 7.82 (m, 1H) 7.52 (m, 1H) 7.32 (d, 1H) 7.28 (m, 2H) 7.15 (m, 1H) 7.11 (d, 1H) 6.42 (s, 1H) 4.85 (d, 1H) 4.52 (m, 2H) 4.13 (d, 1H) 3.52 (m, 2H) 3.20 (m, 2H) 3.09 (m, 2H) 2.86 (s, 3H) | Compound 3 and 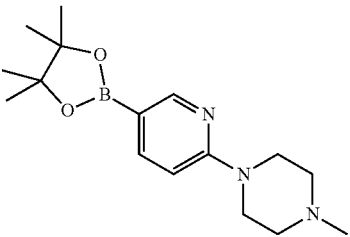 |

-continued

| Cpd | | m/z [M + 1]⁺ | ¹H NMR (500 MHz, d₆-DMSO) δ | Starting material |
|---|---|---|---|---|
| 13 | 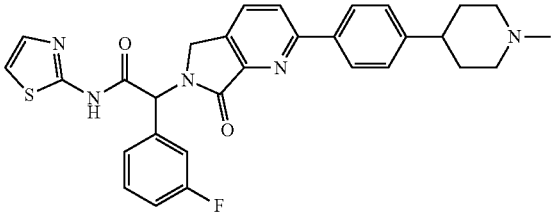 2-(3-Fluorophenyl)-2-(2-(4-(1-methylpiperidin-4-yl)phenyl)-7-oxo-5,7-dihydro-6H-pyrrolo[3,4-b]pyridin-6-yl)-N-(thiazol-2-yl)acetamide | 542.4 | 9.66 (br s, 1H)<br>8.14 (m, 4H)<br>7.54 (m, 1H)<br>7.51 (d, 1H)<br>7.41 (d, 2H)<br>7.31 (m, 2H)<br>7.27 (d, 2H)<br>6.34 (s, 1H)<br>4.76 (d, 1H)<br>4.16 (d, 1H)<br>3.54 (m, 2H)<br>3.10 (m, 2H)<br>2.89 (m, 1H)<br>2.83 (s, 3H)<br>2.06 (m, 2H)<br>1.91 (m, 2H) | Compound 4 and 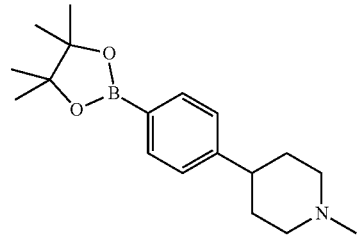 |
| 14 | 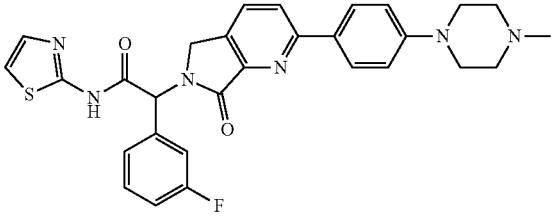 2-(3-Fluorophenyl)-2-(3-(4-(1-methylpiperazin-1-yl)phenyl)-7-oxo-5,7-dihydro-6H-pyrrolo[3,4-b]pyridin-6-yl)-N-(thiazol-2-yl)acetamide | 543.3 | 9.95 (s, 1H)<br>8.09 (m, 3H)<br>8.04 (d, 1H)<br>7.53 (m, 1H)<br>7.51 (d, 1H)<br>7.30 (m, 2H)<br>7.26 (m, 2H)<br>7.15 (d, 2H)<br>6.33 (s, 1H)<br>4.74 (d, 1H)<br>4.13 (d, 1H)<br>4.01 (m, 2H)<br>3.54 (m, 2H)<br>3.16 (m, 2H)<br>3.08 (m, 2H)<br>2.87 (s, 3H) | Compound 4 and 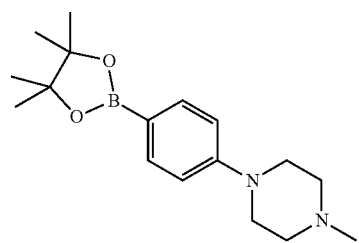 |
| 15 | 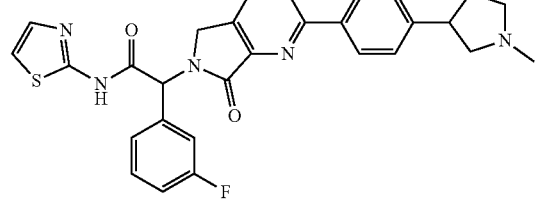 2-(3-Fluorophenyl)-2-(2-(4-(1-methylpyrrolidin-3-yl) phenyl)-7-oxo-5,7-dihydro-6H-pyrrolo[3,4-b]pyridin-6-yl)-N-(thiazol-2-yl)acetamide | 544.1 | 9.92 (br s, 1H)<br>8.95 (s, 1H)<br>8.38 (m, 1H)<br>8.14 (d, 1H)<br>8.07 (d, 1H)<br>7.54 (m, 1H)<br>7.51 (d, 1H)<br>7.30 (m, 2H)<br>7.26 (m, 2H)<br>7.12 (d, 1H)<br>6.33 (s, 1H)<br>4.75 (d, 1H)<br>4.55 (m, 2H)<br>4.14 (d, 1H)<br>3.53 (m, 2H)<br>3.22 (m 2H)<br>3.11 (m, 2H)<br>2.86 (s, 3H) | Compound 4 and 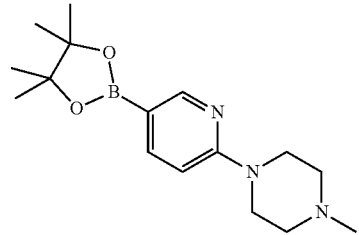 |

| Cpd | | m/z [M + 1]⁺ | ¹H NMR (500 MHz, d₆-DMSO) δ | Starting material |
|---|---|---|---|---|
| 16 | 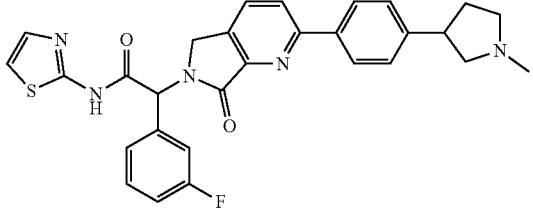<br>2-(3-Fluorophenyl)-2-(2-(4-(1-methylpyrrolidin-3-yl) phenyl)-7-oxo-5,7-dihydro-6H-pyrrolo[3,4-b]pyridin-6-yl)-N-(thiazol-2-yl)acetamide | 528.3 | | Compound 4 and Intermediate 12<br>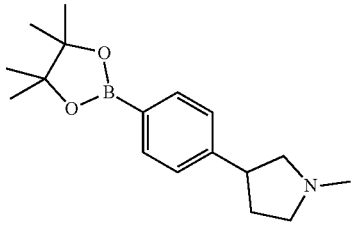 |
| 17 | 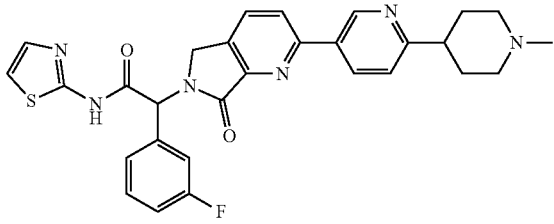<br>2-(3-Fluorophenyl)-2-(2-(6-(1-methylpiperidin-4-yl) pyridin-3-yl)-7-oxo-5,7-dihydro-6H-pyrrolo[3,4-b]pyridin-6-yl)-N-(thiazol-2-yl)acetamide | 543.2 | 9.41 (br s, 1H)<br>9.26 (d, 1H)<br>8.47 (m, 1H)<br>8.25 (d, 1H)<br>8.17 (d, 1H)<br>7.55 (m, 1H)<br>7.51 (m, 2H)<br>7.31 (m, 4H)<br>6.34 (s, 1H)<br>4.79 (d, 1H)<br>4.18 (d, 1H)<br>3.56 (m, 2H)<br>3.10 (m, 3H)<br>2.83 (d, 3H)<br>2.14 (m, 2H)<br>2.01 (m, 2H) | Compound 4 and Intermediate 13<br>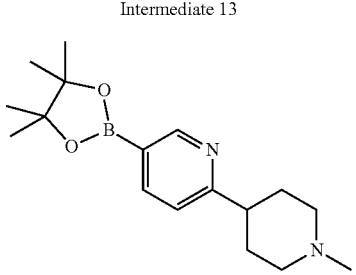 |
| 18 | 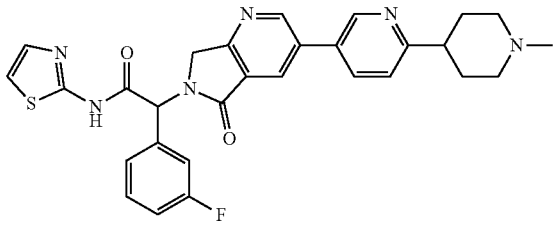<br>2-(3-Fluorophenyl)-2-(3-(6-(1-methylpiperidin-4-yl)pyridin-3-yl)-5-oxo-5,7-dihydro-6H-pyrrolo[3,4-b]pyridin-6-yl)-N-(thiazol-2-yl)acetamide | 543.1 | 9.48 (br s, 1H)<br>9.17 (d, 1H)<br>9.00 (s, 1H)<br>8.50 (d, 1H)<br>8.25 (m, 1H)<br>7.53 (m, 1H)<br>7.51 (d, 1H)<br>7.47 (d, 1H)<br>7.29 (m, 4H)<br>6.34 (s, 1H)<br>4.82 (d, 1H)<br>4.23 (d, 1H)<br>3.54 (m, 2H)<br>3.11 (m, 2H)<br>3.04 (m, 1H)<br>2.83 (s, 3H)<br>2.12 (m, 2H)<br>1.98 (m, 2H) | Intermediate 14<br>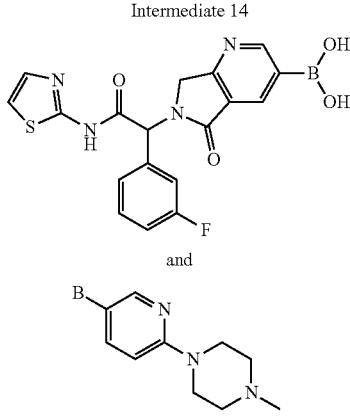<br>and<br>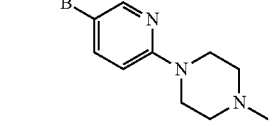 |

Compounds 19 and 20 were prepared by a similar method to Compound 6 from the corresponding starting materials.

(0.05% HCl modifier) to give the title compound (19 mg, 18%). ¹H NMR (DMSO-d6) δ: 10.96 (br s, 1H), 9.91 (br s,

| Cpd | | m/z [M + 1]⁺ | ¹H NMR d₆-DMSO) δ | Starting materials |
|---|---|---|---|---|
| 19 | 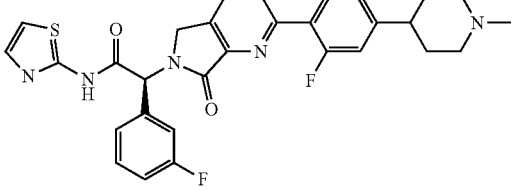<br>2-[2-[2-Fluoro-4-(1-methyl-4-piperidyl)phenyl]-7-oxo-5H-pyrrolo[3,4-b]pyridin-6-yl]-2-(3-fluorophenyl)-N-thiazol-2-yl-acetamide | 560.3 | 8.10-8.17 (m, 1H)<br>7.86-7.97 (m, 2H)<br>7.48-7.57 (m, 2H)<br>7.23-7.33 (m, 6H)<br>6.34 (s, 1H)<br>4.81 (d, 1H)<br>4.18 (d, 1H)<br>2.84-2.94 (m, 2H)<br>2.53-2.61 (m, 1H)<br>2.21 (s, 3H)<br>1.90-2.04 (m, 2H)<br>1.67-1.86 (m, 4H) | Compound 4 and Intermediate 12<br>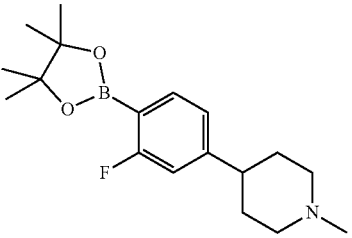 |
| 20 | 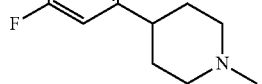<br>2-[2-[3-Fluoro-4-(1-methyl-4-piperidyl)phenyl]-7-oxo-5H-pyrrolo[3,4-b]pyridin-6-yl]-2-(3-fluorophenyl)-N-thiazol-2-yl-acetamide; hydrochloride | 560.2 | 10.49 (br s, 1H)<br>8.23 (d, 1H)<br>8.14 (d, 1H)<br>8.03 (d, 1H)<br>7.95-7.99 (m, 1H)<br>7.43-7.58 (m, 3H)<br>7.23-7.36 (m, 4H)<br>6.36 (s, 1H)<br>4.79 (d, 1H)<br>4.18 (d, 1H)<br>3.45-3.57 (m, 2H)<br>3.08-3.20 (m, 3H)<br>2.78 (d, 3H)<br>1.91-2.21 (m, 4H) | Compound 4 and Intermediate 21<br>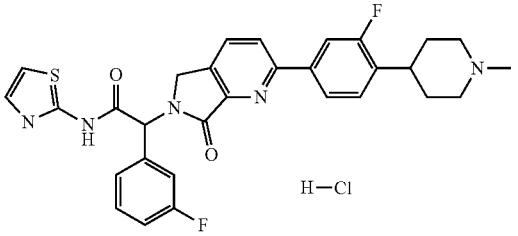 |

Compound 21: 2-(5-Fluoro-2-hydroxy-phenyl)-2-[2-[4-(1-methyl-4-piperidyl)phenyl]-7-oxo-5H-pyrrolo[3,4-b]pyridin-6-yl]-N-(2-pyridyl)acetamide; hydrochloride

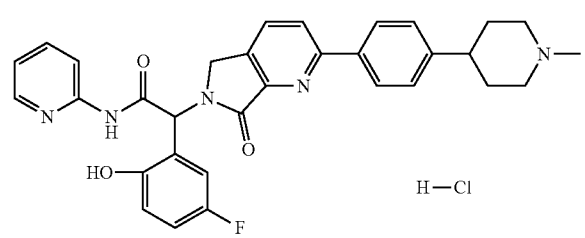 [SMILES: CN1CCC(c2ccc(-c3ccc4c(n3)C(=O)N(C(C(=O)Nc3ccccn3)c3cc(F)ccc3O)C4)cc2)CC1 ; Cl]

A mixture of 2-(2-bromo-7-oxo-5H-pyrrolo[3,4-b]pyridin-6-yl)-2-[5-fluoro-2-(methoxymethoxy)phenyl]N-(2-pyridyl) acetamide (100 mg, 0.199 mmol), 1-methyl-4-[4-(4,4,5,5-tetramethyl-1,3,2-dioxaborolan-2-yl)phenyl]piperidine (89.7 mg, 0.298 mmol), sodium carbonate (63.2 mg, 0.597 mmol) and dioxane/water (2 mL, 4/1) was degassed under nitrogen twice. [1,1' bis(diphenylphosphino)-ferrocene]dichloropalladium(11) (14.5 mg, 0.020 mmol) was added and then the reaction was degassed under nitrogen once more. The reaction mixture was heated at 100° C. for 3 h and the de-MOM product was observed. After cooling to room temperature, the reaction mixture was poured into water and extracted with ethyl acetate three times. The combined organic extracts were washed with brine, dried over sodium sulfate, filtered and concentrated under reduced pressure. The crude product was purified by reverse phase HPLC eluting with 0-100% ACN/water 1H), 8.33 (d, 1H), 8.04-8.15 (m, 5H), 7.77-7.86 (m, 1H), 7.41 (d, 2H), 7.08-7,16 (m, 2H), 6.97 (d, 1H), 6.89-6.94 (m, 1H), 6.42 (s, 1H), 4.67 (d, 1H), 4.01 (d, 1H), 2.88-2.98 (m, 2H), 2.54-2.60 (m, 1H), 2.25 (s, 3H), 1.99-2.12 (m, 2H), 1.67-1.86 (m, 4H). MS m/z: 552.3 [M+1]⁺.

Compound 22: 2-(5-Fluoro-2-hydroxy-phenyl)-2-[3-[4-(1-methyl-4-piperidyl)phenyl]-5-oxo-7H-Pyrrolo[3,4-b]pyridin-6-yl]-N-(2-pyridyl)acetamide; hydrochloride

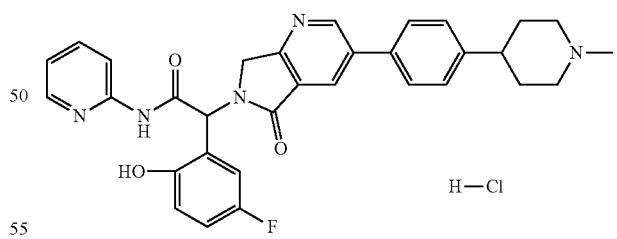

The title compound was prepared by a similar method to Example 21 from 2-(3-bromo-5-oxo-7H-pyrrolo[3,4-b]pyridin-6-yl)-2-[5-fluoro-2-(methoxymethoxy)phenyl]-N-(2-pyridyl)acetamide (intermediate 31). ¹H NMR (DMSO-d₆) δ6: 10.90 (br s, 1H), 9.89 (br s, 1H), 9.06 (d, 1H), 8.28-8.34 (m, 2H), 8.04-8.15 (m, 1H), 7.72-7.83 (m, 3H), 7.40 (d, 2H), 7.07-7.16 (m, 2H), 6.87-7.00 (m, 2H), 6.39 (s, 1H), 4.70 (d, 1H), 4.02 (d, 1H), 2.86-2.98 (m, 2H), 2.53-2,59 (m, 1H), 2,24 (s, 3H), 1.98-2.11 (m, 2H), 1.66-1.85 (m, 4H). MS m/z: 552.3 [M+1]⁺,

Example 2: HTRF-Based EGFR Biochemical Assays

EGFR biochemical activity measurements were carried out using the homogeneous time-resolved fluorescence (HTRF) assay (Cisbio). Inhibitors and DMSO normalizations were first dispensed to empty black low-volume 384-well plates (Corning) with D300 digital liquid dispenser (HP). All reactions were carried out at room temperature and solutions were added to plates with a Multidrop Combi Reagent Dispenser (ThermoFisher). The reaction mixture (10 µL final volume) contained 1 µM tyrosine kinase peptide-biotin substrate and mutant EGFR in a reaction buffer (50 mM HEPES pH 7,0, 5 mM $MgCl_2$, 1 mM $MnCl_2$, 0.01% BSA, 2 mM TCEP, 0.1 mM $NaVO_4$). Enzyme concentrations were adjusted to accommodate varying kinase activities (L858R 0.1 nM, L858R!T790M 0,02 nM). Enzyme reaction solution (2× concentrations, 5 µL) was added to 384-well plates containing compounds and incubated for 30 mins. Enzyme reactions were initiated with the addition of 5 pL of ATP to a final concentration of 100 µM and reacted for 20 mins. Reactions were quenched with the addition of 10 µL of phospho-tyrosine antibody-Europium(III) cryptate (1-to-180 volume ratio) and Streptavidin-XL665 (46.7 nM) in EDTA-containing detection buffer, then incubated at room temperature for 1 hour, and read with a PHERAstar plate reader (excitation =337 nm, emission =620 nm and 665 nm). IC50 values were determined by inhibition curves (11-point curves from 1.0 µM to 0.130 nM or 23-point curves from 1.0 µM to 0.130 µM) in triplicate with non-linear least squares fit in GraphPad Prism 7.0d,

TABLE 3

HTRF Activity

| Compound # | $IC_{50}$ (L858R/T790M) (nM) | $IC_{50}$ (L858R) (nM) |
| --- | --- | --- |
| 1 | 104 | >1 µM |
| 2 | 15 | 318 |
| 3 | 40 | >1 µM |
| 4 | 14 | >1 µM |
| 5 | 114 | >1 µM |
| 6 | 6 | 60 |
| 7 | 10 | 301 |
| 8 | 1 | 20 |
| 9 | 1 | 5 |
| 10 | 4 | 46 |
| 11 | 3 | 27 |
| 12 | 41 | >1 µM |
| 13 | 1 | 7 |
| 14 | 4 | 32 |
| 15 | 6 | 83 |
| 16 | 1 | 6 |
| 17 | 7 | 36 |
| 18 | 9 | 126 |
| 19 | 0.7 | 4 |
| 20 | 1 | 5 |
| 21 | 0.4 | 4 |
| 22 | 1 | 5 |

Example 3: Ba/F3 Cell Proliferation Models

The EGFR mutant L858R, Del E746_A750, L858R/T790M, Del E746_A750/T790M, L858R/T790MIC797S, and DellT790MIC797S Ba/F3 cells have been previously described (Zhou, W., et al, Nature 462, 2009, 1070-1074). All cell lines were maintained in RPM I 1640 (Cellgro; Mediatech Inc., Herndon, CA) supplemented with 10% FBS, 100 units/mL penicillin, 100 units/mL streptomycin. The EGFR 1941 R mutation was introduced via site directed mutagenesis using the Quick Change Site-Directed Mutagenesis kit (Stratagene; La Jolla, CA) according to the manufacturer's instructions. All constructs were confirmed by DNA sequencing. The constructs were shuttled into the retroviral vector JP1540 using the Cre-recombination system (Agilent Technologies, Santa Clara, CA). Ba/F3 cells were then infected with retrovirus per standard protocols, as described previously (Zhou, et al, Nature 2009). Stable clones were obtained by selection in puromycin (2 µg/ml), Growth and inhibition of growth was assessed by the Cell Titer Glo assay (Promega, Madison, WI) and was performed according to the manufacturer's instructions. The Cell Titer Glo assay is a luminescence-based method used to determine the number of viable cells based on quantitation of the ATP present, which is directly proportional to the amount of metabolically active cells present. Ba/F3 cells of different EGFR genotypes were exposed to compounds as a single agent or in combination with 1pg/mIcetuximab for 72 hours and the number of cells used per experiment was determined empirically as has been previously established (Zhou, et al., Nature 2009). All experimental points were set up in triplicates in 384-well plates and all experiments were repeated at least three times. The luminescent signal was detected using a spectrometer and the data was graphically displayed using GraphPad Prism version 5.0 for Windows, (GraphPad Software; www.graphpad.com). The curves were fitted using a non-linear regression model with a sigmoidal dose response.

TABLE 4

Inhibition of Proliferation of EGFR L858R/T790M mutant Ba/F3 Cells

| Compound number | $IC_{50}$ (µM) + cetuximab |
| --- | --- |
| 1 | 5.48 |
| 2 | 0.38 |
| 3 | 2.37 |
| 4 | 1.76 |
| 5 | >10 |
| 6 | 0.13 |
| 7 | 0.48 |
| 8 | 0.20 |
| 9 | 0.01 |
| 10 | 0.10 |
| 11 | 0.05 |
| 12 | 1.91 |
| 13 | 0.02 |
| 14 | 0.12 |
| 15 | 0.33 |
| 16 | 0.04 |
| 17 | 0.14 |
| 18 | 0.22 |
| 19 | 0.03 |
| 20 | 0.02 |
| 21 | 0.01 |
| 22 | 0.03 |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:
1. A compound of Formula (I):

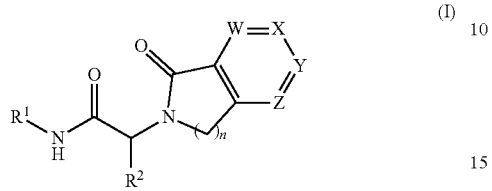

or a pharmaceutically acceptable salt or prodrug thereof, wherein:
- $R^1$ is aryl or 5-to 6-membered heteroaryl;
- $R^2$ is phenyl or pyridinyl, wherein the phenyl or pyridinyl is optionally substituted one or two times, independently, with $C_1$-$C_3$ alkyl, $C_1$-$C_3$ haloalkyl, $C_1$-$C_3$ alkoxy, $C_1$-$C_3$ haloalkoxy, halogen, OH, $NO_2$, $NH_2$, $(CH_2)_pOH$, $S(O)_qH$, $S(O)_qNH_2$, or CN;
- W and Z are each independently N, CH, CF, or C-($C_1$-$C_3$ alkyl);
- X and Y are each independently N, CH, or $CR^3$;
- provided that at least one of W, X, Y, or Z is N, and provided that at least one of W, X, Y, or Z is CH or $CR^3$;
- $R^3$, for each occurrence, is halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkenyl, $C_6$-$C_{10}$ aryl, 5- to 6-membered heteroaryl, or 5- to 7-membered heterocyclyl, wherein the alkyl, alkenyl, or alkynyl are each optionally substituted one, two, or three times with R4, and wherein the aryl, heteroaryl, or heterocyclyl are each optionally substituted one, two, or three times with $R^5$;
- $R^4$, for each occurrence, is independently H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5- to 6-membered heteroaryl), or $(CH_2)_{0-3}$-(5- to 7-membered heterocyclyl), wherein the aryl, heteroaryl, or heterocyclyl are each optionally substituted one, two, or three times with $R^5$;
- $R^5$, for each occurrence, is independently $C_1$-$C_6$ alkyl, $C_1$-$C_6$ haloalkyl, $C_1$-$C_6$ alkoxy, $C_1$-$C_6$ haloalkoxy, halogen, COOH, $C(O)O(C_1$-$C_6$ alkyl), $O(CH_2)_{1-3}$—OH, $NH_2$, OH, CN, $(CH_2)_{0-3}$—($C_6$-$C_{10}$ aryl), $(CH_2)_{0-3}$-(5- to 6-membered heteroaryl), or $(CH_2)_{0-3}$-(5- to 7-membered heterocyclyl), wherein the aryl, heteroaryl, or heterocyclyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, $NH(C_1$-$C_6$ alkyl), $N(C_1$-$C_6$ alkyl)$_2$, $SO_2NH_2$, $(CH_2)_{1-2}$—OH, $C(O)(CH_2)_{1-2}$—OH, and $C(O)O(C_1$-$C_6$ alkyl);
- n is 1 or 2;
- p is 1, 2, 3, or 4; and
- q is 0, 1, or 2.

2. The compound of claim 1, wherein $R^1$ is thiazolyl or pyridinyl.

3. The compound of claim 1, wherein $R^2$ is phenyl substituted one or two times, independently, with halogen or OH.

4. The compound of claim 1, wherein:
- n is 1 and X is $CR^3$;
- n is 2 and X is $CR^3$;
- n is 1 and Y is $CR^3$; or
- n is 2 and Y is $CR^3$.

5. The compound of claim 1, wherein $R^3$ is:

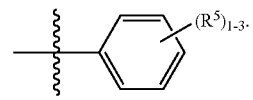

6. The compound of claim 5, wherein $R^5$, for each occurrence, is independently halogen or 5- to 7-membered heterocyclyl wherein the heterocycle is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy.

7. The compound of claim 5, wherein $R^3$ is selected from:

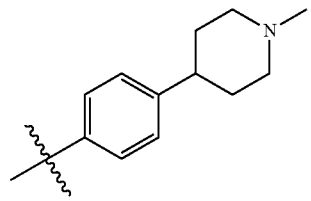

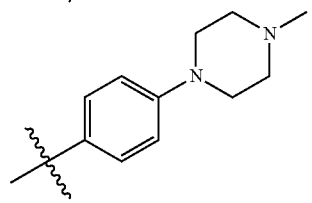

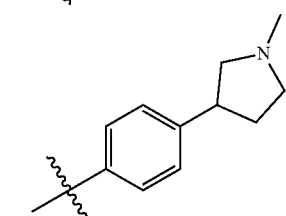

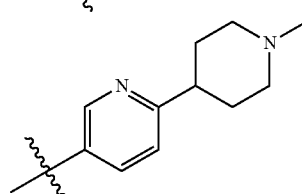

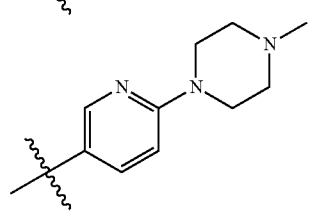

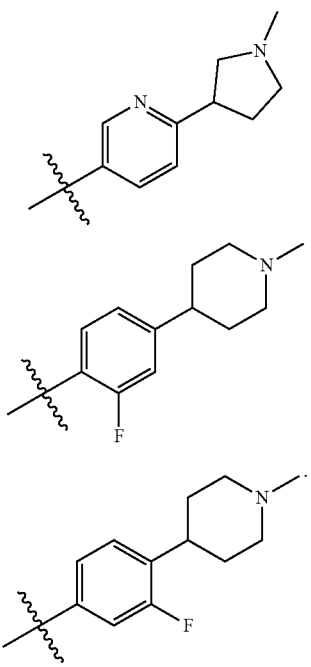
8. The compound of claim 1, selected from the group consisting of:
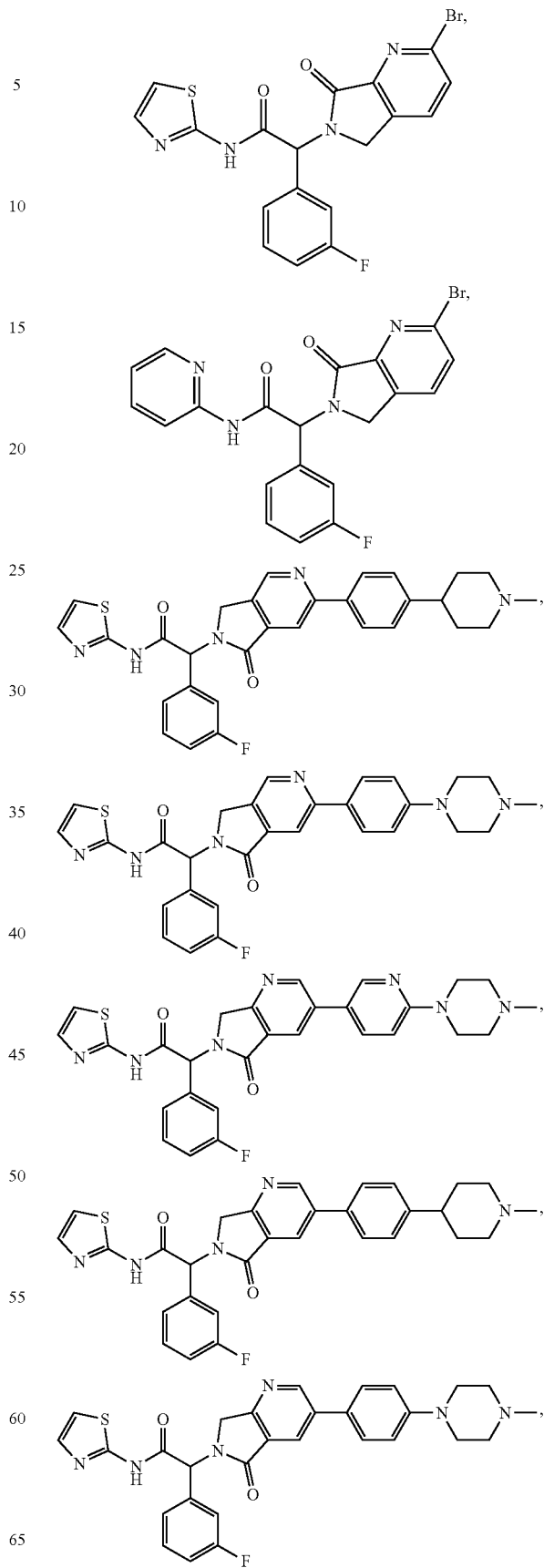

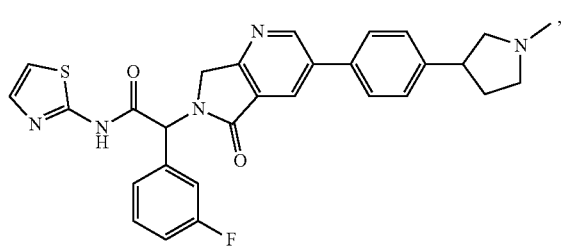
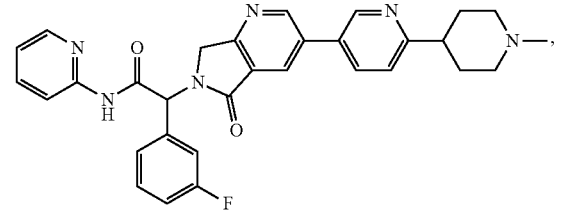
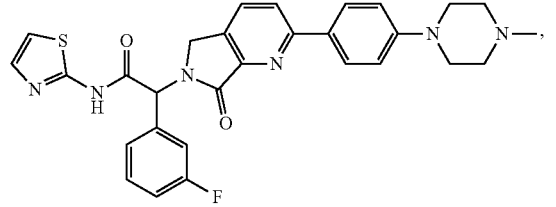
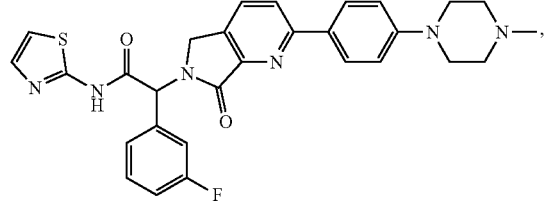
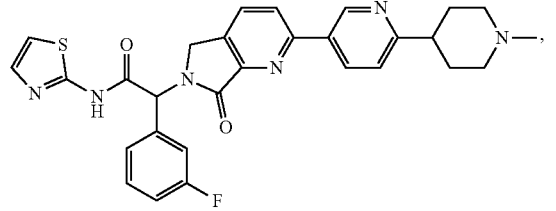
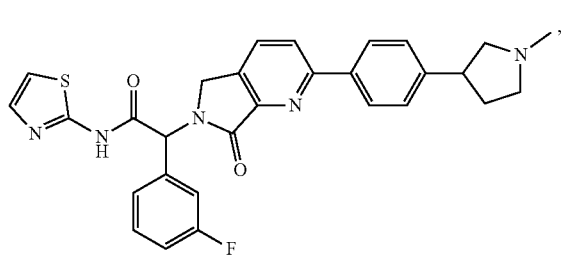
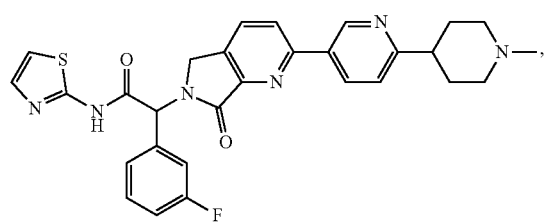

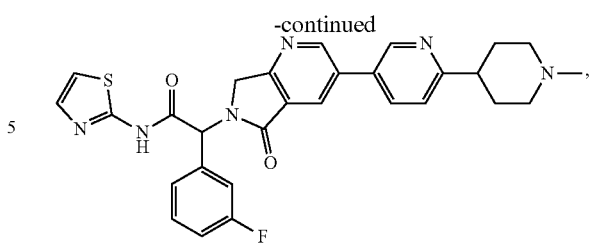
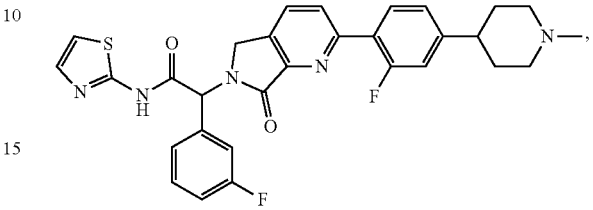
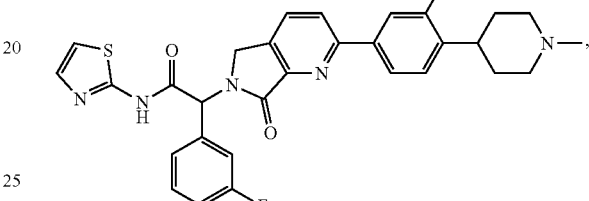
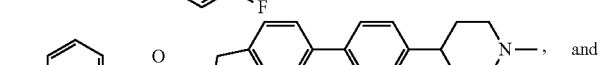
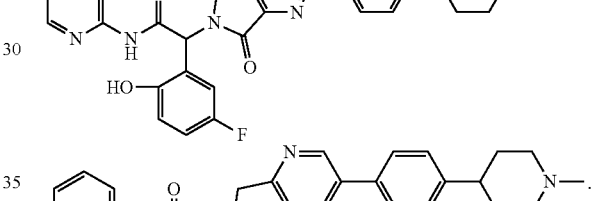
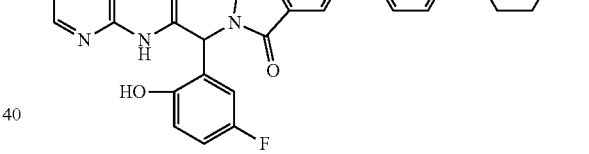

9. A pharmaceutical composition comprising the compound of claim 1, and a pharmaceutically acceptable carrier.

10. The pharmaceutical composition of claim 9, further comprising a second agent, wherein said second agent is an ATP-competitive EGFR inhibitor or an agent that prevents EGFR dimer formation in a subject.

11. A method of inhibiting a kinase, comprising administering to a subject in need thereof an effective amount of the compound of claim 1.

12. The method of claim 11, wherein the kinase to be inhibited is epidermal growth factor receptor (EGFR).

13. The method of claim 12, wherein the EGFR to be inhibited contains one or more mutations selected from the group consisting of T790M, L718Q, L844V, V948R, L858R, I941R, and C797S.

14. A method of treating a kinase-mediated disorder, comprising administering to a subject in need thereof an effective amount of the compound of claim 1.

15. The method of claim 14, wherein the kinase-mediated disorder is resistant to an EGFR-targeted therapy selected from the group consisting of gefitinib, erlotinib, and osimertinib.

16. The method of claim 14, further comprising administering to the subject a second agent, wherein said second agent is an ATP-competitive EGFR inhibitor or an agent that prevents EGFR dimer formation in the subject.

17. A method of treating cancer or a proliferation disease, comprising administering to a subject in need thereof an effective amount of the compound of claim 1.

18. The method of claim 17, wherein the cancer is lung cancer, breast cancer, glioma, squamous cell carcinoma, or prostate cancer.

19. The method of claim 17, further comprising administering to the subject a second agent, wherein said second agent is an ATP-competitive EGFR inhibitor or an agent that prevents EGFR dimer formation in the subject.

20. A kit comprising a compound capable of inhibiting EGFR activity that is a compound of claim 1, or a pharmaceutically acceptable salt thereof, and instructions for use in treating cancer.

* * * * *